(12) United States Patent
Fein et al.

(10) Patent No.: US 7,151,246 B2
(45) Date of Patent: Dec. 19, 2006

(54) IMAGING SYSTEM AND METHODOLOGY

(75) Inventors: Howard Fein, Richmond Heights, OH (US); Andrew G. Cartlidge, Palm Beach Gardens, FL (US)

(73) Assignees: Palantyr Research, LLC, Cleveland, OH (US); Angkor Technology, LLP, Cleveland, OH (US); Himanshu S. Amin, Solon, OH (US); Daniel B. Bortnick, Mentor, OH (US); Gregory Turocy, Westlake, OH (US)

( * ) Notice: Subject to any disclaimer, the term of this patent is extended or adjusted under 35 U.S.C. 154(b) by 267 days.

(21) Appl. No.: 10/758,836

(22) Filed: Jan. 16, 2004

(65) Prior Publication Data
US 2004/0159773 A1   Aug. 19, 2004

Related U.S. Application Data

(63) Continuation-in-part of application No. 10/616,829, filed on Jul. 10, 2003, which is a continuation-in-part of application No. 10/189,326, filed on Jul. 2, 2002, which is a continuation-in-part of application No. 09/900,218, filed on Jul. 6, 2001, now Pat. No. 6,664,528.

(51) Int. Cl.
*H01L 27/00* (2006.01)
*H01J 3/14* (2006.01)

(52) U.S. Cl. .................. 250/208.1; 250/216
(58) Field of Classification Search ............ 250/208.1, 250/216; 359/9, 15
See application file for complete search history.

(56) References Cited

U.S. PATENT DOCUMENTS

| | | | |
|---|---|---|---|
| 4,750,022 A | 6/1988 | Araki | |
| 5,051,770 A | 9/1991 | Cornuejols | |
| H001060 H | 5/1992 | Lazich | |
| 5,198,653 A | 3/1993 | Shen et al. | |
| 5,204,770 A | 4/1993 | Kachru et al. | |
| 5,291,008 A | 3/1994 | Havens et al. | |
| 5,430,807 A | 7/1995 | Gravely | |
| 5,559,629 A | 9/1996 | Sheets et al. | |
| 5,710,430 A | 1/1998 | Nuss | |
| 5,719,620 A | 2/1998 | Allio | |
| 5,737,084 A | 4/1998 | Ishihara | |
| 5,757,425 A | 5/1998 | Barton et al. | |
| 5,798,519 A * | 8/1998 | Vock et al. | 250/206.1 |

(Continued)

OTHER PUBLICATIONS

International Search Report dated Nov. 12, 2002 in PCT Application No. PCT/US02/21392 filed Jul. 3, 2002.

(Continued)

*Primary Examiner*—Georgia Epps
*Assistant Examiner*—Brian Livedalen
(74) *Attorney, Agent, or Firm*—Amin & Turocy, LLP

(57) ABSTRACT

An imaging system, methodology, and various applications are provided to facilitate optical imaging performance. The system contains a sensor having one or more receptors and an image transfer medium to scale the sensor and receptors in accordance with resolvable characteristics of the medium, and as defined with certain ratios. A computer, memory, and/or display associated with the sensor provides storage and/or display of information relating to output from the receptors to produce and/or process an image, wherein a plurality of illumination sources can also be utilized in conjunction with the image transfer medium. The image transfer medium can be configured as a k-space filter that correlates projected receptor size to a diffraction-limited spot associated with the image transfer medium, wherein the projected receptor size can be unit-mapped within a certain ratio to the size of the diffraction-limited spot, both in the object plane.

23 Claims, 26 Drawing Sheets

U.S. PATENT DOCUMENTS

| | | | |
|---|---|---|---|
| 5,876,327 A | 3/1999 | Tsuyuki et al. | |
| 5,965,875 A * | 10/1999 | Merrill | 250/226 |
| 5,973,844 A | 10/1999 | Burger | |
| 6,005,916 A | 12/1999 | Johnson et al. | |
| 6,008,945 A | 12/1999 | Fergason | |
| 6,020,988 A | 2/2000 | Deliwala et al. | |
| 6,069,743 A * | 5/2000 | Nagata et al. | 359/687 |
| 6,078,390 A | 6/2000 | Bengtsson | |
| 6,088,097 A | 7/2000 | Uhl | |
| 6,124,974 A | 9/2000 | Burger | |
| 6,128,068 A | 10/2000 | Suzuki et al. | |
| 6,178,346 B1 | 1/2001 | Amundson et al. | |
| 6,195,213 B1 | 2/2001 | Omura et al. | |
| 6,198,147 B1 * | 3/2001 | Connolly | 257/461 |
| 6,248,988 B1 | 6/2001 | Krantz | |
| 6,249,360 B1 | 6/2001 | Pollard et al. | |
| 6,268,918 B1 | 7/2001 | Tanabe et al. | |
| 6,285,811 B1 | 9/2001 | Aggarwal et al. | |
| 6,344,893 B1 | 2/2002 | Mendlovic et al. | |
| 6,388,788 B1 * | 5/2002 | Harris et al. | 359/195 |
| 6,448,556 B1 | 9/2002 | Cowley et al. | |
| 2002/0110320 A1 | 8/2002 | Carlisle et al. | |
| 2002/0126591 A1 | 9/2002 | Kouichi et al. | |
| 2002/0162973 A1 | 11/2002 | Cordingley et al. | |

OTHER PUBLICATIONS

Melles Griot, Optical Systems, Machine Vision Product Guide, USA, 1998.

* cited by examiner

IMAGING SYSTEM AND METHODOLOGY

RELATED APPLICATIONS

This application is a continuation-in-part of U.S. patent application of Ser. No. 10/616,829 which was filed Jul. 10, 2003 entitled IMAGING SYSTEM, METHODOLOGY, AND APPLICATIONS EMPLOYING RECIPROCAL SPACE OPTICAL DESIGN, which is a continuation-in-part of U.S. patent application Ser. No. 10/189,326 which was filed Jul. 2, 2002 entitled IMAGING SYSTEM AND METHODOLOGY EMPLOYING RECIPROCAL SPACE OPTICAL DESIGN, which is a continuation-in-part of U.S. patent application Ser. No. 09/900,218, which was filed Jul. 6, 2001, now U.S. Pat. No. 6,664,528 entitled IMAGING SYSTEM AND METHODOLOGY EMPLOYING RECIPROCAL SPACE OPTICAL DESIGN, all of which are incorporated herein by reference.

TECHNICAL FIELD

The present invention relates generally to image and optical systems, and more particularly to a system and method to facilitate imaging performance via an image transfer medium that projects characteristics of a sensor to an object field of view.

BACKGROUND OF THE INVENTION

Microscopes facilitate creating a large image of a tiny object. Greater magnification can be achieved if the light from an object is made to pass through two lenses compared to a simple microscope with one lens. A compound microscope has two or more converging lenses, placed in line with one another, so that both lenses refract the light in turn. The result is to produce an image that is magnified with improved quality in Resolved Magnification and other image parameters than either lens could alone. Light illuminating the object first passes through a short focal length lens or lens group, called the objective, and then travels on some distance before being passed through a longer focal length lens or lens group, called the eyepiece. A lens group is often simply referred to singularly as a lens. Usually these two lenses are held in paraxial relationship to one another, so that the axis of one lens is arranged to be in the same orientation as the axis of the second lens. It is the nature of the lenses, their properties, their relationship, and the relationship of the objective lens to the object that determines how a highly magnified image is produced in the eye of the observer.

The first lens or objective is usually a small lens with a very small focal length. A specimen or object is placed in the path of a light source with sufficient intensity to illuminate as desired. The objective lens is then lowered until the specimen is very close to, but not quite at the focal point of the lens. Light leaving the specimen and passing through the objective lens produces a real, inverted and magnified image behind the lens, in the microscope at a point generally referred to as the intermediate image plane. The second lens or eyepiece has a longer focal length and is placed in the microscope so that the image produced by the objective lens falls closer to the eyepiece than one focal length (that is, inside the focal point of the lens). The image from the objective lens now becomes the object for the eyepiece lens. As this object is inside one focal length, the second lens refracts the light in such a way as to produce a second image that is virtual, inverted and magnified. This is the final image seen by the eye of the observer.

Alternatively, common infinity space or infinity corrected design microscopes employ objective lenses with infinite conjugate properties such that the light leaving the objective is not focused, but is a flux of parallel rays which do not converge until after passing through a tube lens where the projected image is then located at the focal point of the eyepiece for magnification and observation. Many microscopes, such as the compound microscope described above, are designed to provide images of certain quality to the human eye through an eyepiece. Connecting a Machine Vision Sensor, such as a Charge Coupled Device (CCD) sensor, to the microscope so that an image may be viewed on a monitor presents difficulties. This is because the image quality provided by the sensor and viewed by a human eye decreases as compared to an image viewed by a human eye directly through an eyepiece. As a result, conventional optical systems for magnifying, observing, examining, and analyzing small items often require the careful attention of a technician monitoring the process through an eyepiece. It is for this reason, as well as others, that Machine-Vision or computer-based image displays from the aforementioned image sensor displayed on a monitor or other output display device are not of quality perceived by the human observer through the eyepiece.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The present invention relates to a system and methodology that facilitates imaging performance of optical imaging systems. In regard to several optical and/or imaging system parameters, many orders of performance enhancement can be realized over conventional systems (e.g., greater effective resolved magnification, larger working distances, increased absolute spatial resolution, increased spatial field of view, increased depth of field, Modulation Transfer Function of about 1, oil immersion objectives and eye pieces not required). This is achieved by adapting an image transfer medium (e.g., one or more lenses, fiber optical media, or other media) to a sensor having one or more receptors (e.g., photodetectors, pixels) such that the receptors of the sensor are effectively scaled (e.g., "mapped", "sized", "projected", "matched", "reduced") to occupy an object field of view at about the scale or size associated with a diffraction limited point or spot within the object field of view. Thus, a band-pass filtering of spatial frequencies in what is known as Fourier space or "k-space" is achieved such that the projected size (projection in a direction from the sensor toward object space) of the receptor is filled in k-space.

In other words, the image transfer medium is adapted, configured and/or selected such that a transform into k-space is achieved, wherein an a priori design determination causes k-space or band-pass frequencies of interest to be substantially preserved throughout and frequencies above and below the k-space frequencies to be mitigated. It is noted that the frequencies above and below the k-space frequencies tend to cause blurring and contrast reduction and are generally associated with conventional optical system designs which define intrinsic constraints on a Modulation Transfer Function and "optical noise". This further illustrates that the systems and methods of the present invention are in contravention or opposition to conventional geometric paraxial ray designs. Consequently, many known optical design limitations associated with conventional systems are mitigated by the present invention.

According to one aspect of the present invention, a "k-space" design, system and methodology is provided which defines a "unit-mapping" of the Modulation Transfer Function (MTF) of an object plane to image plane relationship. The k-space design projects image plane pixels or receptors forward to the object plane to promote an optimum theoretical relationship. This is defined by numeric ratios and sizes of projected image sensor receptors and projected object plane units (e.g., units defined by smallest resolvable points or spots in an optical or image transfer medium) that are matched according to the projected receptor size. The k-Space design defines "unit-mapping" or "unit-matching" acts as an effective "Intrinsic Spatial Filter" which implies that spectral components of both an object and an image in k-space (also referred to as "reciprocal-space") are substantially matched or quantized. Advantages provided by the k-space design result in a system and methodology capable of much higher effective resolved magnification with concomitantly related and much increased Field Of View, Depth Of Field, Absolute Spatial Resolution, and Working Distances utilizing dry objective lens imaging, for example, and without employing conventional oil immersion techniques having inherent intrinsic limitations to the aforementioned parameters.

One aspect of the present invention relates to an optical system that includes an optical sensor having an array of light receptors having a pixel size. A lens optically associated with the optical sensor is configured with optical parameters functionally related to the pixel size and a desired resolution of the optical system. As a result, the lens is operative to substantially map a portion of an object having the desired resolution along the optical path to an associated one of the light receptors.

Another aspect of the present invention relates to a method of designing an optical system. The method includes selecting a sensor with a plurality of light receptors having a pixel size and projected pixel size in the object plane. A desired minimum spot size resolution is selected for the system and a lens configured or an extant lens selected with optical parameters based on the projected pixel size and the desired minimum spot size is provided so as to map the plurality of light receptors to part of the image according to the desired resolution. The mapping can be quantified by ratios between projected pixel size and diffraction spot size.

The following description and the annexed drawings set forth in detail certain illustrative aspects of the invention. These aspects are indicative, however, of but a few of the various ways in which the principles of the invention may be employed and the present invention is intended to include all such aspects and their equivalents. Other advantages and novel features of the invention will become apparent from the following detailed description of the invention when considered in conjunction with the drawings.

DETAILED DESCRIPTION OF THE INVENTION

Figure 1:
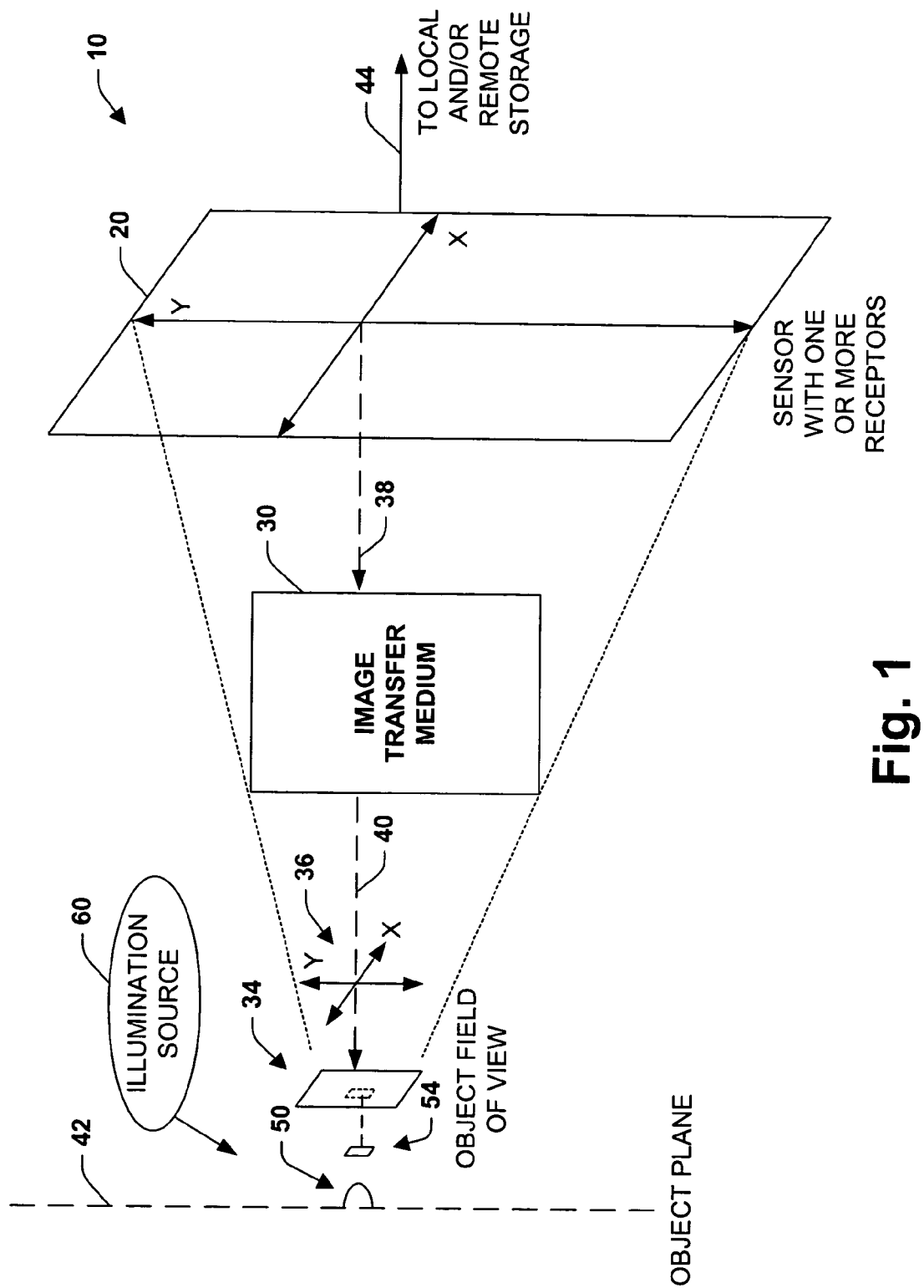
FIG. 1 is a schematic block diagram illustrating an imaging system in accordance with an aspect of the present invention.

The present invention relates to an optical and/or imaging system and methodology. According to one aspect of the present invention, a k-space filter is provided that can be configured from an image transfer medium such as optical media that correlates image sensor receptors to an optical or image transfer medium. A variety of illumination sources can also be employed to achieve one or more operational goals and for versatility of application. The k-space design of the imaging system of the present invention promotes capture and analysis (e.g., automated and/or manual) of images having a high Field Of View (FOV) at substantially high Effective Resolved Magnification as compared to conventional systems. This can include employing a small Numerical Aperture (NA) associated with lower magnification objective lenses to achieve very high Effective Resolved Magnification. As a consequence, images having a substantially large Depth Of Field (DOF) at very high Effective Resolved Magnification are also realized. The k-space design also facilitates employment of homogeneous illumination sources that are substantially insensitive to changes in position, thereby improving methods of examination and analysis.

According to another aspect of the present invention, an objective lens to object distance (e.g., Working Distance) can be maintained in operation at low and high power effective resolved magnification imaging, wherein typical spacing can be achieved at about 0.1 mm or more and about 20 mm or less, as opposed to conventional microscopic systems which can require significantly smaller (as small as 0.01 mm) object to objective lens distances for comparable (e.g., similar order of magnitude) Effective Resolved Magnification values. In another aspect, the Working Distance is about 0.5 mm or more and about 10 mm or less. It is to be appreciated that the present invention is not limited to operating at the above working distances. In many instances the above working distances are employed, however, in some instances, smaller or larger distances are employed. It is further noted that oil immersion or other Index of Refraction matching media or fluids for objective lenses are generally not required (e.g., substantially no improvement to be gained) at one or more effective image magnification levels of the present invention yet, still exceeding effective resolved magnification levels achievable in conventional microscopic optical design variations including systems employing "infinity-corrected" objective lenses.

The k-space design of the present invention defines that a small "Blur Circle" or diffraction limited point/spot at the object plane is determined by parameters of the design to match projected image sensor receptors or projected pixels in the object plane with a ratio defined correspondence by "unit-mapping" of object and image spaces for associated object and image fields. This enables the improved performance and capabilities of the present invention. One possible theory of the k-space design results from the mathematical concept that since the Fourier Transform of both an object and an image is formed in k-space (also called "reciprocal space"), the sensor is mapped to the object plane in k-space via optical design techniques and component placement in accordance with the present invention. It is to be appreciated that a plurality of other transforms or models can be utilized to configure and/or select one or more components in accordance with the present invention. For example, wavelet transforms, Laplace (s-transforms), z-transforms as well as other transforms can be similarly employed.

The k-space design methodology is unlike conventional optical systems designed according to geometric, paraxial ray-trace and optimization theory, since the k-space optimization facilitates that the spectral components of the object (e.g., tissue sample, particle, semiconductor) and the image are the same in k-space, and thus quantized. Therefore, there are substantially no inherent limitations imposed on a Modulation Transfer Function (MTF) describing contrast versus resolution and absolute spatial resolution in the present invention. Quantization, for example, in k-space yields a substantially unitary Modulation Transfer Function not realized by conventional systems. It is noted that high MTF, Spatial Resolution, and effective resolved image magnification can be achieved with much lower magnification objective lenses with desirable lower Numerical Apertures (e.g., generally less than about 50× with a numerical aperture of generally less than about 0.7) through "unit-mapping" of projected pixels in an "Intrinsic Spatial Filter" provided by the k-space design.

If desired, "infinity-corrected" objectives can be employed with associated optical component and illumination, as well as spectrum varying components, polarization varying components, and/or contrast or phase varying components. These components can be included in an optical path-length between an objective and the image lens within an "infinity space". Optical system accessories and variations can thus be positioned as interchangeable modules in this geometry. The k-space design, in contrast to conventional microscopic imagers that utilize "infinity-corrected" objectives, enables the maximum optimization of the infinity space geometry by the "unit-mapping" concept. This implies that there is generally no specific limit to the number of additional components that can be inserted in the "infinity space" geometry as in conventional microscopic systems that typically specify no more than 2 additional components without optical correction.

The present invention also enables a "base-module" design that can be configured and reconfigured in operation for a plurality of different applications if necessary to employ transmissive and/or reflected illumination, if desired. This includes substantially all typical machine vision illumination schemes (e.g., darkfield, brightfield, phase-contrast), and other microscopic transmissive techniques (Kohler, Abbe), in substantially any offset and can include Epi-illumination—and variants thereof. The systems of the present invention can be employed in a plurality of opto-mechanical designs that are robust since the k-space design is substantially not sensitive to environmental and mechanical vibration and thus generally does not require heavy structural mechanical design and isolation from vibration associated with conventional microscopic imaging instruments. Other features can include digital image processing, if desired, along with storage (e.g., local database, image data transmissions to remote computers for storage/analysis) and display of the images produced in accordance with the present invention (e.g., computer display, printer, film, and other output media). Remote signal processing of image data can be provided, along with communication and display of the image data via associated data packets that are communicated over a network or other medium, for example.

Moreover, images that are created in accordance with the present invention can be stored and/or transmitted with other digital information (e.g., audio data, other images, medical histories, product information, analysis information, and so forth). For example, an image may have associated voice-encoded data describing one or more aspects of the image or images contained as part of a data package that can be stored locally and/or transmitted across a network for remote storage and/or further analysis. In one specific example, an image created in accordance with the present invention can be transmitted to a remote location, wherein the image is further analyzed (e.g., medical or product specialist analyzes received image on a computer or image display). After analysis, a voice encoding or related data is appended or encoded with the received image and then transmitted back to the originating location (or other location), wherein the image and resultant encoded analysis can be reviewed. As can be appreciated, substantially any type of digital information can be stored and/or transmitted with images that are created in accordance with the present invention.

Also, as will be apparent from the following description, the present invention can be economically implemented in a plurality of various packages including integrated imaging/computing systems that are employed to analyze various samples. Such systems include handheld devices, notebook computers, laptops, personal digital assistants, and so forth that are adapted with the imaging concepts described herein.

Referring initially to FIG. 1, an imaging system 10 is illustrated in accordance with an aspect of the present invention. The imaging system 10 includes a sensor 20 having one or more receptors such as pixels or discrete light detectors (See e.g., illustrated below in FIG. 3) operably associated with an image transfer medium 30. The image transfer medium 30 is adapted or configured to scale the proportions of the sensor 20 at an image plane established by the position of the sensor 20 to an object field of view illustrated at reference numeral 34. A planar reference 36 of X and Y coordinates is provided to illustrate the scaling or reduction of the apparent or virtual size of the sensor 20 to the object field of view 34. Direction arrows 38 and 40 illustrate the direction of reduction of the apparent size of the sensor 20 toward the object field of view 34.

The object field of view 34 established by the image transfer medium 30 is related to the position of an object plane 42 that includes one or more items under microscopic examination (not shown). It is noted that the sensor 20 can be substantially any size, shape and/or technology (e.g., digital sensor, analog sensor, Charge Coupled Device (CCD) sensor, CMOS sensor, Charge Injection Device (CID) sensor, an array sensor, a linear scan sensor) including one or more receptors of various sizes and shapes, the one or more receptors being similarly sized or proportioned on a respective sensor to be responsive to light (e.g., visible, non-visible, "light", "radiation", or other such "visible" or "invisible" or "non-visible" hereafter meaning radiation of some desired wavelength optically directed. That is: radiation of any particular wavelength whose optical path, direction, and/or path length is altered by means of an optical medium, surface, material, component, or components, or other such means suitable to radiation of that wavelength in the configuration or configurations pertaining to the direction of such radiation to achieve the desired characteristics in accordance with the present invention) received from the items under examination in the object field of view 34.

As light is received from the object field of view 34, the sensor 20 provides an output 44 that can be directed to a local or remote storage such as a memory (not shown) and displayed from the memory via a computer and associated display, for example, without substantially any intervening digital processing (e.g., straight bit map from sensor memory to display), if desired. It is noted that local or remote signal processing of the image data received from the sensor 20 can also occur. For example, the output 44 can be converted to electronic data packets and transmitted to a remote system over a network and/or via wireless transmissions systems and protocols for further analysis and/or display. Similarly, the output 44 can be stored in a local computer memory before being transmitted to a subsequent computing system for further analysis and/or display.

The scaling provided by the image transfer medium 30 is determined by a novel k-space configuration or design within the medium that promotes predetermined k-space frequencies of interest and mitigates frequencies outside the predetermined frequencies. This has the effect of a band-pass filter of the spatial frequencies within the image transfer medium 30 and notably defines the imaging system 10 in terms of resolution rather than magnification. As will be described in more detail below, the resolution of the imaging system 10 determined by the k-space design promotes a plurality of features in a displayed or stored image such as having high effective resolved magnification, high absolute spatial resolution, large depth of field, larger working distances, and a unitary Modulation Transfer Function as well as other features.

In order to determine the k-space frequencies, a size or a "pitch" or spacing is determined between adjacent receptors on the sensor 20, the pitch related to the center-to-center distance of adjacent receptors and about the size or diameter of a single receptor. The pitch of the sensor 20 defines the Nyquist "cut-off" frequency band of the sensor. It is this frequency band that is promoted by the k-space design, whereas other frequencies are mitigated. In order to illustrate how scaling is determined in the imaging system 10, a small or diffraction limited spot or point 50 is illustrated at the object plane 42. The diffraction limited point 50 represents the smallest resolvable object determined by optical characteristics within the image transfer medium 30 and is described in more detail below. A scaled receptor 54, depicted in front of the field of view 34 for exemplary purposes, and having a size determined according to the pitch, for example, of the sensor 20, is matched or scaled to have a size ratio in the object field of view 34 as the diffraction limited point 50 which is a function of the resolvable characteristics of the image transfer medium 30.

In other words, the size of any given receptor at the sensor 20 is effectively reduced in size via the image transfer medium 30 to have a size (or matched in size) within a ratio of the size of the diffraction limited point 50. This also has the effect of filling the object field of view 34 with substantially all of the receptors of the sensor 20, the respective receptors being suitably scaled to be similar in size to the diffraction limited point 50. As will be described in more detail below, the matching/mapping of sensor characteristics to the smallest resolvable object or point within the object field of view 34 defines the imaging system 10 in terms of absolute spatial resolution and thus, enhances the operating performance of the system.

An illumination source 60 can be provided with the present invention in order that photons from the source can be transmitted through and/or reflected from objects in the field of view 34 to enable activation of the receptors in the sensor 20. It is noted that the present invention can potentially be employed without an illumination source 60 if potential self-luminous objects (e.g., fluorescent or phosphorescent biological or organic material sample, metallurgical, mineral, and/or other inorganic material and so forth) emit enough radiation to activate the sensor 60. Light Emitting Diodes, however, provide an effective illumination source 60 in accordance with the present invention. Substantially any illumination source 60 can be applied including coherent and non-coherent sources, visible and non-visible wavelengths. However, for non-visible wavelength sources, the sensor 20 and if necessary, the optical media of the image transfer medium 30 would also be suitably adapted. For example, for an infrared or ultraviolet source, an infrared or ultraviolet sensor 20 and IR or UV suitable optical components in the image transfer medium 30 would be employed, respectively. Other illumination sources 60 can include wavelength-specific lighting, broadband lighting, continuous lighting, strobed lighting, Kohler illumination, Abbe illumination, phase-contrast illumination, dark-field illumination, brightfield illumination, and Epi illumination. Transmissive or reflective lighting techniques (e.g., specular and diffuse) can also be applied.

Figure 2:
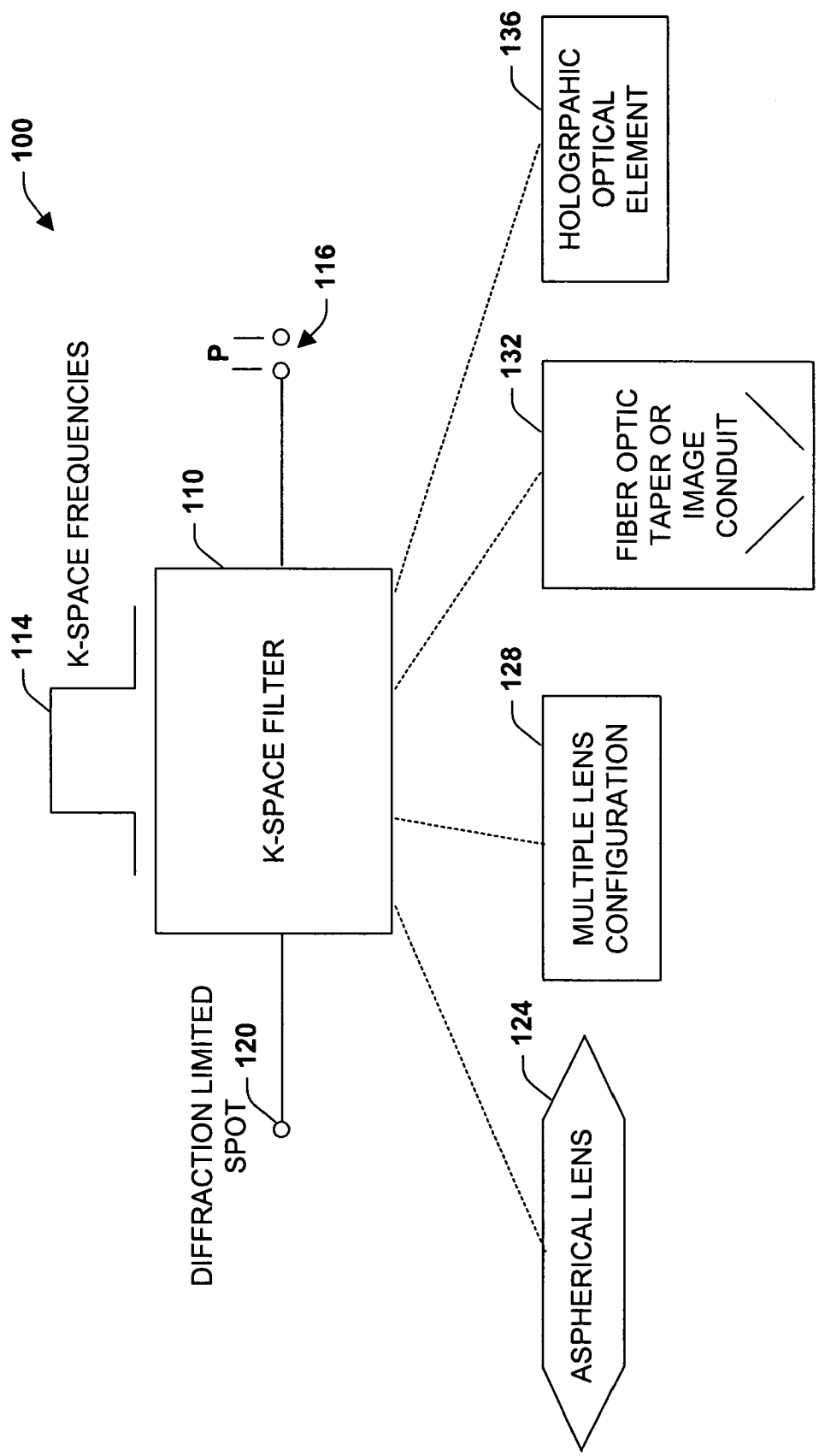
FIG. 2 is a diagram illustrating a k-space system design in accordance with an aspect of the present invention.

Referring now to FIG. 2, a system 100 illustrates an image transfer medium in accordance with an aspect of the present invention. The image transfer medium 30 depicted in FIG. 1 can be provided according to the k-space design concepts described above and more particularly via a k-space filter 110 adapted, configured and/or selected to promote a band of predetermined k-space frequencies 114 and to mitigate frequencies outside of this band. This is achieved by, for example, determining a pitch "P"—which is the distance between adjacent receptors 116 in a sensor (not shown) and sizing optical media within the filter 110 such that the pitch "P" of the receptors 116 is matched in size with a diffraction-limited spot 120. other pixel size parameters may be employed. The diffraction-limited spot 120 can be determined from the optical characteristics of the media in the filter 110. For example, the Numerical Aperture of an optical medium such as a lens defines the smallest object or spot that can be resolved by the lens. The filter 110 performs a k-space transformation such that the size of the pixel is effectively matched, "unit-mapped", projected, correlated, and/or reduced to the size or scale of the diffraction limited spot 120, in accordance with ratios provided below.

It is to be appreciated that a plurality of optical configurations can be provided to achieve the k-space filter 110. One such configuration can be provided by an aspherical lens 124 adapted such to perform the k-space transformation and reduction from sensor space to object space. Yet another configuration can be provided by a multiple lens arrangement 128, wherein the lens combination is selected to provide the filtering and scaling. Still yet another configuration can employ a fiber optic taper 132 or image conduit, wherein multiple optical fibers or array of fibers are configured in a funnel-shape to perform the mapping of the sensor to the object field of view. It is noted that the fiber optic taper 132 is generally in physical contact between the sensor and the object under examination (e.g., contact with microscope slide). Another possible k-space filter 110 arrangement employs a holographic (or other diffractive or phase structure) optical element 136, wherein a substantially flat optical surface is configured via a hologram (or other diffractive or phase structure) (e.g., computer-generated, optically generated, and/or other method) to provide the mapping in accordance with the present invention.

The k-space optical design as enabled by the k-space filter 110 is based upon the "effective projected pixel size" of the sensor, which is a figure derived from following ("projecting") the physical size of the sensor array elements back through the optical system to the object plane. In this manner, conjugate planes and optical transform spaces are matched to the Nyquist cut-off of the effective receptor or pixel size. This maximizes the effective resolved image magnification and the Field Of View as well as the Depth Of Field and the Absolute Spatial Resolution. Thus, a novel application of optical theory is provided that does not rely on conventional geometric optical design parameters of paraxial ray-tracing which govern conventional optics and imaging combinations. This can further be described in the following manner.

A Fourier transform of an object and an image is formed (by an optical system) in k-space (also referred to as "reciprocal-space"). It is this transform that is operated on for image optimization by the k-space design of the present invention. For example, the optical media employed in the present invention can be designed with standard, relatively non-expensive "off-the-shelf" components having a configuration which defines that the object and image space are "unit-mapped" or "unit-matched" for substantially all image and object fields. A small Blur-circle or diffraction-limited spot 120 at the object plane is defined by the design to match the projected pixel sizes in the object plane with ratios described below and thus the Fourier transforms of pixelated arrays can be matched. This implies that, optically by design, the Blur-circle is scaled to the projected size of the receptor or to the projected pixel size. The present invention is defined such that it constructs an Intrinsic Spatial Filter such as the k-space filter 110. Such a design definition and implementation enables the spectral components of both the object and the image in k-space to be about the same or quantized. This also defines that the Modulation Transfer Function (MTF) (the comparison of contrast to spatial resolution) of the sensor is at least substantially matched to the MTF of the object Plane.

Figure 3:
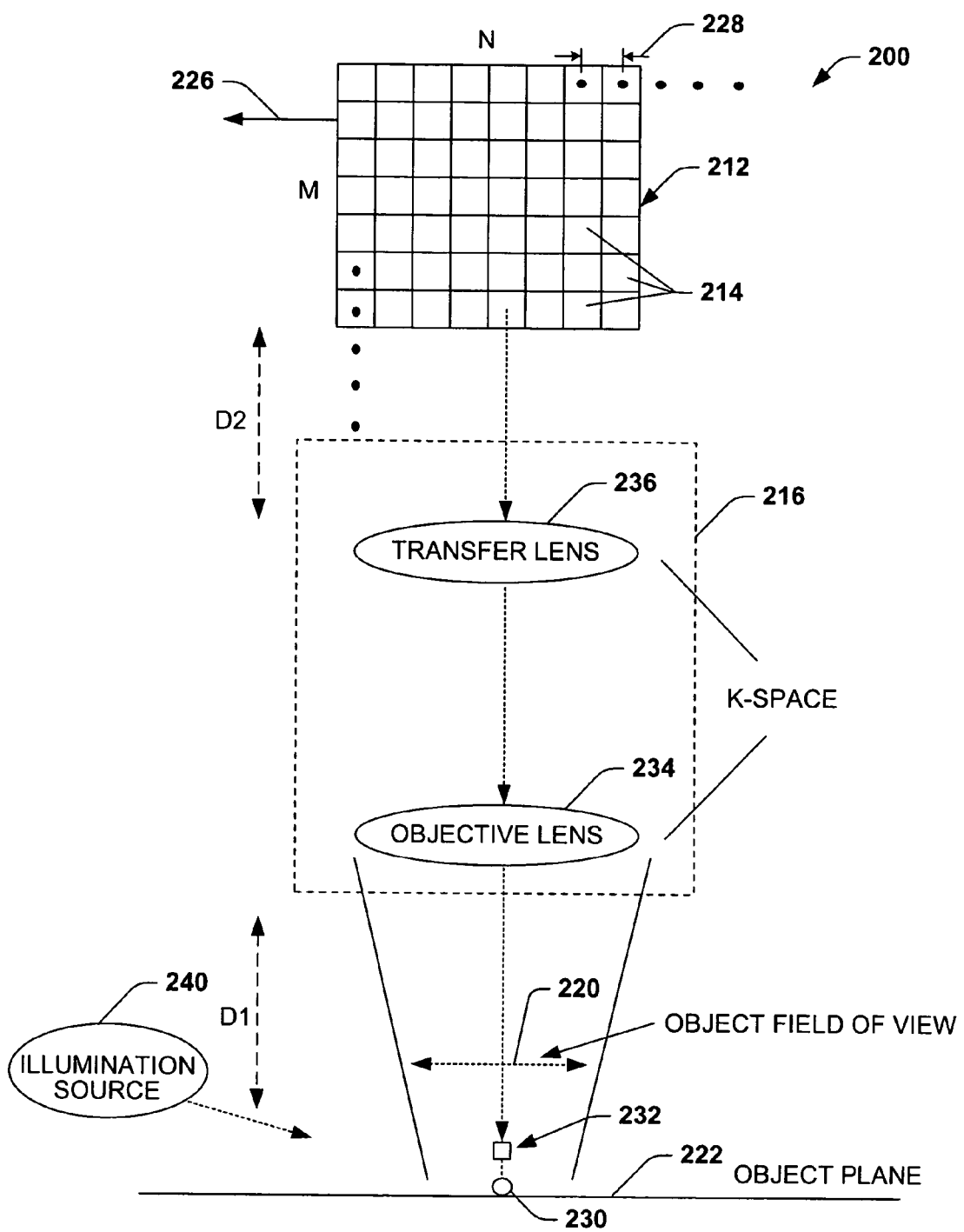
FIG. 3 is a diagram of an exemplary system illustrating sensor receptor matching in accordance with an aspect of the present invention.

FIG. 3 illustrates an optical system 200 in accordance with an aspect of the present invention. The system 200 includes a sensor 212 having a plurality of receptors or sensor pixels 214. For example, the sensor 212 is an M by N array of sensor pixels 214, having M rows and N columns (e.g., 640×480, 512×512, 1280×1024, 2268×1536, 1420×1064, and so forth), M and N being integers respectively. Although a rectangular sensor 212 having generally square pixels is depicted, it is to be understood and appreciated that the sensor can be substantially any shape (e.g., circular, elliptical, hexagonal, rectangular, and so forth). It is to be further appreciated that respective pixels 214 within the array can also be substantially any shape or size, the pixels in any given array 212 being similarly sized and shaped in accordance with an aspect of the present invention.

The sensor 212 can be substantially any technology (e.g., digital sensor, analog sensor, Charge Coupled Device (CCD) sensor, CMOS sensor, Charge Injection Device (CID) sensor, an array sensor, a linear scan sensor) including one or more receptors (or pixels) 214. According to one aspect of the present invention, each of the pixels 214 is similarly sized or proportioned and responsive to light (e.g., visible, non-visible) received from the items under examination, as described herein.

The sensor 212 is associated with a lens network 216, which is configured based on performance requirements of the optical system and the pitch size of sensor 212. The lens network 216 is operative to scale (or project) proportions (e.g., pixels 214) of the sensor 212 at an image plane established by the position of the sensor 212 to an object field of view 220 in accordance with an aspect of the present invention. The object field of view 220 is related to the position of an object plane 222 that includes one or more items (not shown) under examination.

Departing from the specifics of FIG. 3, the most common pixel or photodetector shapes are squares and rectangles. However, the pixels can have any shape so long as it retains its function. Additional shapes of pixels include hexagons, octagons, and other polygons, circles, ovals, ellipses, and the like. The size of the pixels typically varies from sensor to sensor.

There are a number of ways in which to measure pixel size. Typically, when not specified otherwise, pixel size is represented by pixel pitch, which the distance between the centers of adjacent pixels. Pixel size can be represented by area (surface area of the top surface or light receiving/detecting surface of a pixel), pixel length, pixel width, pixel diameter, and the like. In the case of stacked pixels, pixel size is determined based on a stack to stack basis. If pixels in a stack are of different sizes, then either the average of the different sizes, the largest of the different sizes, or the smallest of the different sizes is used to determine pixel size. This is because, when compared to the diffraction limited spot size in the object plane, it is the projected pixel size in the object plane that is employed.

In one aspect of the invention, the pixel size is one of a pixel pitch (for any pixels), pixel length (for square pixels), and pixel width (for rectangular pixels), that is about 0.1 microns or more and about 20 microns or less. In another aspect of the invention, the pixel size is one of a pixel pitch (for any pixels), pixel length (for square pixels), and pixel width (for rectangular pixels), that is about 0.25 microns or more and about 15 microns or less. In yet another aspect of the invention, the pixel size is one of a pixel pitch (for any pixels), pixel length (for square or rectangular pixels), and pixel width (for square or rectangular pixels), that is about 0.5 microns or more and about 10 microns or less. In still yet another aspect of the invention, the pixel size is one of a pixel pitch (for any pixels), pixel length (for square or rectangular pixels), and pixel width (for square or rectangular pixels), that is about 4 microns or more and about 9 microns or less.

In one aspect of the invention, the pixel size is pixel area that is about 0.01 microns$^2$ or more and about 600 microns$^2$ or less. In another aspect of the invention, the pixel size is pixel area that is about 0.1 microns$^2$ or more and about 200 microns$^2$ or less. In yet another aspect of the invention, the pixel size is pixel area that is about 0.5 microns$^2$ or more and about 100 microns$^2$ or less. In still yet another aspect of the invention, the pixel size is pixel area that is about 1 microns$^2$ or more and about 50 microns$^2$ or less.

In one aspect of the invention, the projected pixel size in the object plane is one of a projected pixel pitch (for any pixels), projected pixel length (for square pixels), and projected pixel width (for rectangular pixels), that is about 0.01 microns or more and about 20 microns or less. In another aspect of the invention, the projected pixel size in the object plane is one of a projected pixel pitch (for any pixels), projected pixel length (for square pixels), and projected pixel width (for rectangular pixels), that is about 0.05 microns or more and about 15 microns or less. In yet another aspect of the invention, the projected pixel size in the object plane is one of a projected pixel pitch (for any pixels), projected pixel length (for square pixels), and projected pixel width (for rectangular pixels), that is about 0.1 microns or more and about 10 microns or less. In still yet another aspect of the invention, the projected pixel size in the object plane is one of a projected pixel pitch (for any pixels), projected pixel length (for square pixels), and projected pixel width (for rectangular pixels), that is about 0.5 microns or more and about 5 microns or less.

In one aspect of the invention, the projected pixel size is projected pixel area that is about 0.0003 microns$^2$ or more and about 600 microns$^2$ or less. In another aspect of the invention, the projected pixel size is projected pixel area that is about 0.001 microns$^2$ or more and about 200 microns$^2$ or less. In yet another aspect of the invention, the projected pixel size is projected pixel area that is about 0.01 microns$^2$ or more and about 100 microns$^2$ or less. In still yet another aspect of the invention, the projected pixel size is projected pixel area that is about 0.1 microns$^2$ or more and about 50 microns$^2$ or less.

Specific examples of pixel parameters include a pixel pitch, pixel length, pixel width, and/or pixel diameter of about 20 microns, about 12.5 microns, about 12 microns, about 11 microns, about 10.8 microns, about 10 microns, about 9.9 microns, about 9.12 microns, about 8.8 microns, about 7.9 microns, about 7.8 microns, about 7.4 microns, about 5.4 microns, about 5 microns, about 4 microns, about 3.5 microns, and about 2.7 microns.

The sensors may have pixels where substantially all pixels have substantially the same shape and/or size. The sensors may also have pixels where one subset of pixels has a first shape and/or first size and a second subset of pixels has a second shape and/or second size. That is, the sensors may have pixels of at least two different shapes and/or at least two different sizes. Sensors with different sized pixels may have pixels that have different sizes, or may have certain groups of pixels that are combined to make pixels of apparent different sizes. Of course, suitable control circuitry can be employed to use image data from discrete sets of pixels.

Figure 25:
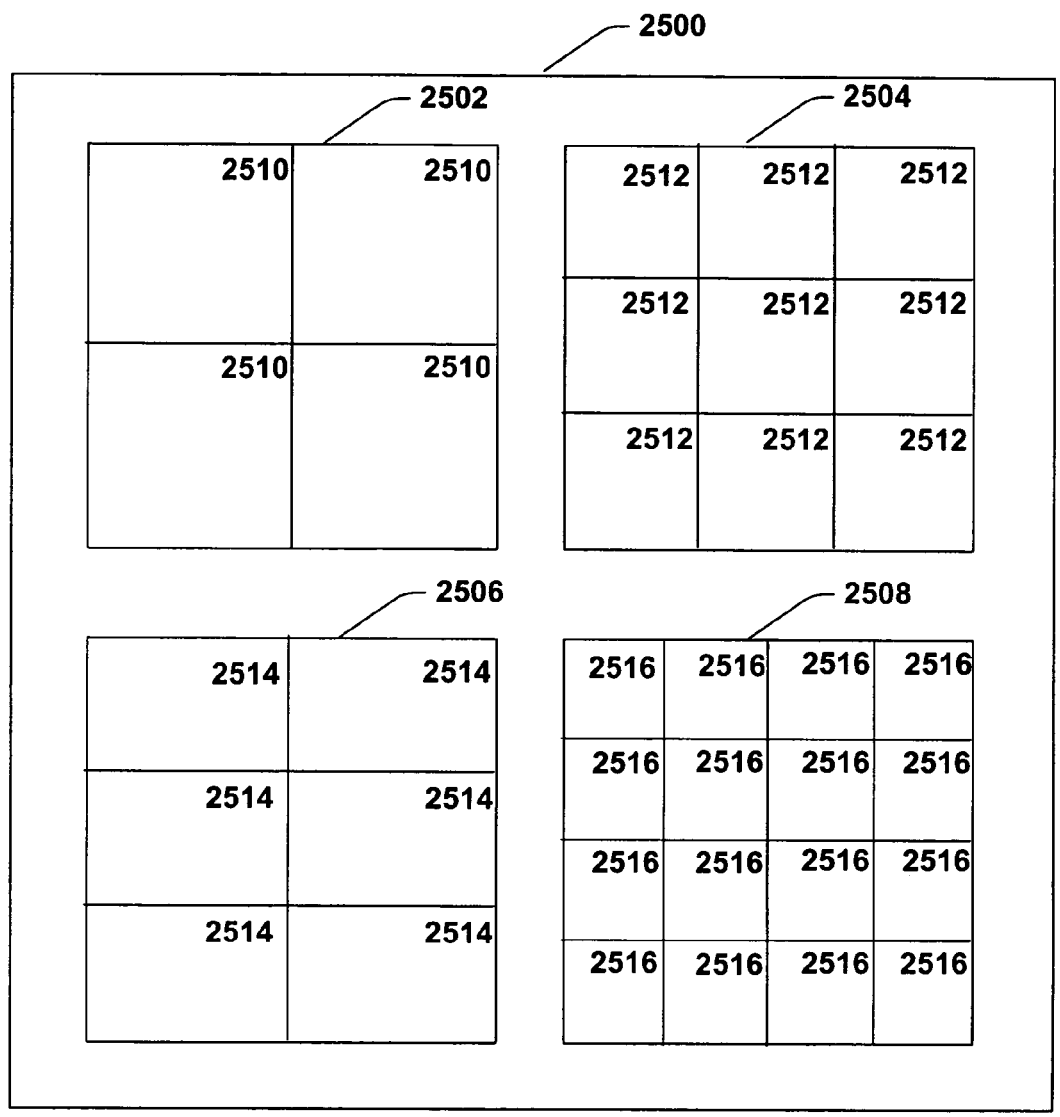
FIG. 25 is a top down view illustrating an exemplary sensor in accordance with an aspect of the present invention.

Referring to FIG. 25, a sensor 2500 is shown with four regions 2502, 2504, 2506, and 2508. Each of the four regions 2502, 2504, 2506, and 2508 has a discrete and different pixel size. That is, region 2502 has pixels 2510 of a first size and shape, region 2504 has pixels 2512 of a second size, region 2506 has pixels 2514 of a third size and second shape, region 2508 has pixels 2516 of a fourth size. Such a sensor can be employed in an imaging system that has a turret of four objective lenses, wherein each of the four objective lenses has a diffraction limited spot size in the object field of view matched with a respective one of the pixel sizes of the four pixel regions. The control circuitry can be employed to use data from a discrete set of pixels that have a size substantially matched with the size of the diffraction limited spot of one of the lenses.

The sensor may have a planar array of pixels where the pixels are oriented adjacent each other horizontally (unstacked), or an array of stacks of pixels may be provided on the sensor substrate. In the case of unstacked pixels, pixels having an ability to capture a discrete wavelength (or wavelength range) of light alternate throughout the sensor (to form, for example, a three colored checkerboard). In the case of stacked pixels (multilayered photodetectors), often three or four pixels are stacked, each having an ability to capture a discrete wavelength (or wavelength range) of light, such as red, green, and blue or cyan, magenta, and yellow in a three layered design and red, green, blue, and cyan in a four layered design. Also in the case of stacked pixels, each stack may contain pixels of the same size and/or shape or different sizes and/or shapes.

In embodiments where the sensor contains at least two arrays or areas having different pixel sizes, the arrays or areas may also be disposed so as to allow the direct indexing, or movement, or selection through optical path directing or mechanical directing, or other such means to configure any given discrete sensor array or area so that its entire discrete array or area or dimension is configured with the appropriate objective lens for mapping both the diffraction spot size to pixel size and the discrete sensor array or area to the entire object plane field of view in order to maximize the Absolute Spatial Resolution per pixel in the object plane. It is further defined that such groups, arrays, combinations, or other such assemblies comprising arrays of discrete sensor areas as described may be separated, individual sensor chips or integrated groupings on single substrates or mounts so disposed as to allow the selectability of the sensor group or array to be configured with the appropriate objective lens for mapping both the diffraction spot size to pixel size and the discrete sensor array or area to the object field of view. In other words, in order to maximize the Absolute Spatial Resolution of an image, the number of pixels projected within the object field of view is maximized, in addition to matching diffraction spot size in the object plane and pixel size.

Figure 26:
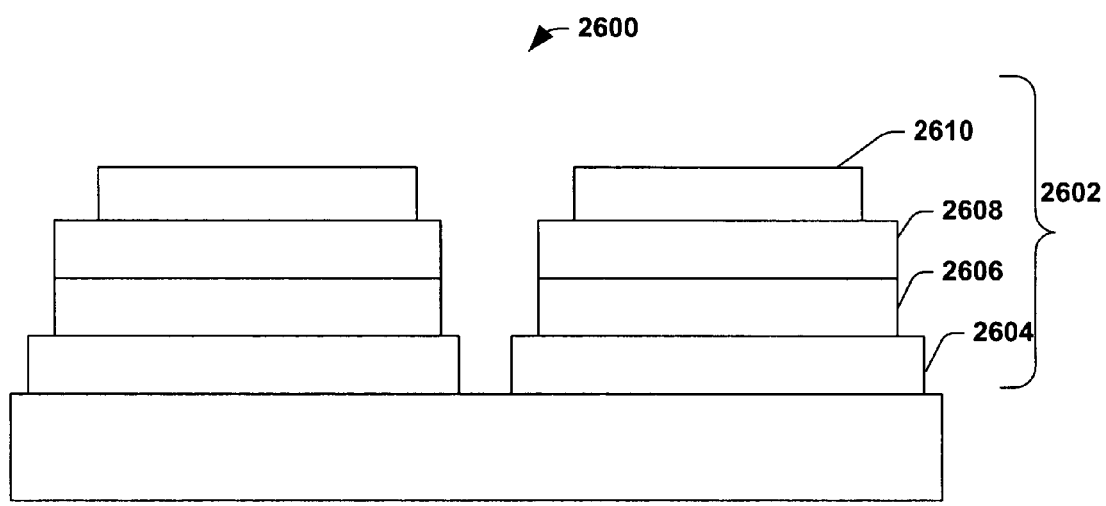
FIG. 26 is a cross sectional view illustrating an exemplary sensor in accordance with an aspect of the present invention.

Referring to FIG. 26, another sensor 2600 is shown having stacks 2602 of pixels. In this case, a stack 2602 of four pixels 2604, 2606, 2608, and 2610 (or four photodetectors that constitute a pixel stack 2602) is shown. When using a sensor having stacked pixels, the pixels or photodetectors of a stack may have the same or different sizes and/or shapes. FIG. 26 shows a stack 2602 having pixels 2604, 2606/2608, and 2610 having different sizes.

Examples of commercially available sensors, such as CCD and CMOS sensors, are those made by Foveon, Toshiba, Elisnet, Thomson, Sony, Samsung Semiconductor, Matsushita Electronics, Philips, Sharp, NEC, Motorola, Texas Instruments, EG&G Reticon, Kodak, Fairchild Imaging, CMOS Sensor Inc., Silicon Video Inc., National Semiconductor, Atmel, Exar, Agilent, Micron Technology, Mitsubishi, OmniVision, ST Microelectronics, and others.

Returning to FIG. 3, as the sensor 212 receives light from the object field of view 220, the sensor 212 provides an output 226 that can be directed to a local or remote storage such as a memory (not shown) and displayed from the memory via a computer and associated display, for example, without substantially any intervening digital processing (e.g., straight bit map from sensor memory to display), if desired. It is noted that local or remote signal processing of the image data received from the sensor 212 can also occur. For example, the output 226 can be converted to electronic data packets and transmitted to a remote system over a network for further analysis and/or display. Similarly, the output 226 can be stored in a local computer memory before being transmitted to a subsequent computing system for further analysis and/or display.

The scaling (or effective projecting) of pixels 214 provided by the lens network 216 is determined by a novel k-space configuration or design in accordance with an aspect of the present invention. The k-space design of the lens network 216 promotes predetermined k-space frequencies of interest and mitigates frequencies outside the predetermined frequency band. This has the effect of a band-pass filter of the spatial frequencies within the lens network 216 and notably defines the imaging system 200 in terms of resolution rather than magnification. As will be described below, the resolution of the imaging system 200 determined by the k-space design promotes a plurality of features in a displayed or stored image, such as having high "Effective Resolved Magnification" (a figure of merit described in following), with related high absolute spatial resolution, large depth of field, larger working distances, and a unitary Modulation Transfer Function as well as other features.

In order to determine the k-space frequencies, a pixel size is determined or a "pitch" or spacing 228 is determined between adjacent receptors 214 on the sensor 212. The pixel size (e.g., pixel pitch) can correspond to the center-to-center distance of adjacent receptors, indicated at 228, which is about the size or diameter of a single receptor when the sensor includes all equally sized pixels. The pitch 228 defines the Nyquist "cut-off" frequency band of the sensor 212. It is this frequency band that is promoted by the k-space design, whereas other frequencies are mitigated. In order to illustrate how scaling is determined in the imaging system 200, a point 230 of a desired smallest resolvable spot size is illustrated at the object plane 222, wherein the point is derived from resolvable characteristics of the lens network 216. The point 230, for example, can represent the smallest resolvable object determined by optical characteristics of the lens network 216. That is, the lens network is configured to have optical characteristics (e.g., magnification, numerical aperture) so that respective pixels 214 are matched or scaled to be within a ratio described below of the size in the object field of view 220 as the desired minimum resolvable spot size of the point 230. For purposes of illustration, a scaled receptor 232 is depicted in front of the field of view 220 as having a size determined according to the pitch 228 of the sensor 212, which is about the same as the point 230.

By way of illustration, the lens network 216 is designed to effectively reduce the size of each given receptor (e.g., pixel) 214 at the sensor 212 to be within the ratio (e.g., matched in size) of the size of the point 230, which is typically the minimum spot size resolvable by the system 210. It is to be understood and appreciated that the point 230 can be selected to a size representing the smallest resolvable object determined by optical characteristics within the lens network 216 as determined by diffraction rules (e.g., diffraction limited spot size). The lens network 216 thus can be designed to effectively scale each pixel 214 of the sensor 212 to any size that is equal to or greater than the diffraction limited size. For example, the resolvable spot size can be selected to provide for any desired image resolution that meets such criteria.

After the desired resolution (resolvable spot size) is selected, the lens network 216 is designed to provide the magnification to scale the pixels 214 to the object field of view 220 accordingly. This has the effect of filling the object field of view 220 with substantially all of the receptors of the sensor 212, the respective receptors being suitably scaled to be similar in size to the point 230, defined by ratios described below, which corresponds to the desired resolvable spot size. The matching/mapping of sensor characteristics to the desired (e.g., smallest) resolvable object or point 230 within the object field of view 220 defines the imaging system 200 in terms of absolute spatial resolution and enhances the operating performance of the system in accordance with an aspect of the present invention.

By way of further illustration, in order to provide unit-mapping according to this example, assume that the sensor array 212 provides a pixel pitch 228 of about 10 microns. The lens network 216 includes an objective lens 234 and a secondary lens 236. For example, the objective lens 234 can be set at infinite conjugate to the secondary lens 236, with the spacing between the objective and secondary lenses being flexible. The lenses 234 and 236 are related to each other so as to achieve a reduction from sensor space defined at the sensor array 220 to object space defined at the object plane 222. It is noted that substantially all of the pixels 214 are projected into the object field of view 220, which is defined by the objective lens 234. For example, the respective pixels 214 are scaled through the objective lens 234 to about the dimensions of the desired minimum resolvable spot size. In this example, the desired resolution at the image plane 222 is one micron. Thus, a magnification of ten times is operative to back project a ten micron pixel to the object plane 222 and reduce it to a size of one micron.

The reduction in size of the array 212 and associated pixels 214 can be achieved by selecting the transfer lens 236 to have a focal length "D2" (from the array 212 to the transfer lens 236) of about 150 millimeters and by selecting the objective lens to have a focal length "D1" (from the objective lens 236 to the object plane 222) of about 15 millimeters, for example. In this manner, the pixels 214 are effectively reduced in size to about 1 micron per pixel, thus matching the size of the of the desired resolvable spot 230 and filling the object field of view 220 with a "virtually-reduced" array of pixels. It is to be understood and appreciated that other arrangements of one or more lenses can be employed to provide the desired scaling.

In view of the foregoing description, those skilled in the art will understand and appreciate that the optical media (e.g., lens network 216) can be designed, in accordance with an aspect of the present invention, with standard, relatively inexpensive "off-the-shelf" components having a configuration that defines that the object and image space are "unit-mapped" or "unit-matched" for substantially all image and object fields. The lens network 216 and, in particular the objective lens 234, performs a Fourier transform of an object and an image in k-space (also referred to as "reciprocal-space"). It is this transform that is operated on for image optimization by the k-space design of the present invention.

A small Blur-circle or Airy disk at the object plane is defined by the design to match the projected pixels in the object plane within a certain ratio (size of projected pixel to size of the Airy disk) and thus the Fourier transforms of pixilated arrays can be matched. This implies that, optically by design, the Airy disk is scaled through the lens network 216 to be about the same size as the receptor or pixel size. As mentioned above, the lens network 216 is defined so as to construct an Intrinsic Spatial Filter (e.g., a k-space filter). Such a design definition and implementation enables the spectral components of both the object and the image in k-space to be about the same or quantized. This also defines that a Modulation Transfer Function (MTF) (the comparison of contrast to spatial resolution) of the sensor can be matched to the MTF of the object Plane in accordance with an aspect of the present invention.

A diffraction limited spot of an image transfer medium is the smallest resolvable object. The diffraction limited spot size is a parameter of an image transfer medium, such as a lens system. That is, the diffraction limited spot size varies from one lens to another. The diffraction limited spot is typically determined by the full width half maximum of the central peak of the gaussian diffraction spot. At least about 85% of the radiation energy exists in the central peak. Preferably, at least about 88% of the radiation energy exists in the central peak. Even more preferably, at least about 90% of the radiation energy exists in the central peak.

The diffraction limited spot size depends, in part, upon the wavelength of light used to capture an image. Any wavelength of light can be employed to form images in accordance with the invention. When using LEDs as an illumination source in the invention, it is possible to provide light for capturing images. In one exemplary aspect of the invention, when an LED is employed to provide illumination, at least about 75% of the light energy has a wavelength range from about 100 nm to about 10,000 nm. In another exemplary aspect of the invention, at least about 75% of the light energy has a wavelength range from about 100 nm to about 400 nm. In yet another exemplary aspect of the invention, at least about 75% of the light energy has a wavelength range from about 400 nm to about 700 nm. In still yet another exemplary aspect of the invention, at least about 75% of the light energy has a wavelength range from about 700 nm to about 2,000 nm. In another exemplary aspect of the invention, at least about 75% of the light energy has a wavelength range from about 250 nm to about 500 nm. In another exemplary aspect of the invention, at least about 75% of the light energy has a wavelength range from about 500 nm to about 1,200 nm. In yet another exemplary aspect of the invention, at least about 75% of the light energy has a wavelength range from about 350 nm to about 1,000 nm.

A diffraction spot exists on an object side of the image transfer medium and on an image side of the image transfer medium. Generally speaking, when referring herein to diffraction limited spot or diffraction limited spot size, diffraction spot or diffraction spot size, it is the diffraction limited spot on the object side and in the object plane unless specified otherwise.

The diffraction limited spot shape is commonly a circle. However, the diffraction limited spot is determined by the physical dimensions and/or properties of the lens. The diffraction limited spot can have any shape so long as it retains its characteristic function. Additional shapes of diffraction spots include ovals, ellipses, hexagons, octagons, and other polygons, and the like. The size of the diffraction spot typically varies from image transfer medium to image transfer medium. For example, size of the diffraction spot typically varies from lens to lens.

There are a number of ways in which to measure diffraction limited spot size. Typically, when not specified otherwise, diffraction spot size is represented by diameter, which the cross-section through the centerpoint of a circle. Diffraction limited spot size can alternatively be represented by area. In the case of a lens train, diffraction spot size is determined based on the combination of lenses. In the case of an ellipse, the diameter refers to a line through the middle, perpendicular to the line that includes the two foci.

In one aspect of the invention, the diffraction spot (in the object plane) has a diameter of about 0.01 microns or more and about 20 microns or less. In another aspect of the invention, the diffraction spot has a diameter of about 0.05 microns or more and about 15 microns or less. In yet another aspect of the invention, the diffraction spot has a diameter of about 0.1 microns or more and about 10 microns or less. In still yet another aspect of the invention, the diffraction spot has a diameter of about 0.5 microns or more and about 5 microns or less.

In one aspect of the invention, the diffraction spot size is diffraction spot area that is about 0.0003 microns$^2$ or more and about 600 microns$^2$ or less. In another aspect of the invention, the diffraction spot size is diffraction spot area that is about 0.001 microns$^2$ or more and about 200 microns$^2$ or less. In yet another aspect of the invention, the diffraction spot size is diffraction spot area that is about 0.01 microns$^2$ or more and about 100 microns$^2$ or less. In still yet another aspect of the invention, the diffraction spot size is diffraction spot area that is about 0.1 microns$^2$ or more and about 50 microns$^2$ or less.

In another aspect of the invention, the image transfer medium has a diffraction limited spot in an image plane having a diameter of about 0.1 microns or more and about 20 microns or less, and/or an area that is about 0.01 microns$^2$ or more and about 600 microns$^2$ or less. In yet another aspect of the invention, the image transfer medium has a diffraction limited spot in an image plane having a diameter of about 0.25 microns or more and about 15 microns or less, and/or an area that is about 0.1 microns$^2$ or more and about 200 microns$^2$ or less.

Examples of commercially available image transfer media, such as lenses, are those made by Bausch & Lomb, Canon, edmund Optics, Fujinon, Kahles, Kowa, Leica, Minolta, Minox, Meiji, Melles Griot, Mitutoyo, Nikon, Olympus, Pentax, Prior, Steiner, Swarovski, Swift, Unitron, Wild, Zeiss, and others. Any type of lens may be employed, so long as the diffraction limited spot in the object plane is matched with the pixel size of the sensor. Examples of lenses that may be employed in the image transfer system include Plan_Neofluar, Plan Fluotar, Planapochromat, Plan, Achroplan, Epiplans, Achromat, Planachromats, Semiapochromatic, Apochromatic, Planapochromat, and the like.

As illustrated in FIG. 3, k-space is defined as the region between the objective lens 234 and the secondary lens 236.

It is to be appreciated that substantially any optical media, lens type and/or lens combination that reduces, maps and/or projects the sensor array 212 to the object field of view 220 in accordance with unit or k-space mapping as described herein is within the scope of the present invention.

To illustrate the novelty of the exemplary lens/sensor combination depicted in FIG. 3, it is noted that conventional objective lenses, sized according to conventional geometric paraxial ray techniques, are generally sized according to the magnification, Numeric Aperture, focal length and other parameters provided by the objective. Thus, the objective lens would be sized with a greater focal length than subsequent lenses that approach or are closer to the sensor (or eyepiece in conventional microscope) in order to provide magnification of small objects. This can result in magnification of the small objects at the object plane being projected as a magnified image of the objects across "portions" of the sensor and results in known detail blur (e.g., Rayleigh diffraction and other limitations in the optics), empty magnification problems, and Nyquist aliasing among other problems at the sensor. The k-space design of the present invention operates in an alternative manner to conventional geometrical paraxial ray design principles. That is, the objective lens 234 and the secondary lens 236 operate to provide a reduction in size of the sensor array 212 to the object field of view 220, as demonstrated by the relationship of the lenses.

An illumination source 240 can be provided with the present invention in order that photons from that source can be transmitted through and/or reflected from objects in the field of view 234 to enable activation of the receptors in the sensor 212. It is noted that the present invention can potentially be employed without an illumination source 240 if potential self-luminous objects (e.g., objects or specimens with emissive characteristics as previously described) emit enough radiation to activate the sensor 212. Substantially any illumination source 240 can be applied including coherent and non-coherent sources, visible and non-visible wavelengths. However, for non-visible wavelength sources, the sensor 212 would also be suitably adapted. For example, for an infrared or ultraviolet source, an infrared or ultraviolet sensor 212 would be employed, respectively. Other suitable illumination sources 240 can include wavelength-specific lighting, broad-band lighting, continuous lighting, strobed lighting, Kohler illumination, Abbe illumination, phase-contrast illumination, darkfield illumination, brightfield illumination, Epi illumination, and the like. Transmissive or reflective (e.g., specular and diffuse) lighting techniques can also be applied.

Figure 4:
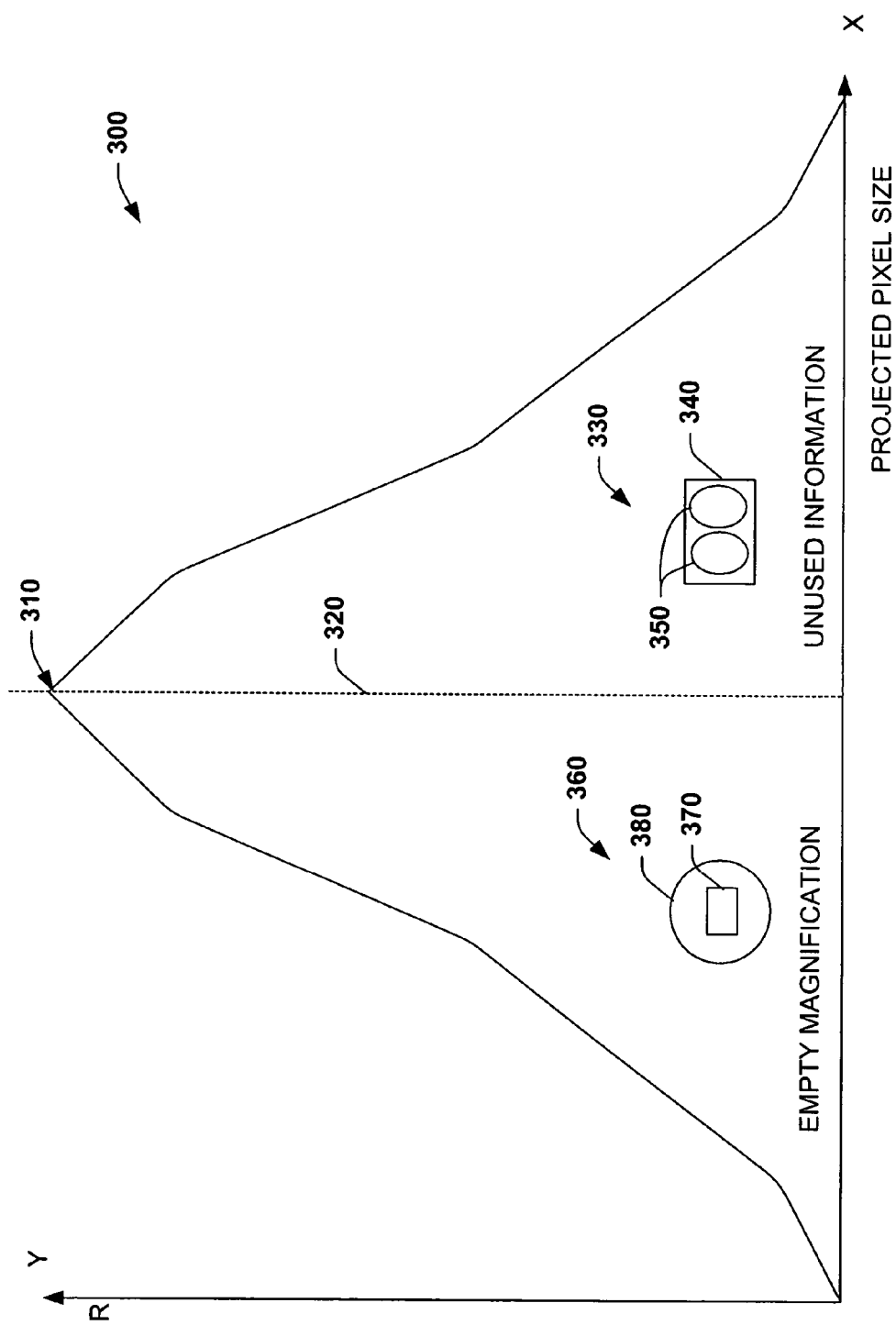
FIG. 4 is a graph illustrating sensor matching considerations in accordance with an aspect of the present invention.

FIG. 4 illustrates a graph 300 of mapping characteristics and comparison between projected pixel size on the X-axis and diffraction-limited spot resolution size "R" on the Y-axis. An apex 310 of the graph 300 corresponds to unit mapping between projected pixel size and the diffraction limited spot size, which represents an optimum relationship between a lens network and a sensor in accordance with the present invention.

It is to be appreciated that the objective lens 234 (FIG. 3) should generally not be selected such that the diffraction-limited size "R" of the smallest resolvable objects are substantially smaller than a projected pixel size. If so, "economic waste" can occur wherein more precise information is lost (e.g., selecting an object lens more expensive than required, such as having a higher numerical aperture). This is illustrated to the right of a dividing line 320 at reference 330 depicting a projected pixel 340 larger that two smaller diffraction spots 350. In contrast, where an objective is selected with diffraction-limited performance larger than the projected pixel size, blurring and empty magnification can occur. This is illustrated to the left of line 320 at reference numeral 360, wherein a projected pixel 370 is substantially smaller than a diffraction-limited object 380. It is to be appreciated, however, that even if substantially one-to-one correspondence is not achieved between projected pixel size and the diffraction-limited spot, a system can be configured with less than optimum matching (e.g., 0.1%, 1%, 2%, 5%, 20%, 95% down from the apex 310 on the graph 300 to the left or right of the line 320) and still provide suitable performance in accordance with an aspect of the present invention. Thus, less than optimal matching is intended to fall within the spirit and the scope of present invention.

It is further to be appreciated that the diameter of the lenses in the system as illustrated in FIG. 3, for example, should be sized such that when a Fourier Transform is performed from object space to sensor space, spatial frequencies of interest that are in the band pass region described above (e.g., frequencies utilized to define the size and shape of a pixel) are substantially not attenuated. This generally implies that larger diameter lenses (e.g., about 10 to 100 millimeters) should be selected to mitigate attenuation of the spatial frequencies of interest.

The projected pixel size of the sensor in the object plane and the diffraction limited spot size in the object plane of the image transfer medium are substantially matched or unit-mapped to provide at least one of improved absolute spatial resolution, improved depth of field, improved contrast, and improved field of view over digital images manufactured by a system where the pixel size of the sensor and the diffraction limited spot size in the object plane of the image transfer medium are not substantially matched or unit-mapped.

Matched or unit-mapped projected pixels and diffraction limited spots means that both the projected pixel area and diffraction limited spot size area in the object plane are about 0.0003 microns$^2$ or more and about 600 microns$^2$ or less. Alternatively or additionally, both the projected pixel projected pitch, projected pixel width, projected pixel length, or projected pixel diameter in the object plane and diffraction limited spot diameter in the object plane are about 0.01 microns or more and about 20 microns or less. The projected pixel size and the diffraction spot size determined by any measurement are suitably matched or unit-mapped to provide resolved images with generous field of view and depth of field.

In one aspect of the invention, the ratio of the projected pixel size to the diffraction spot size, both in the object plane and determined by pitch, length, width, or diameter, is between 1:2 and 2:1. In another aspect of the invention, the ratio of the projected pixel size to the diffraction spot size, both in the object plane and determined by pitch, length, width, or diameter, is from about 1:1.9 to about 1.9:1. In another aspect of the invention, the ratio of the projected pixel size to the diffraction spot size, both in the object plane and determined by pitch, length, width, or diameter, is from about 1:1.7 to about 1.7:1. In another aspect of the invention, the ratio of the projected pixel size to the diffraction spot size, both in the object plane and determined by pitch, length, width, or diameter, is from about 1:1.5 to about 1.5:1. In another aspect of the invention, the ratio of the projected pixel size to the diffraction spot size, both in the object plane and determined by pitch, length, width, or diameter, is from about 1:1.4 to about 1.4:1. In another aspect of the invention, the ratio of the projected pixel size to the diffraction spot size, both in the object plane and determined by pitch, length, width, or diameter, is from about 1:1.3 to about 1.3:1. In another aspect of the invention, the ratio of the projected pixel size to the diffraction spot size, both in the object plane and determined by pitch, length, width, or diameter, is from about 1:1.2 to about 1.2:1. In another aspect of the invention, the ratio of the projected pixel size to the diffraction spot size, both in the object plane and determined by pitch, length, width, or diameter, is from about 1:1.1 to about 1.1:1.

In one aspect of the invention, the ratio of the projected pixel size to the diffraction spot size, both in the object plane and determined by area, is from about 5:1 to about 1:12. In another aspect of the invention, the ratio of the projected pixel size to the diffraction spot size, both in the object plane and determined by area, is from about 4:1 to about 1:10. In yet another aspect of the invention, the ratio of the projected pixel size to the diffraction spot size, both in the object plane and determined by area, is from about 3.5:1 to about 1:8. In still yet another aspect of the invention, the ratio of the projected pixel size to the diffraction spot size, both in the object plane and determined by area, is from about 3:1 to about 1:6. In another aspect of the invention, the ratio of the projected pixel size to the diffraction spot size, both in the object plane and determined by area, is from about 2.5:1 to about 1:5. In another aspect of the invention, the ratio of the projected pixel size to the diffraction spot size, both in the object plane and determined by area, is from about 2:1 to about 1:4. In another aspect of the invention, the ratio of the projected pixel size to the diffraction spot size, both in the object plane and determined by area, is from about 1.5:1 to about 1:3. In another aspect of the invention, the ratio of the projected pixel size to the diffraction spot size, both in the object plane and determined by area, is from about 1.25:1 to about 1:2. In another aspect of the invention, the ratio of the projected pixel size to the diffraction spot size, both in the object plane and determined by area, is from about 1.1:1 to about 1:1.5.

Although not critical to the invention, in one aspect of the invention, the ratio of the pixel size to the diffraction limited spot in the image plane, both determined by pitch, length, width, or diameter, is from about 1:1.5 to about 1.5:1. In another aspect of the invention, the ratio of the pixel size to the diffraction limited spot in the image plane, both determined by pitch, length, width, or diameter, is from about 1:1.25 to about 1.25:1. In another aspect of the invention, the ratio of the pixel size to the diffraction limited spot in the image plane, both determined by pitch, length, width, or diameter, is from about 1:1.1 to about 1.1:1.

Figure 5:
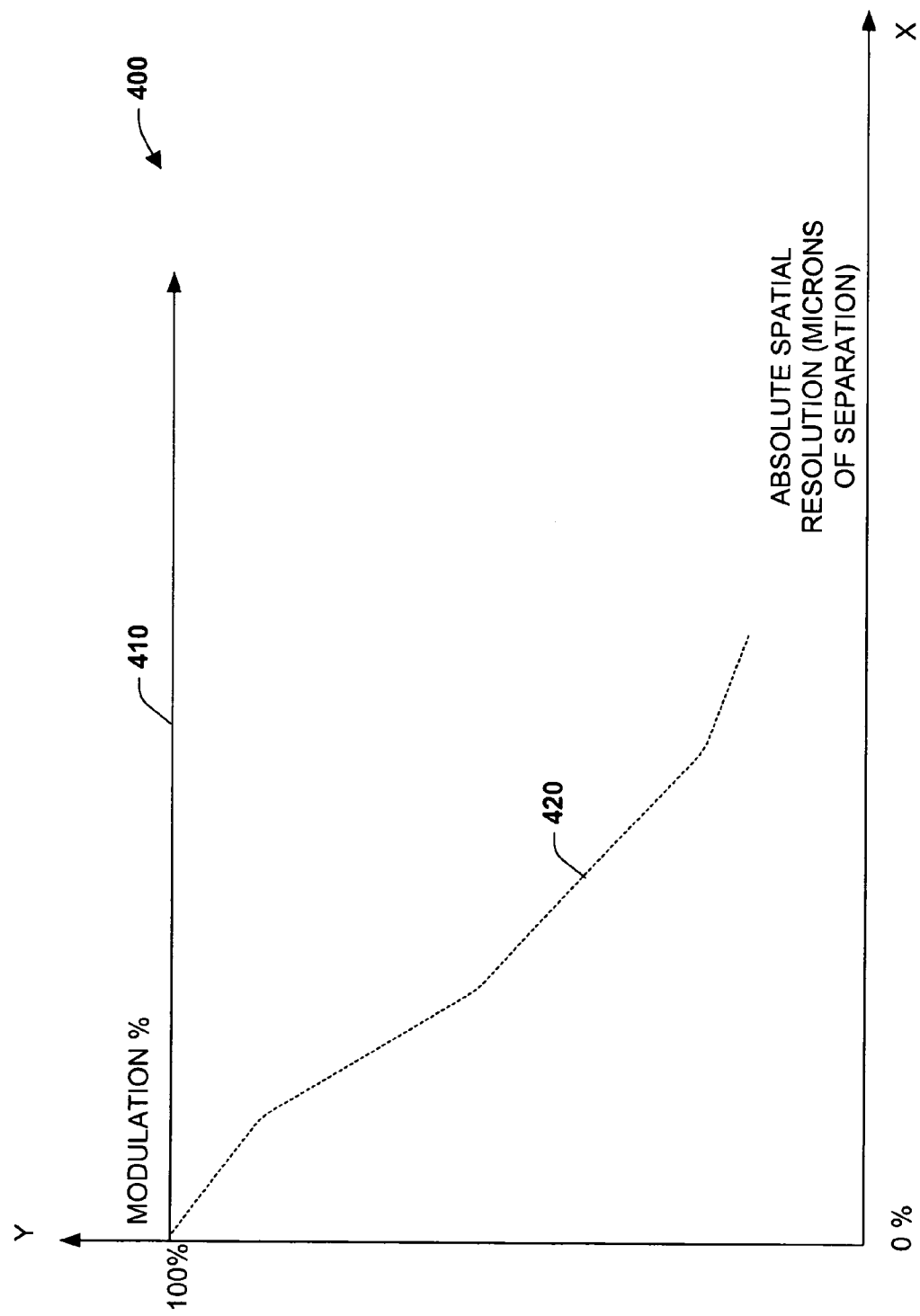
FIG. 5 is a graph illustrating a Modulation Transfer Function in accordance with an aspect of the present invention.

Referring now to FIG. 5, a Modulation Transfer function 400 is illustrated in accordance with the present invention. On a Y-axis, modulation percentage from 0 to 100% is illustrated defining percentage of contrast between black and white. On an X-axis, Absolution Spatial Resolution is illustrated in terms of microns of separation. A line 410 illustrates that modulation percentage remains substantially constant at about 100% over varying degrees of spatial resolution. Thus, the Modulation Transfer Function is about 1 for the present invention up to about a limit imposed by the signal to noise sensitivity of the sensor. For illustrative purposes, a conventional optics design Modulation Transfer Function is illustrated by line 420 which may be an exponential curve with generally asymptotic limits characterized by generally decreasing spatial resolution with decreasing modulation percentage (contrast).

Figure 6:
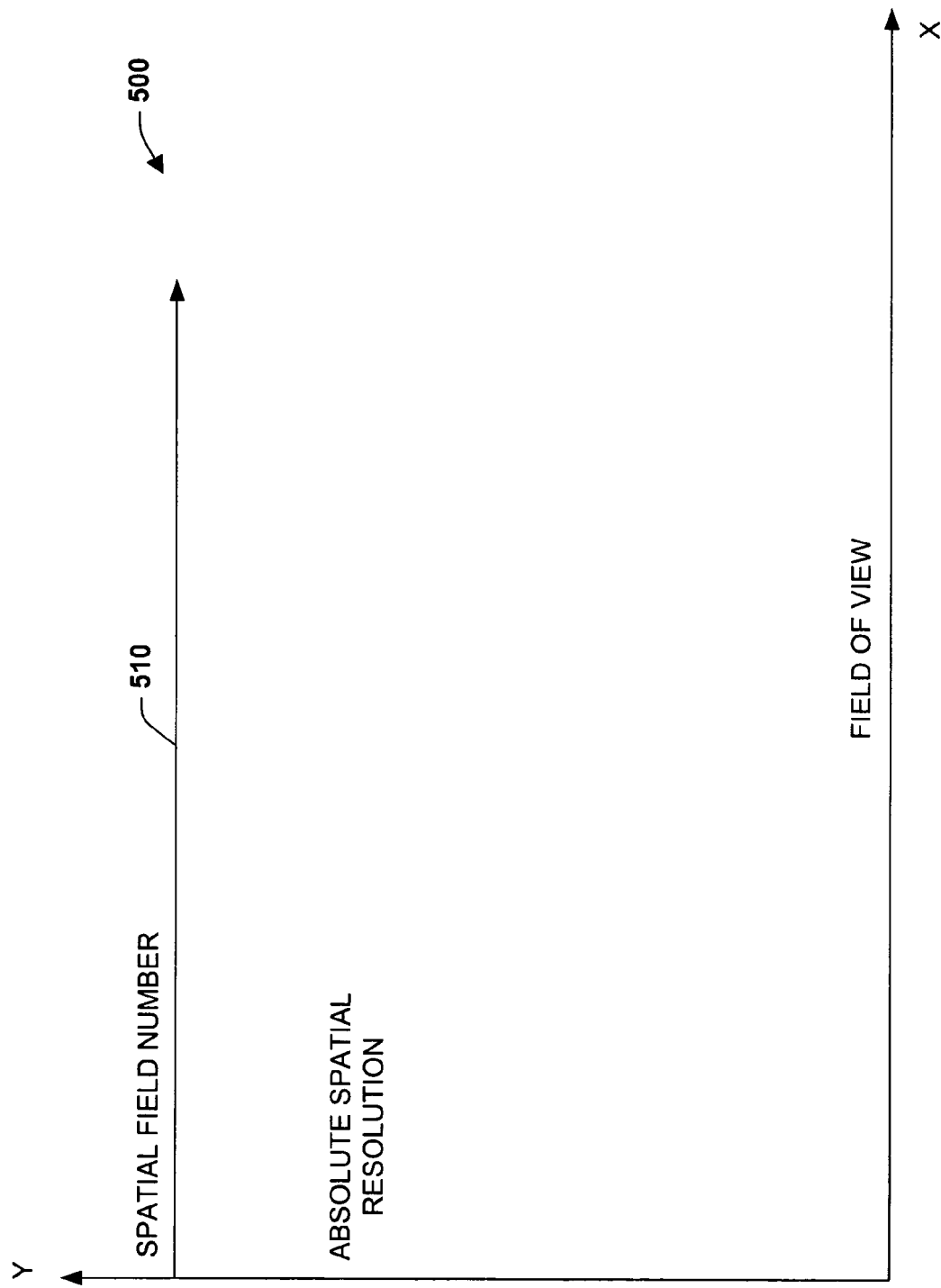
FIG. 6 is a graph illustrating a figure of merit relating to a Spatial Field Number in accordance with an aspect of the present invention.

FIG. 6 illustrates a quantifiable Figure of Merit (FOM) for the present invention defined as dependent on two primary factors: Absolute Spatial Resolution ($R_A$, in microns), depicted on the Y axis and the Field Of View (F, in microns) depicted on the X axis of a graph 500. A reasonable FOM called "Spatial Field Number" (S), can be expressed as the ratio of these two previous quantities, with higher values of S being desirable for imaging as follows:

$$S = F/R_A$$

A line 510 illustrates that the FOM remains substantially constant across the field of view and over different values of absolute spatial resolution which is an enhancement over conventional systems.

FIGS. 7, 8, 14, 15, 16, and 20 illustrate methodologies to facilitate imaging performance in accordance with the present invention. While, for purposes of simplicity of explanation, the methodologies may be shown and described as a series of acts, it is to be understood and appreciated that the present invention is not limited by the order of acts, as some acts may, in accordance with the present invention, occur in different orders and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the present invention.

Figure 7:
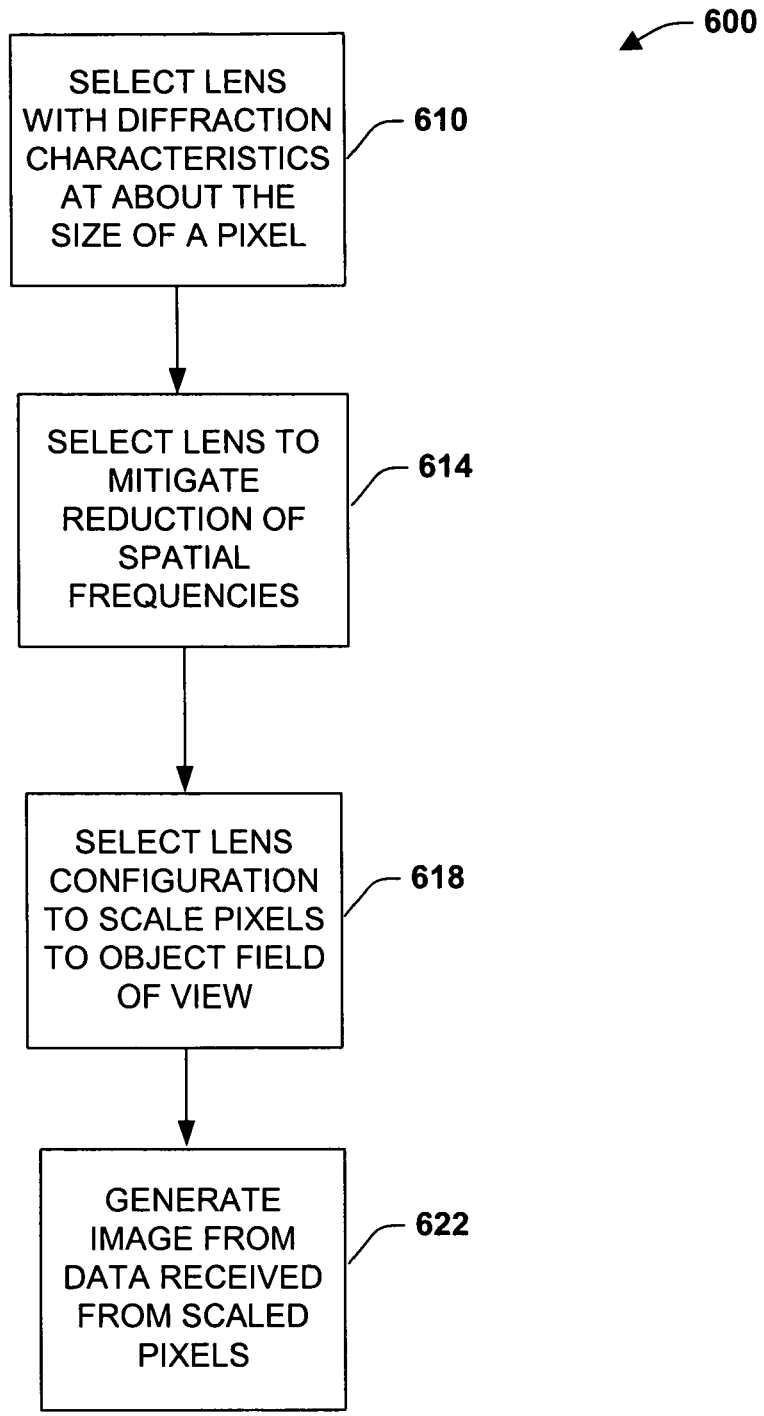
FIG. 7 is a flow diagram illustrating an imaging methodology in accordance with an aspect of the present invention.

Turning now to FIG. 7 and proceeding to 610, lenses are selected having diffraction-limited characteristics at about the same size of a pixel in order to provide unit-mapping and optimization of the k-space design. At 614, lens characteristics are also selected to mitigate reduction of spatial frequencies within k-space. As described above, this generally implies that larger diameter optics are selected in order to mitigate attenuation of desired k-space frequencies of interest. At 618, a lens configuration is selected such that pixels, having a pitch "P", at the image plane defined by the position of a sensor are scaled according to the pitch to an object field of view at about the size of a diffraction-limited spot (e.g., unit-mapped) within the object field of view. At 622, an image is generated by outputting data from a sensor for real-time monitoring and/or storing the data in memory for direct display to a computer display and/or subsequent local or remote image processing and/or analysis within the memory.

Figure 8:
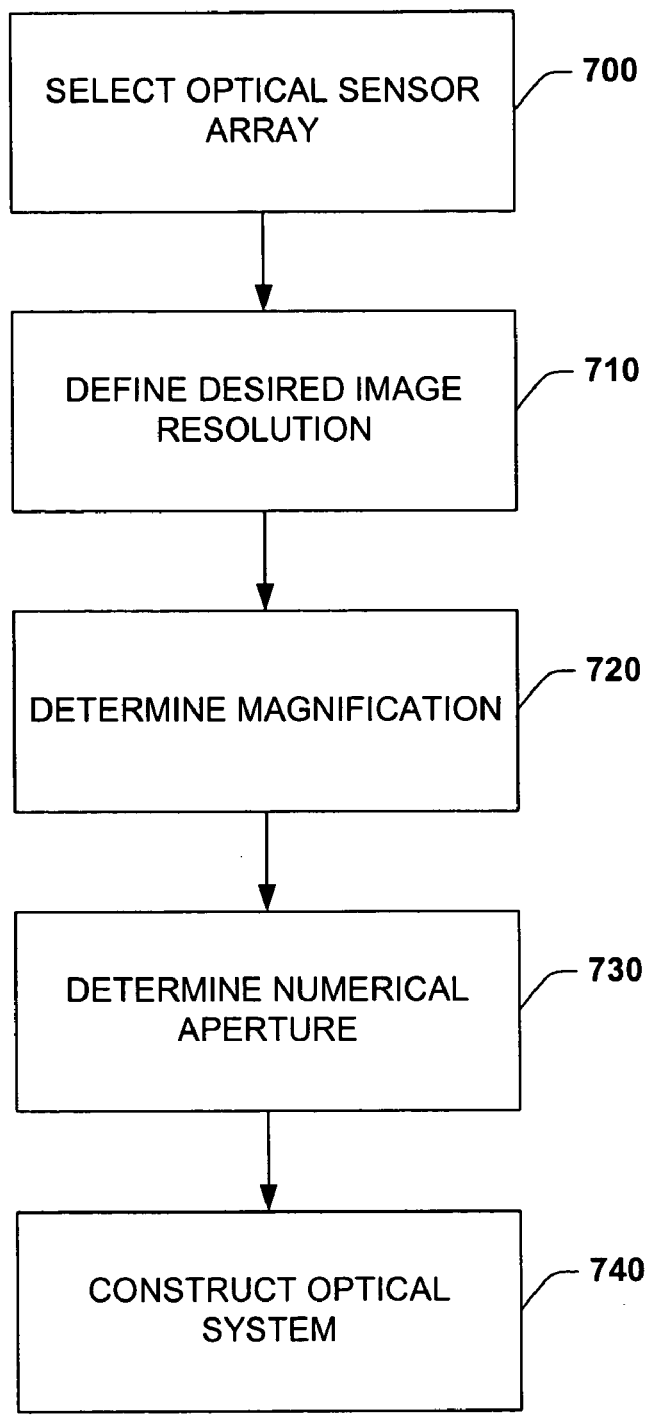
FIG. 8 is a flow diagram illustrating a methodology for selecting optical parameters in accordance with an aspect of the present invention.

FIG. 8 illustrates a methodology that can be employed to design an optical/imaging system in accordance with an aspect of the present invention. The methodology begins at 700 in which a suitable sensor array is chosen for the system. The sensor array includes a matrix of receptor pixels having a known pitch size, usually defined by the manufacturer. The sensor can be substantially any shape (e.g., rectangular, circular, square, triangular, and so forth). By way of illustration, assume that a sensor of 640×480 pixels having a pitch size of 10 µm is chosen. It is to be understood and appreciated that an optical system can be designed for any type and/or size of sensor array in accordance with an aspect of the present invention.

Next at 710, an image resolution is defined. The image resolution corresponds to the smallest desired resolvable spot size at the image plane. The image resolution can be defined based on the application(s) for which the optical system is being designed, such as any resolution that is greater than or equal to a smallest diffraction limited size. Thus, it is to be appreciated that resolution becomes a selectable design parameter that can be tailored to provide desired image resolution for virtually any type of application. In contrast, most conventional systems tend to limit resolution according to Rayleigh diffraction, which provides that intrinsic spatial resolution of the lenses cannot exceed limits of diffraction for a given wavelength.

After selecting a desired resolution (710), a suitable amount of magnification is determined at 720 to achieve such resolution. For example, the magnification is functionally related to the pixel pitch of the sensor array and the smallest resolvable spot size. The magnification (M) can be expressed as follows:

$$M = \frac{x}{y} \qquad \text{Eq. 1}$$

wherein:
x is the pixel size such as pixel pitch of the sensor array; and
y is the desired image resolution (minimum spot size).

So, for the above example where the pixel pitch is 10 µm and assuming a desired image resolution of 1 µm, Eq. 1 provides an optical system of power ten. That is, the lens system is configured to back-project each 10 µm pixel to the object plane and reduce respective pixels to the resolvable spot size of 1 micron.

The methodology of FIG. 8 also includes a determination of a Numerical Aperture at 730. The Numerical Aperture (NA) is determined according to well-established diffraction rules that relate NA of the objective lens to the minimum resolvable spot size determined at 710 for the optical system. By way of example, the calculation of NA can be based on the following equation:

$$NA = \frac{0.5 \times \lambda}{y} \qquad \text{Eq. 2}$$

where:
$\lambda$ is the wavelength of light being used in the optical system; and
y is the minimum spot size (e.g., determined at 710).

Continuing with the example in which the optical system has a resolved spot size of y=1 micron, and assuming a wavelength of about 500 nm (e.g., green light), a NA=0.25 satisfies Eq. 2. It is noted that relatively inexpensive commercially available objectives of power 10 provide numerical apertures of 0.25.

It is to be understood and appreciated that the relationship between NA, wavelength and resolution represented by Eq. 2 can be expressed in different ways according to various factors that account for the behavior of objectives and condensers. Thus, the determination at 730, in accordance with an aspect of the present invention, is not limited to any particular equation but instead simply obeys known general physical laws in which NA is functionally related to the wavelength and resolution. After the lens parameters have been designed according to the selected sensor (700), the corresponding optical components can be arranged to provide an optical system (740) in accordance with an aspect of the present invention.

Assume, for purposes of illustration, that the example optical system created according to the methodology of FIG. 8 is to be employed for microscopic-digital imaging. By way of comparison, in classical microscopy, in order to image and resolve structures of a size approaching 1 micron (and below), magnifications of many hundreds usually are required. The basic reason for this is that such optics conventionally have been designed for the situation when the sensor of choice is the human eye. In contrast, the methodology of FIG. 8 designs the optical system in view of the sensor, which affords significant performance increases at reduced cost.

In the k-space design methodology, according to an aspect of the present invention, the optical system is designed around a discrete sensor that has known fixed dimensions. As a result, the methodology can provide a far more straightforward, robust, and inexpensive optical system design approach to "back-project" the sensor size onto the object plane and calculate a magnification factor. A second part of the methodology facilitates that the optics that provide the magnification have a sufficient NA to optically resolve a spot of similar dimensions as the back-projected pixel. Advantageously, an optical system designed in accordance with an aspect of the present invention can utilize custom and/or off-the-shelf components. Thus, for this example, inexpensive optics can be employed in accordance with an aspect of the present invention to obtain suitable results, but well-corrected microscope optics are relatively inexpensive. If custom-designed optics are utilized, in accordance with an aspect of the present invention, then the range of permissible magnifications and numerical apertures becomes substantial, and some performance gains can be realized over the use of off-the-shelf optical components.

In view of the concepts described above in relation to FIGS. 1–8, a plurality of related imaging applications can be enabled and enhanced by the present invention. For example, these applications can include but are not limited to imaging, control, inspection, microscopy and/or other automated analysis such as:

(1) Bio-medical analysis (e.g., cell colony counting, histology, frozen sections, cellular cytology, Meachanical, Laser or radiation-based, and other Micro-dissection, Haematology, pathology, oncology, fluorescence, interference, phase and many other clinical microscopy applications);

(2) Particle Sizing Applications (e.g., Pharmaceutical manufacturers, paint manufacturers, cosmetics manufacturers, food process engineering, and others);

(3) Air quality monitoring and airborne particulate measurement (e.g., clean room certification, environmental certification, and so forth);

(4) Optical defect analysis, and other requirements for high resolution microscopic inspection of both transmissive and opaque materials (as in metallurgy, automated semiconductor inspection and analysis, automated vision systems, 3-D imaging and so forth); and (5) Imaging technologies such as cameras, copiers, FAX machines and medical systems as well as other technologies/applications which are described in more detail below.

Figure 9:
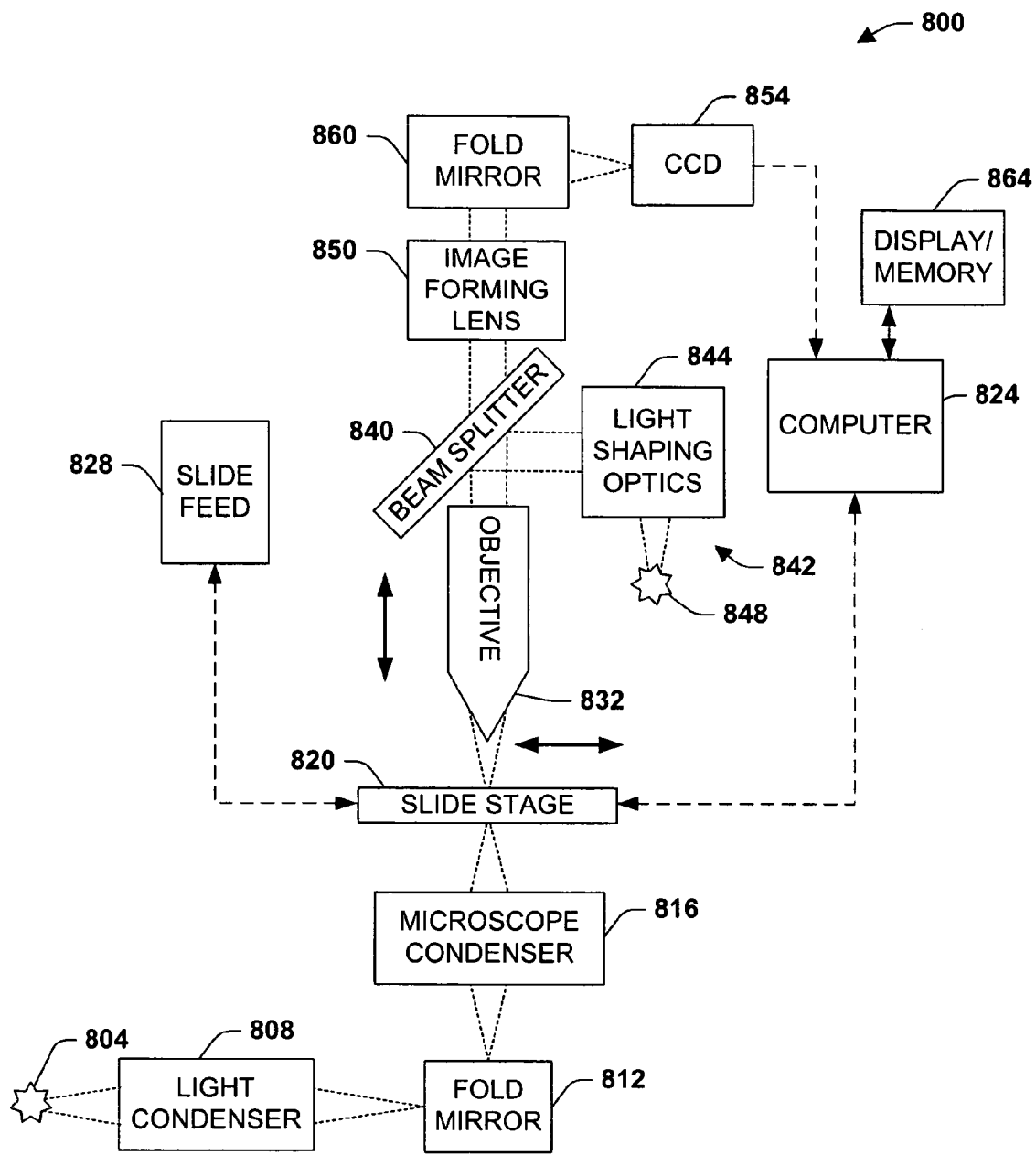
FIG. 9 is a schematic block diagram illustrating an exemplary imaging system in accordance with an aspect of the present invention.

FIGS. 9, 10, 11, 12, and 13 illustrate possible example systems that can be constructed employing the concepts previously described above in relation to FIGS. 1–8. FIG. 9 is a flow diagram of light paths in an imaging system 800 adapted in accordance with the present invention.

The system 800 employs a light source 804 emitting illuminating light that is received by a light condenser 808. Output from the light condenser 808 is directed to a microscope condenser 816 (such output from 808 also can be directed by a fold mirror, or other component or components that redirect the optical path, as shown at 812) that projects illuminating light onto a slide stage 820, wherein an object (not shown, positioned on top of, or within the slide stage and the Field Volume Depth at the object plane) can be imaged in accordance with the present invention. The slide stage 820 can be automatically positioned (and/or manually) via a computer 824 and associated slide feed 828 in order to image one or more objects in a field of view defined by an objective lens 832. It is noted that the objective lens 832 and/or other components depicted in the system 800 may be adjusted manually and/or automatically via the computer 824 and associated controls (not shown) (e.g., servo motors, tube slides, linear and/or rotary position encoders, optical, magnetic, electronic, or other feedback mechanisms, control software, and so forth) to achieve different and/or desired image characteristics (e.g., magnification, focus, which objects appear in field of view, depth of field and so forth).

Light output from the objective lens 832 can be directed through an optional beam splitter 840, wherein the beam splitter 840 is operative with an alternative epi-illumination section 842 (to light objects from above slide stage 820) including light shaping optics 844 and associated light source 848. Light passing through the beam splitter 840 is received by an image forming lens 850. Output from the image forming lens 850 is directed to a CCD or other imaging sensor or device 854. It is shown that the output of 850 can also be directed to device 854 via a fold mirror 860, or other component or components that redirect the optical path as desired. The CCD or other imaging sensor or device 854 converts the light received from the object to digital information for transmission to the computer 824, wherein the object image can be displayed to a user in real-time and/or stored in memory at 864. As noted above, the digital information defining the image captured by the CCD or other imaging sensor or device 854 can be routed as bit-map information to the display/memory 864 by the computer 824. It is to be appreciated that "display" can be any of, but not limited to any type of computer monitor, CRT, LCD, TV, organic light emitting device display (OLED), or other semi-conductor image display device; miniature or any other type large or small-scale display projector, head-mount, flexible, monocular, binocular, or projection display, retinal display, Head-Up display, and others of the like. If desired, image processing such as automatic comparisons with pre-determined samples or images can be performed to determine an identity of and/or analyze the object under examination. This can also include employment of substantially any type of image processing technology or software that can be applied to the captured image data within the memory 864.

Figure 10:
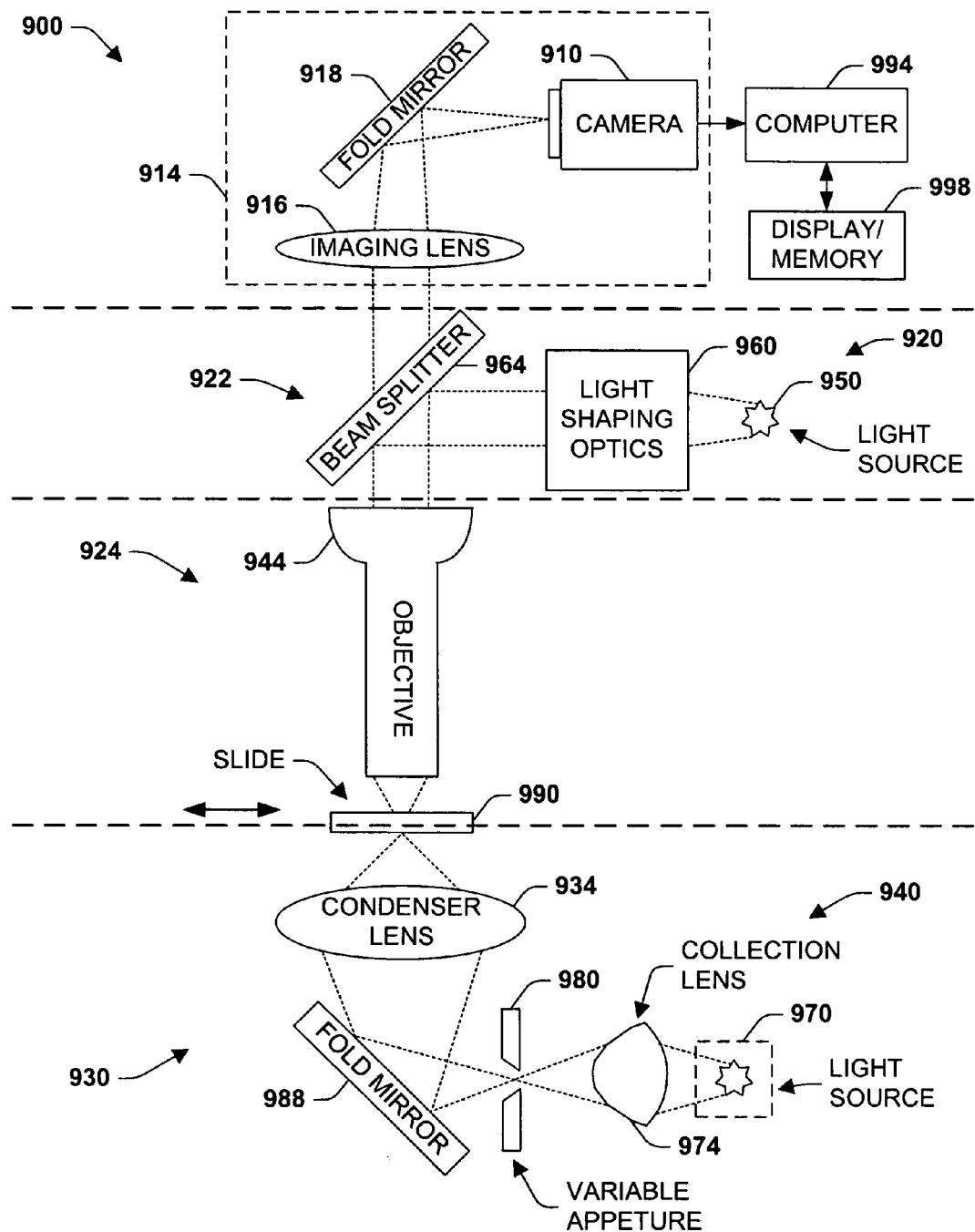
FIG. 10 is a schematic block diagram illustrating a modular imaging system in accordance with an aspect of the present invention.

FIG. 10 is a system 900 depicting an exemplary modular approach to imaging design in accordance with an aspect of the present invention. The system 900 can be based on a sensor array 910 (e.g., provided in off-the-shelf camera) with a pixel pitch of approximately 8 microns (or other dimension), for example, wherein array sizes can vary from 640×480 to 1280×1024 (or other dimensions as noted above as currently extant products or any other such arrays as might become available.). The system 900 includes a modular design wherein a respective module is substantially isolated from another module, thus, mitigating alignment tolerances.

The modules can include:
a camera/sensor module, 914 including an image-forming lens 916 and/or fold mirror 918;
an epi-illumination module 920 for insertion into a k-space region 922;
a sample holding and presentation module 924;
a light-shaping module 930 including a condenser 934; and
a sub-stage lighting module 940.

It is noted that the system 900 can advantageously employ commercially-available components such as for example:
condenser optics 934 (NA<=1) for the light presentation; (e.g., Olympus U-SC-2)
standard plan/achromatic objective lenses or any other available or custom optical design and characteristic transmissive, reflective, or other optical path directive components 944 of power and numerical aperture e.g.,: (4×, 0.10), (10×, 0.25), (20×, 0.40), (40×, 0.65) selected to satisfy the desired characteristic that for a given magnification, the projected pixel-pitch at the object plane is similar in dimensions to the diffraction-limited resolved spot of the optics.
(e.g., Olympus 1-UB222, 1-UB223, 1-UB225, 1-UB227)

The system 900 utilizes an infinity-space (k-space) between the objective lens 944 and the image-forming lens 916 in order to facilitate the insertion of auxiliary and/or additional optical components, modules, filters, and so forth in the k-space region at 922 such as for example, when the image-forming lens 916 is adapted as an f=150 mm achromatic triplet. Furthermore, an infinity-space (k-space) between the objective lens 944 and the image-forming lens 916 can be provided in order to facilitate the injection of object illumination light (via a light-forming path) into an optical path for epi-illumination. For example, the light-forming path for epi-illumination can include:
a light source 950 such as an LED driven from a current-stabilised supply;
(e.g., HP HLMP-CW30)
a transmission hologram for source homogenisation and the imposition of a spatial virtual-source at 950;
(e.g., POC light shaping diffuser polyester film 30-degree FWHM)
a variable aperture at 960 to restrict the NA of the source 950 to that of the imaging optics, thereby mitigating the effect of scattered light entering the image-forming optical path;
(e.g., Thorlabs iris diaphragm SM1D12 0.5–12.0 mm aperture)
a collection lens at 960 employed to maximize the light gathered from the virtual source 950, and to match the k-space characteristics of the source to that of the imaging optics; and
(e.g., f=50 mm aspheric lens, f=50 mm achromatic doublet)
a partially-reflective beam splitter 964 employed to form a coaxial light path and image path. For example, the optic 964 provides a 50% reflectivity on a first surface (at an inclination of 45 degrees), and is broadband antireflection coated on a second surface.

The sub-stage lighting module 940 is provided by an arrangement that is substantially similar to that of the epi-illumination described above for example:
a light source 970 (an LED driven from a current-stabilised supply);
(e.g., HP HLMP-CW30)
a transmission hologram (associated with light source 970) for the purposes of source homogenisation and the imposition of a spatial virtual-source;
(e.g., POC light shaping diffuser polyester film 30-degree FWHM)

a collection lens 974 employed to maximize the light gathered from the virtual source 970, and to match the k-space characteristics of the source to that of the imaging optics;
  (e.g., f=50 mm aspheric lens, f=50 mm achromatic doublet)
a variable aperture 980 to restrict the NA of the source 970 to that of the imaging optics, thereby mitigating the effect of scattered light entering the image-forming optical path;
  (e.g., Thorlabs iris diaphragm SM1D12 0.5–12.0 mm aperture)
a mirror 988 utilized to turn the optical path through 90 degrees and provide fine-adjustment in order to accurately align the optical modules, though it will be appreciated that the described optical path length "turn" is not required for such alignment but facilitates such alignment by mitigating mechanical and tolerancing errors; and
a relay lens (not shown) employed to accurately position the image of the variable aperture 980 onto the object plane (at slide 990), thereby, along with suitable placement of a holographic diffuser, thus, achieving Kohler illumination.
  (e.g., f=100 mm simple piano-convex lens).

As described above, a computer 994 and associated display/memory 998 is provided to display in real-time and/or store/process digital image data captured in accordance with the present invention.

Figure 11:
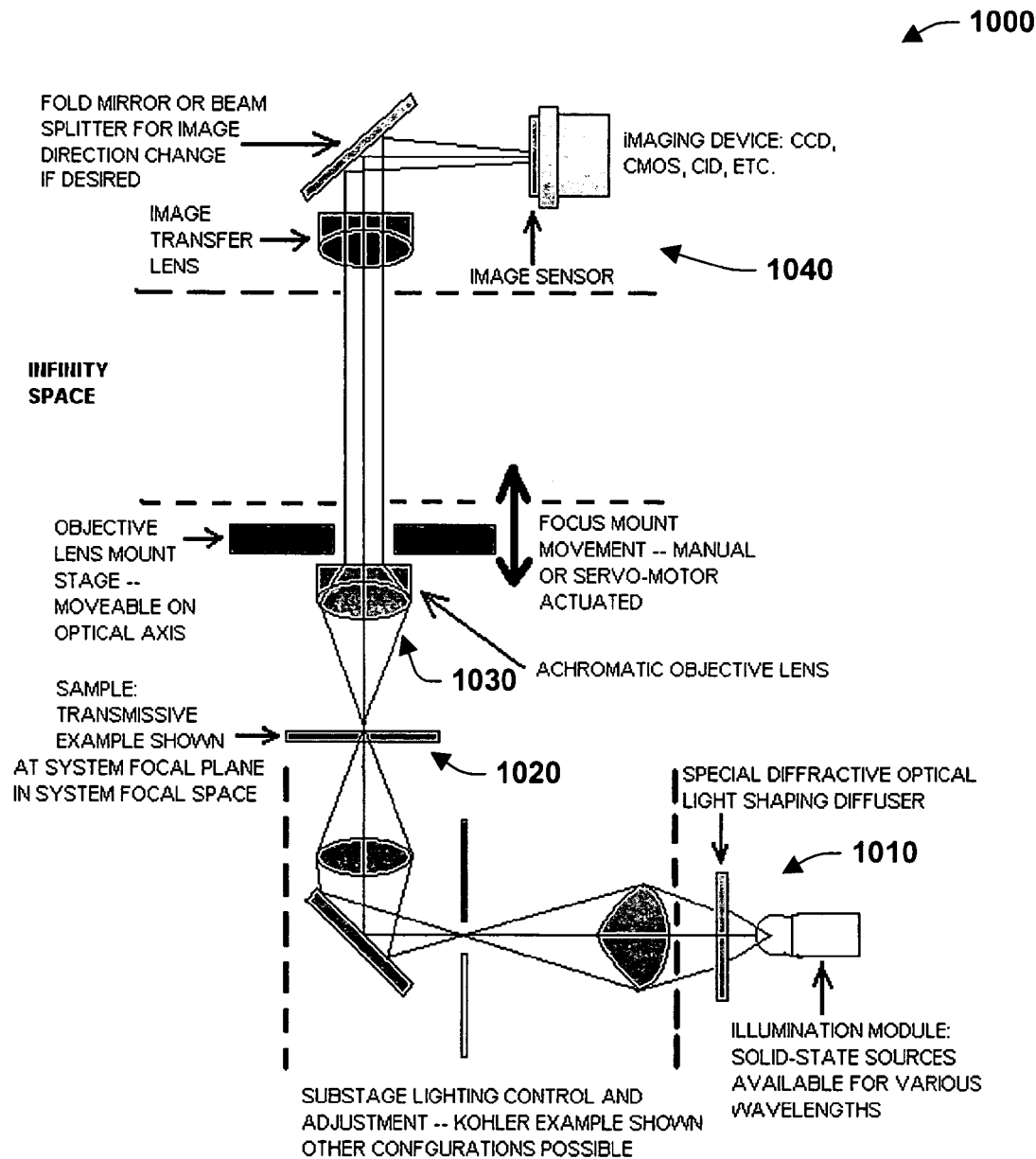
FIGS. 11–13 illustrate alternative imaging systems in accordance with an aspect of the present invention.

FIG. 11 illustrates a system 1000 in accordance with an aspect of the present invention. In this aspect, a sub-stage lighting module 1010 (e.g., Kohler, Abbe) can project light through a transmissive slide 1020 (object under examination not shown), wherein an achromatic objective lens 1030 receives light from the slide and directs the light to an image capture module at 1040. It is noted that the achromatic objective lens 1030 and/or slide 1020 can be manually and/or automatically controlled to position the object(s) under examination and/or position the objective lens.

Figure 12:
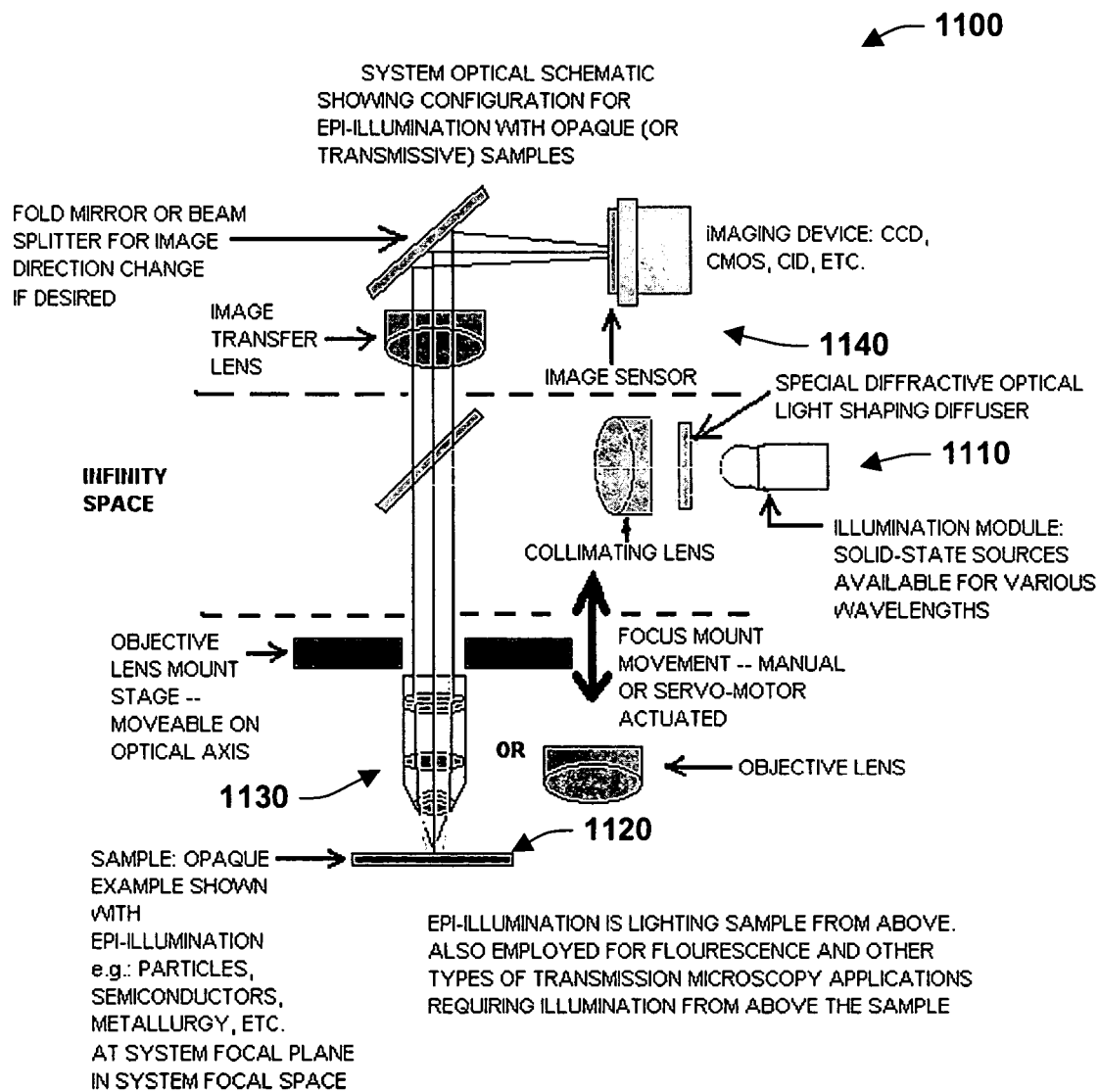
Figure 13:
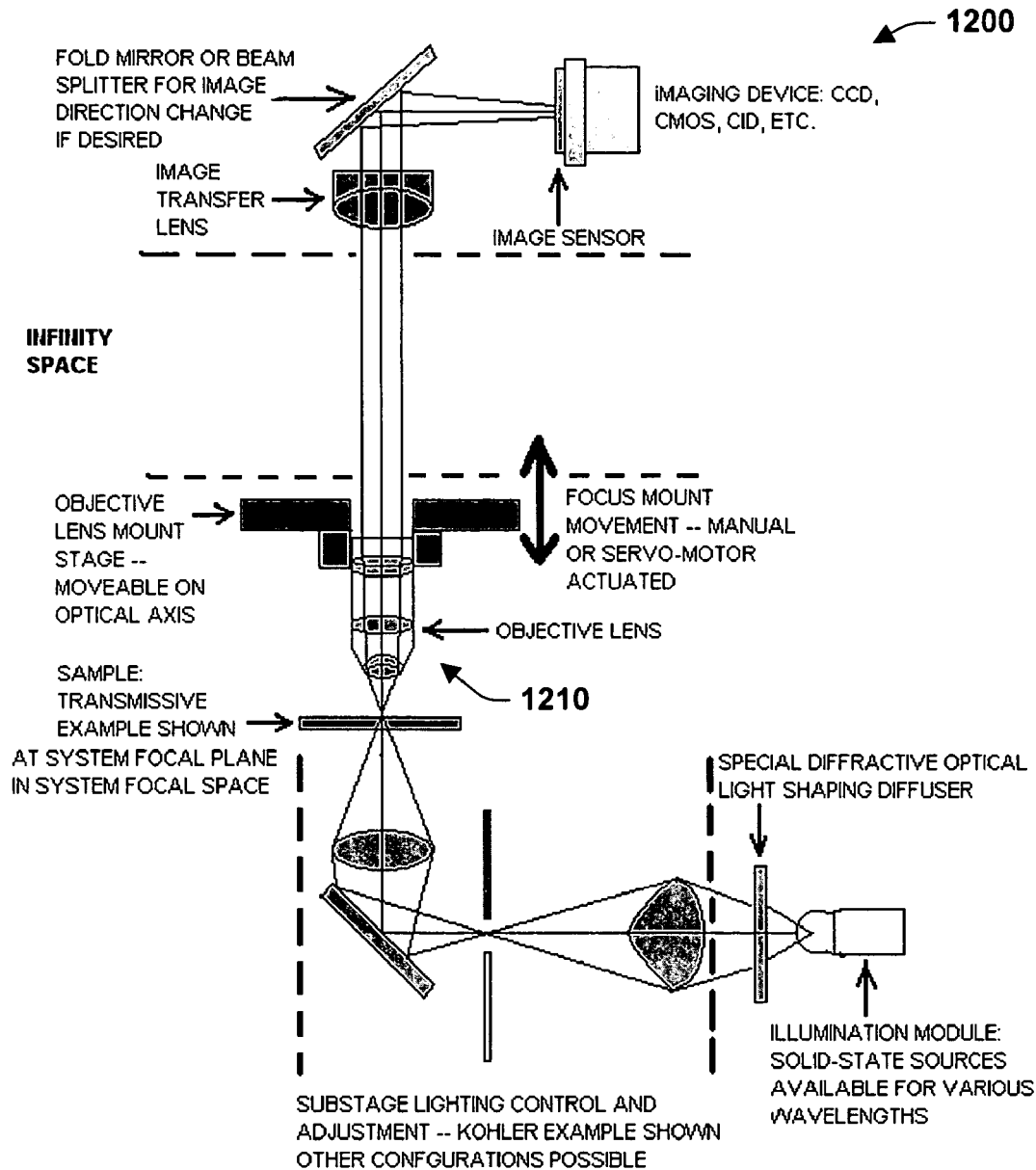

FIG. 12 illustrates a system 1100 in accordance with an aspect of the present invention. In this aspect, a top-stage or epi-illumination lighting module 1110 can project light to illuminate transmissive or opaque objects on an appropriately transmissive or opaque slide or carrier or suitable mounting substrate 1120 (object under examination not shown), wherein an objective lens 1130 (can be compound lens device or other type) receives light from the slide and directs the light to an image capture module at 1140. As noted above, the objective lens 1130 and/or slide 1120 can be manually and/or automatically controlled to position the object(s) under examination and/or position the objective lens. FIG. 13 depicts a system 1200 that is similar to the system 1000 in FIG. 11 except that a compound objective lens 1210 is employed in place of an achromatic objective lens.

The imaging systems and processes described above in connection with FIGS. 1–13 may thus be employed to capture/process an image of a sample, wherein the imaging systems are coupled to a processor or computer that reads the image generated by the imaging systems and compares the image to a variety of images in an on-board data store in any number of current memory technologies.

For example, the computer can include an analysis component to perform the comparison. Some of the many algorithms employed in image processing include, but are not limited to convolution (on which many others are based), FFT, DCT, thinning (or skeletonization), edge detection and contrast enhancement. These are usually implemented in software but may also use special purpose hardware for speed. FFT (fast Fourier transform) is an algorithm for computing the Fourier transform of a set of discrete data values. Given a finite set of data points, for example, a periodic sampling taken from a real-world signal, the FFT expresses the data in terms of its component frequencies. It also addresses the essentially identical inverse concerns of reconstructing a signal from the frequency data. DCT (discrete cosine transform) is a technique for expressing a waveform as a weighted sum of cosines. There are a various extant programming languages designed for image processing which include but are not limited to those such as IDL, Image Pro, Matlab, and many others. There are also no specific limits to the special and custom image processing algorithms that may be written to perform functional image manipulations and analyses.

The k-space design of the present invention also allows for direct optical correlation of the Fourier Frequency information contained in the image with stored information to perform real-time optically correlated image processed analyses of a given sample object.

Figure 14:
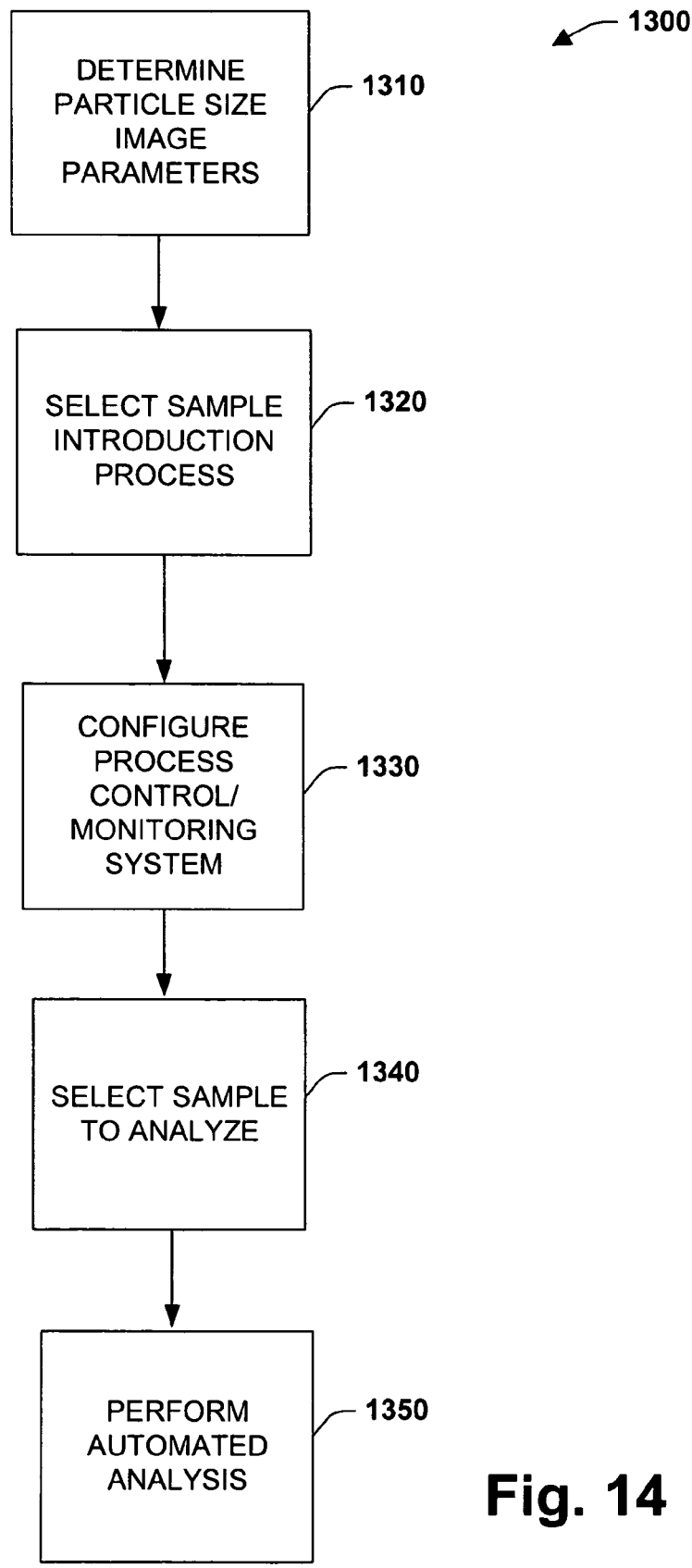
FIGS. 14–18 illustrate exemplary applications in accordance with the present invention.

FIG. 14 illustrates a particle sizing application 1300 that can be employed with the systems and processes previously described. Particle sizing can include real-time, closed/open loop monitoring, manufacturing with, and control of particles in view of automatically determined particles sizes in accordance with the k-space design concepts previously described. This can include automated analysis and detection techniques for various particles having similar or different sizes (n different sizes, n being an integer) and particle identification of m-shaped/dimensioned particles, m being an integer). In one aspect of the present invention, desired particle size detection and analysis can be achieved via a direct measurement approach. This implies that the absolute spatial resolution per pixel relates directly (or substantially thereto) in units of linear measure to the imaged particles without substantial account of the particle medium and associated particle distribution. Direct measurement generally does not create a model but rather provides a metrology and morphology of the imaged particles in any given sample. This mitigates processing of modelling algorithms, statistical algorithms, and other modelling limitations presented by current technology. Thus, an issue becomes one of sample handling and form that enhances the accuracy and precision of measurements since the particle data is directly imaged and measured rather than modelled, if desired.

Proceeding to 1310 of the particle sizing application 1300, particle size image parameters are determined. For example, basic device design can be configured for imaging at desired Absolute Spatial Resolution per pixel and Effective Resolved Magnification as previously described. These parameters determine field of view (FOV), depth of field (DOF), and working distance (WD), for example. Real-time measurement can be achieved by either synchronous or asynchronous imaging of a medium at selected timing intervals, in real-time at common video rates, and/or at image capture rates as desired. Real-time imaging can also be achieved by capturing images at selected times for subsequent image processing. Asynchronous imaging can be achieved by capturing images at selected times by pulsing an instrument illumination at selected times and duty cycles for subsequent image processing.

At 1320, a sample introduction process is selected for automated (or manual) analysis. Samples can be introduced into an imaging device adapted in accordance with the present invention in any of the following (but not limited to) imaging processes:

1) All previously described methods and transmissive media as well as:
2) Individual manual samples in cuvettes, slides, and/or transmissive medium.
3) Continuous flow of particles in stream of gas or liquid, for example.
4) With an imaging device configured for epi-Illumination or other suitable reflective illumination imaging, samples may be opaque and presented on an appropriately transmissive or opaque "carrier" (automated and/or manual) without substantial regard to the material analyzed.

At 1330, a process control and/or monitoring system is configured. Real-time, closed loop and/or open loop monitoring, manufacturing with (e.g., closing loop around particle size), and control of processes by direct measurement of particle characteristics (e.g., size, shape, morphology, cross section, distribution, density, packing fraction, and other parameters can be automatically determined). It is to be appreciated that although direct measurement techniques are performed on a given particle sample, that automated algorithms and/or processing can also be applied to the imaged sample if desired. Moreover, a direct measurement-based particle characterization device can be installed at substantially any given point in a manufacturing process to monitor and communicate particle characteristics for process control, quality control, and so forth by direct measurement.

At 1340, a plurality of different sample types can be selected for analysis. For example, particle samples in any of the aforementioned forms can be introduced in continuous flow, periodic, and/or asynchronous processes for direct measurement in a device as part of a process closed-feedback-loop system to control, record, and/or communicate particle characteristics of a given sample type (can also include open loop techniques if desired). Asynchronous and/or synchronous techniques can be employed (the first defines imaging with a triggering signal sent by an event, or trigger signal initiated by an event or object generating a trigger signal to initiate imaging, the second defines imaging with a timing signal sent to trigger illumination independent of object location or presence).

Asynchronous and/or synchronous imaging can be achieved by pulsing an illumination source to coincide with the desired image field with substantially any particle flow rate. This can be controlled by a computer, for example, and/or by a "trigger" mechanism, either mechanical, optical, and/or electronic, to "flash" solid state illumination on and off with a given duty cycle so that the image sensor captures, displays and records the image for processing and analysis. This provides a straight-forward process of illuminating and imaging given that it effectively can be timed to "stop the action"—or rather, "freeze" the motion of the flowing particles in the medium. In addition, this enables that a sample within the image field to capture particles within the field for subsequent image processing and analysis.

It is to be appreciated that other adaptations and/or definitions for analyzing particles or materials can be provided. Rather than a synchronous vs. asynchronous configuration, other imaging aspects can include "continuous imaging" and/or "image-on-demand" techniques. Continuous imaging is generally employed with static objects and steady-state lighting, and image-on-demand for stop-flow techniques (e.g., moving particles/objects, Brownian motion, and so forth). Stop-flow imaging can be achieved by strobing a light source for a short time, or by shuttering a camera rapidly, for example, yielding several possibilities:

1. Strobed illumination+ long exposure camera.
2. Continuous illumination+ short exposure (shuttered) camera.
3. Strobed illumination+ synchronised shuttered camera.

As can be appreciated, the above examples can be made synchronous by reference to a suitable time base, or made asynchronous by demanding an image at an arbitrary time interval.

Real-time (or substantially real time), closed loop and/or open loop monitoring, manufacturing with, and control of processes by k-space-based, direct measurement of particle characterization at 1340 is applicable to a broad range of processes including (but not limited to): Ceramics, metal powders, pharmaceuticals, cement, minerals, ores, coatings, adhesives, pigments, dyes, carbon black, filter materials, explosives, food preparations, health & cosmetic emulsions, polymers, plastics, micelles, beverages—and many more particle-based substances requiring process manufacturing, monitoring and control.

Other applications include but are not limited to:
Instrument calibration and standards;
Industrial-hygiene research;
Materials research;
Energy and combustion studies;
Diesel- and gasoline-engine emissions measurements;
Industrial emissions sampling;
Basic aerosol research;
Environmental studies;
Bio-aerosol detection;
Including but not limited to biologic agent or contaminant such as spores, bacteria fungi, etc.
Pharmaceutical research;
Health and agricultural experiments;
Clean-Room Monitoring;
Inhalation toxicology; and/or
Filter testing.

At 1350, software and/or hardware based computerized image processing/analysis can occur. Images from a device adapted in accordance with the present invention can be processed in accordance with substantially any hardware and/or software process. Software-based image processing can be achieved by custom software and/or commercially available software since the image file formats are digital formats (e.g., bit maps, TIFF, JPEG, and so forth or any other digital image file format (or combinations thereof) of captured particles).

Analysis, characterization, and so forth can also be provided by the following: For example, analyses can be metrologic (direct measurement based), correlative, and/or comparative (database) based. Correlative and/or comparative analyses can include comparisons to a database of (but not limited to) complete/partial visual image data, and/or component image data (e.g., FFT, or other frequency, and/or spatial or other intrinsic parametric image data derived from the image via image processing and/or direct optical correlation of the existing k-space frequency field created in accordance with the present invention from the imaged object or particle). Such techniques are described in more detail below. Advanced image processing can characterize and catalog images in real-time and/or periodic sample-measurements. Data can be discarded and/or recorded as desired, whereas data matching known sample characteristics can begin a suitable selected response, for example. Furthermore, a device adapted in accordance with the present invention can be linked for communication in any data transmission process. This can include wireless, broadband, wideband, ultra-wideband, phone modem, standard telecom, Ethernet or other network protocols (e.g., Internet, TCP/IP, Bluetooth, cable TV transmissions as well as others).

Figure 15:
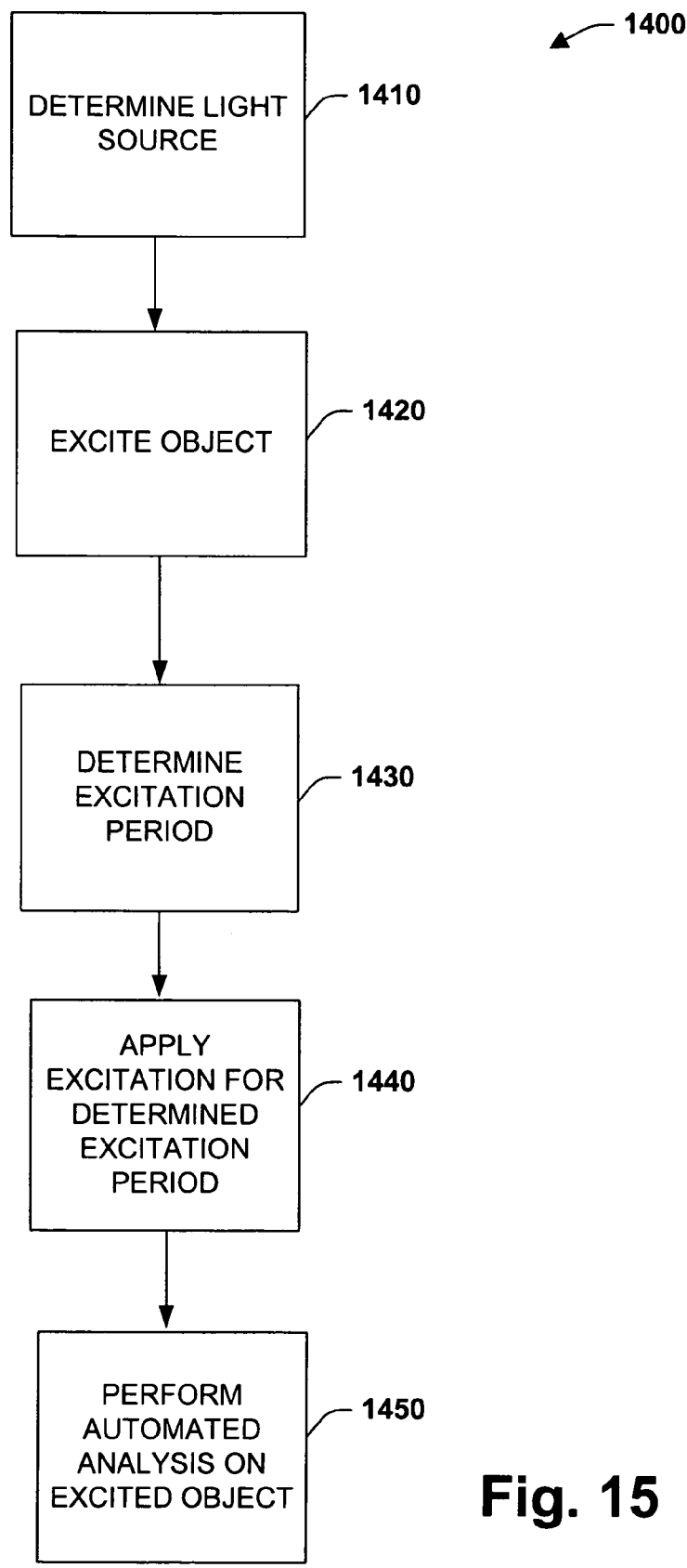

FIG. 15 illustrates an excitation application 1400 in accordance with an aspect of the present invention that can be employed with the systems and processes previously described. A k-space system is adapted in accordance with the present invention having a light system that includes a light source at 1410, such as a Light Emitting Diode (LED), emitting light having a wavelength of about 250 to about 400 nm (e.g., ultraviolet light). The LED can be employed to provide for epi-illumination or trans-illumination as described herein (or other type). The use of such an LED (or other UV light source) also enables wave-guide illumination in which the UV excitation wavelength is introduced onto a planar surface supporting the object under test at 1420, such that evanescent-wave coupling of the UV light can excite fluorophores within the object. For example, the UV light can be (but not limited to) provided at about a right angle to a substrate on which the object lies. At 1430, the LED (or other light source or combinations thereof) can emit light for a predetermined time period and/or be controlled in a strobe-like manner emitting pulses at a desired rate.

At 1440, excitation is applied to the object for the period determined at 1430. At 1450, automated and/or manual analysis is performed on the object during (and/or thereabout) the excitation period. It is noted that the excitation application 1400 described herein can apply to various processes. In one aspect, this includes a process wherein a high-energy photon (short wavelength) is absorbed and subsequently re-emitted as a lower-energy photon (longer wavelength). The time interval between absorption and emission generally determines whether the process is one of fluorescence or phosphorescence—which can also be defined as a "down-conversion" process.

By way of illustration, the object which is sensitive to ultraviolet in that it absorbs/emits photons in response to excitation of UV light from the light source.

Fluorescence (or phosphorescence) is a condition of a material (organic or inorganic) in which the material undergoes a process wherein a high-energy photon (short wavelength) is absorbed and subsequently re-emitted as a lower-energy photon (longer wavelength). The time interval between absorption and emission generally determines whether the process is one of fluorescence or phosphorescence—which can also be defined as a "down-conversion" process. It can also continue to emit light while absorbing excitation light. Both Fluorescence and phosphorescence can be an inherent property of a material (e.g., auto-fluorescence) or it can be induced, such as by employing fluorochrome stains or dyes. The dye can have an affinity to a particular protein, chemical component, physical component, and/or other receptiveness so as to facilitate revealing or discovering different conditions associated with the object. In one particular example, fluorescence microscopy (or phosphorescence microscopy) and/or digital imaging provide a manner in which to study various materials that exhibit secondary fluorescence (or phosphorescence).

By way of further example, the UV LED (or other source) can produce intense flashes of UV radiation for a short time period, with an image being constructed by a sensor (sensor adapted to the excitation wavelength) a short time later (e.g., milliseconds to seconds). This mode can be employed to investigate the time decay characteristics of the fluorescent (or phosphorescent) components of the object (or sample) being tested. This may be important where two parts of the object (or different samples) may respond (e.g., fluoresce/phosphorescence substantially the same under continuous illumination, but may have differing emission decay characteristics.

As a result of using the UV light source, such as the LED, the light from the light source can cause at least a portion of the object under test to emit light, generally not in the ultraviolet wavelength. Because at least a portion of the object fluoresces, (or phosphoresces) pre- or post-fluorescence/phosphorescence images can be correlated relative to those obtained during fluorescence/phosphorescence of the object to ascertain different characteristics of the object. In contrast, most conventional systems are configured to irradiate a specimen and then to separate the weaker re-radiating fluorescent light from the brighter excitation light, typically through filters. In order to enable detectable fluorescence, such conventional systems usually require powerful light sources. For example, the light sources can be mercury or xenon arc (burner) lamps, which produce high-intensity illumination powerful enough to image fluorescence specimens. In addition to running hot (e.g., typically 100–250 Watt lamps), these types of light sources typically have short operating lives (e.g., 10–100 hours). In addition, a power supply for such conventional light sources often includes a timer to help track the number of use hours, as arc lamps tend to become inefficient and degrade with decreasing or varying illumination output with use. The lamps are also more likely to shatter, if utilized beyond their rated lifetime. Moreover, conventional light sources such as Xenon and mercury arc lamps (burners) generally do not provide even intensity across the desired emission spectrum from ultraviolet to infrared, as much of the intensity of the mercury burner, for example, is expended in wavelengths across the near ultraviolet. This often requires precision filtering to remove undesired light wavelengths. Accordingly, it will be appreciated that using a UV LED, in accordance with an aspect of the present invention, provides a substantially even intensity at a desired UV wavelength to mitigate power consumption and heat generated through its use. Additionally, the replacement cost of a LED light source is significantly less than conventional lamps.

In accordance with the foregoing discussion it will be appreciated that the excitation source may also be any other light source so desired for irradiation of an object through the k-space region as described above. This could be, by way of example, an appropriate laser source. Such a laser source could be chosen to be applicable to applications of Multi-photon Fluorescence Microscopy.

By way of further example, it will be appreciated that referring again to FIG. 15 an excitation application is illustrated at 1400 in accordance with an aspect of the present invention that can be employed with the systems and processes previously described. A k-space system is adapted in accordance with the present invention having a light system that includes a Laser light source, such as (but not limited to) Ti:Sapphire Mode-Locked Lasers, and/or Nd:YLF Mode-Locked Pulsed Lasers. Such Lasers can be employed to provide for epi-illumination or trans-illumination as described herein (or other type). The use of such a Laser (or any other) also enables wave-guide illumination in which the excitation wavelength is introduced onto a planar surface supporting the object under test, such that evanescent-wave coupling of the Laser light can excite fluorophores within the object in accordance with the desired parameters of Multi-photon Fluorescence Microscopy. For example, the Laser light can be (but not limited to) provided at about a right angle to a substrate on which the object lies. The Laser source (or combinations thereof) can emit light for a predetermined time period and/or be controlled in a strobe-like manner emitting pulses at a desired rate. Automated and/or manual analysis can be performed on the object during (and/or thereabout) the excitation period. It is noted that the excitation application described herein can apply to various processes. In one aspect, this includes a process wherein Multi-photon Fluorescence Microscopy is the desired result. The present invention may be employed in any configuration desired (e.g., upright or inverted, or any other disposition such that the fundamental advantage of the optical design is employable.) Since excitation in multi-photon microscopy occurs at the focal point of a diffraction-limited microscope it provides the ability to "optically section" thick biological specimens in order to obtain three-dimensional resolution. These "optical sections" are acquired, typically, by raster scanning the specimen in the x-y plane, and "building" a full "three-dimensional image" which is composed by scanning the specimen at sequential z positions in series. Multi-photon fluorescence is useful, for example, for probing selected regions beneath the specimen surface. This is because the position of the focal point can be accurately determined and controlled.

The lasers commonly employed in optical microscopy are high-intensity monochromatic light sources, which are useful as tools for a variety of techniques including optical trapping, lifetime imaging studies, photo bleaching recovery, and total internal reflection fluorescence. In addition, lasers are also the most common light source for scanning confocal fluorescence microscopy, and have been utilized, although less frequently, in conventional wide field fluorescence investigations.

It will be appreciated that an aspect of the present invention could incorporate a suitable exciting laser source. It is noted that typical lasers employed for Multi-photon fluorescence currently include the Ti:sapphire pulsed laser and Nd:YLF (neodymium: yttrium lithium fluoride) laser (as well as other available laser sources.) The first is self mode-locked in operation and produces laser light over a broad range of near-infrared wavelengths with variable pulse widths and generally adjustable speed. The exciting laser is joined to the present invention through a suitable port. This could be accomplished employing fiber coupling with an optical wave-guide or direct coupling with relay mirrors placed by design to direct the laser energy through the k-space region to the object.

A typical multi-photon fluorescence microscope incorporates a detector system (e.g., a filtered photo multiplier or photodiode or other such detector to the laser wavelength) disposed in concert with an x-y raster scanning device which can rapidly deflect the focused laser beam across the objective field. Digital images collected by the microscope are processed and analyzed by a computer and associated software processing to assemble three-dimensional reconstructions from the "optical sections." These images display typical of the image sensor-visual microscope combination. Modem Multi-photon fluorescence microscopy has become a preferred technique for imaging living cells and tissues with three-dimensionally resolved fluorescence imaging since two-photon excitation, which occurs at the focal point of the microscope, minimizes photo bleaching and photo damage (the ultimate limiting factors in imaging live cells.) This in itself allows investigations on thick living tissue specimens that would not otherwise be possible with conventional imaging techniques.

The mechanisms that enable sophisticated multi-photon fluorescence microscopy result from two-photon and three-photon excitation, for example. These occur when two or three photons are absorbed by fluorophores in a quantitized event. Photons can, in this way be absorbed at high enough photon by combining their energies to force an electronic transition of a fluorosphore to the excited state.

Figure 16:
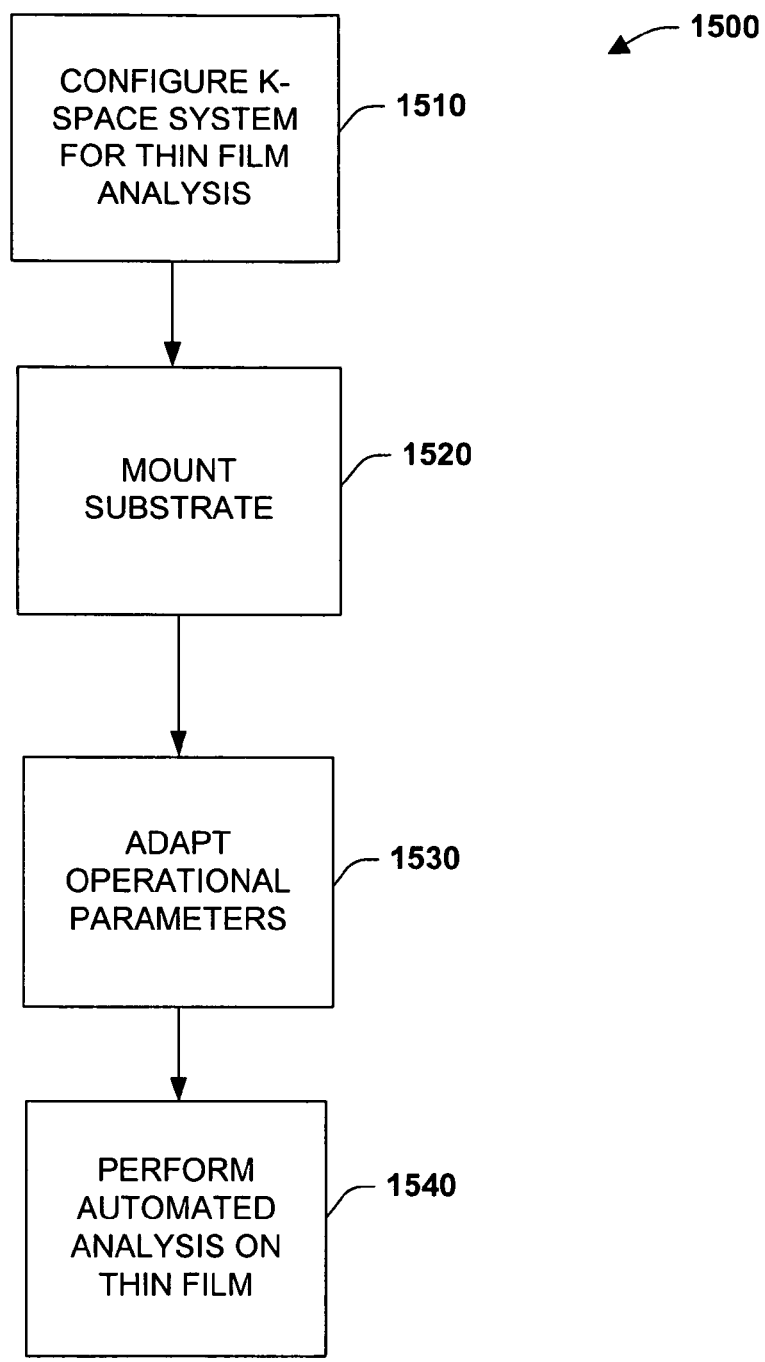

FIG. 16 illustrates a thin films application 1500 in accordance with an aspect of the present invention. Films and thin films can be characterized in general terms as thin layers (varying from molecular thickness(es) to significant microscopic to macroscopic thickness(es) of some material, or multiple materials, deposited in a manner suitable to respective materials onto various substrates of choice and can include (but are not limited to) any of the following: metallic coating (e.g., reflective, including partial, opaque, and transmissive), optical coatings (e.g., interference, transmission, anti-reflective, pass-band, blocking, protective, multi-coat, and so forth), plating (e.g., metallic, oxide, chemical, anti-oxidant, thermal, and so forth), electrically conductive (e.g., macro and micro-circuit deposited and constructed), optically conductive (e.g., deposited optical materials of varying index of refraction, micro- and macro-optical "circuits."). This can also include other coatings and layered film and film-like materials on any substrate which can be characterized by deposition in various manners so as to leave a desired layer or multiplicity of layers of some material(s) on said substrate in a desired thickness, consistency, continuity, uniformity, adhesion, and other parameters associated with any given deposited film. Associated thin film analysis can include, but is not limited to detection of micro bubbles, voids, microscopic debris, depositing flaws, and so forth.

Proceeding to 1510, a k-space system is configured for thin film analysis in accordance with an aspect of the present invention. The application of a k-space imaging device to the problem of thin-film inspection and characterization can be employed in identifying and characterizing flaws in a thin film layer or multiplicity of layers of thin films for example. Such a system can be adapted to facilitate:

1) manual observation of a substrate with deposited thin film of all types;

2) automatic observation/analysis and characterization of a substrate with deposited thin film of all types for pass-fail inspection;

3) automatic observation and characterization of a substrate with deposited thin film of all types for computer-controlled comparative disposition, this can include image data written to recording media of choice (e.g., CD-ROM, DVD-ROM) for verification, certification, and so forth.

A k-space device can be configured for imaging at desired Absolute Spatial Resolution (ASR) per pixel and desired Effective Resolved Magnification (ERM). These parameters facilitate determining FOV, DOF, and WD, for example. This can include objective-based design configurations and/or achromat-design configurations (e.g., for wide FOV and moderate ERM, and ASR). Illumination can be selected based on inspection parameters as trans-illumination and/or epi-illumination, for example.

At 1520, a substrate is mounted in an imager in such a manner as to enable a defined area of, or an entire area of interest of the substrate to be scanned by:

1) movement of an optical imaging path-length by optical scanning method; and/or 2) indexing an object being tested directly by a process of mechanical motion and control (e.g., automatic by computer or manual by operator). This facilitates an inspection of an entire surface or portion of the surface as desired.

As noted above in context of particle sizing, asynchronous or synchronous imaging at selected timing intervals and/or in real-time for respective scanned areas (e.g., determined by FOV) of substrate at common video rates and/or at image capture rates can be provided. Images of indexed and/or scanned areas can be captured with desired frequency for subsequent image processing. In addition, samples can be introduced into the device manually and/or in an automated manner from a "feed" such as from a conveyor system.

At 1530, operational parameters for thin film applications are determined and applied. Typical operational parameters can include but are not limited to:

1) Imaging of various flaws and characteristics including, but not limited to, particles and holes on a surface(s) (or within) a thin film or multiplicity of layers of such films;
2) Modular designs which can be varied as needed for both reflective and transparent films and/or substrates and/or surfaces;
3) Automated counting and categorization of surface flaws by size, location, and/or number on successively indexed (and/or "scanned") image areas (with index identification and totals for respective sample surfaces);
4) Register location of defects for subsequent manual inspection;
5) Provide images in standard format(s) for subsequent porting (e.g., via Ethernet or other protocol) or manual and/or automated image processing for archive and documentation on a computer, server, and/or client and/or remote transmission via any selected data transmission protocol;
6) Nominal scan time per surface of seconds to minutes dependent on total area. Scan and indexing speed generally understood to vary with sample area and subsequent processing.

At 1540, software and/or hardware based computerized image processing/analysis can occur. Images from a device adapted in accordance with the present invention can be processed in accordance with substantially any hardware and/or software process. Software-based image processing can be achieved by custom software and/or commercially available software since the image file formats are digital formats (e.g., bit maps, TIFF, JPEG, and so forth or any other digital image file format (or combinations thereof) of captured images of films).

Analysis, characterization and so forth can also be provided by the following: For example, analyses can be metrologic (direct measurement based) correlative, and/or comparative (data-base) based. Correlative and/or comparative analyses can include comparisons to a database of (but not limited to) complete/partial visual image data, and/or component image data (e.g., FFT, or other frequency, and/or spatial or other intrinsic parametric image data derived from the image via image processing and/or direct optical correlation of the existing k-space frequency field created in accordance with the present invention from the imaged thin film). Such techniques are described in more detail below.

Advanced image processing can characterize and catalog images in real-time and/or periodic sample-measurements. Data can be discarded and/or recorded as desired, whereas data matching known sample characteristics can begin a suitable selected response, for example. Furthermore, a device adapted in accordance with the present invention can be linked for communication in any data transmission process. This can included wireless, broadband, wideband, ultra-wideband, phone modem, standard telecom, Ethernet or other network protocols (e.g., Internet, TCP/IP, Bluetooth, cable TV transmissions as well as others). It is to be appreciated that imaging of substrate material in accordance with the present invention can be provided on a substantially absolute scale of quality control and traceable via image storage, whereas current techniques typically only provide statistical quality control and are often intensely labor-based with no associated stored images.

In another aspect of the present invention, an imaging system adapted as described above provides high Effective Resolved Magnification and high Absolute Spatial Resolution among other features of biological material and methods that can be combined to provide improved biological material imaging systems and methods. The biological material imaging systems and methods of the present invention enable the production of improved images (higher Effective Resolved Magnification (ERM), improved Absolute Spatial Resolution (ASR), improved depth of field, and the like) leading to the identification of biological materials as well as the classification of biological materials (for example as normal or abnormal).

Biological material includes microorganisms (organisms too small to be observed with the unaided eye) such as bacteria, virus, protozoans, fungi, and ciliates; cell material from organisms such cells (lysed, intracellular material, or whole cells), proteins, antibodies, lipids, and carbohydrates, tagged or untagged; and portions of organisms such as clumps of cells (tissue samples), blood, pupils, irises, finger tips, teeth, portions of the skin, hair, mucous membranes, bladder, breast, male/female reproductive system components, muscle, vascular components, central nervous system components, liver, bone, colon, pancreas, and the like. Since the biological material imaging system of the present invention can employ a relatively large working distance with the advantage of higher ERM and ASR than conventional instrumentation has traditionally allowed, portions of the human body may be directly examined without the need for removing a tissue sample.

Cells include human cells, non-human animal cells, plant cells, and synthetic/research cells. Cells include prokaryotic and eukaryotic cells. Cells may be in microscopic tissue samples, microtomed (or the like) slices of tissue, or individual cells or multi-cellular groups which have been microdissected or resected by any appropriate means. Cells may be healthy, cancerous, mutated, damaged, or diseased.

Examples of non-human cells include anthrax, *Actinomycetes* spp., *Azotobacter, Bacillus anthracis, Bacillus cereus, Bacteroides* species, *Bordetella pertussis, Borrelia burgdorferi, Campylobacter jejuni, Chlamydia* species, *Clostridium* species, *Cyanobacteria, Deinococcus radiodurans, Escherichia coli, Enterococcus, Haemophilus influenzae, Helicobacter pylori, Klebsiella pneumoniae, Lactobacillus* spp., *Lawsonia intracellularis, Legionellae, Listeria* spp., *Micrococcus* spp., *Mycobacterium leprae, Mycobacterium tuberculosis, Myxobacteria, Neisseria gonorrheoeae, Neisseria meningitidis, Prevotella* spp., *Pseudomonas* spp., *Salmonellae, Serratia marcescens, Shigella* species, *Staphylococcus aureus, Streptococci, Thiomargarita namibiensis, Treponema pallidum, Vibrio cholerae, Yersinia enterocolitica, Yersinia pestis*, and the like.

Additional examples of biological material are those that cause illness such as colds, infections, malaria, chlamydia, syphilis, gonorrhea, conjunctivitis, anthrax, meningitis, botulism, diarrhea, brucellosis, campylobacter, candidiasis, cholera, coccidioidomycosis, cryptococcosis, diphtheria, pneumonia, foodborne infections, glanders (*burkholderia mallei*), influenzae, leprosy, histoplasmosis, legionellosis, leptospirosis, listeriosis, melioidosis, nocardiosis, nontuberculosis mycobacterium, peptic ulcer disease, pertussis, pneumonia, psittacosis, *salmonella enteritidis*, shigellosis, sporotrichosis, strep throat, toxic shock syndrome, trachoma, typhoid fever, urinary trace infections, lyme disease, and the like. As described later, the present invention further relates to methods of diagnosing any of the above illnesses.

Examples of human cells include fibroblast cells, skeletal muscle cells, neutrophil white blood cells, lymphocyte white blood cells, erythroblast red blood cells, osteoblast bone cells, chondrocyte cartilage cells, basophil white blood cells, eosinophil white blood cells, adipocyte fat cells, invertebrate neurons (Helix aspera), mammalian neurons, adrenomedullary cells, melanocytes, epithelial cells, endothelial cells; tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells, osteoclasts, chondrocytes and other connective tissue cells, keratinocytes, melanocytes, liver cells, kidney cells, and adipocytes. Examples of research cells include transformed cells, Jurkat T cells, NIH3T3 cells, CHO, COS, etc.

A useful source of cell lines and other biological material may be found in ATCC Cell Lines and Hybridomas, Bacteria and Bacteriophages, Yeast, Mycology and Botany, and Protists: Algae and Protozoa, and others available from American Type Culture Co. (Rockville, Md.), all of which are herein incorporated by reference. These are non-limiting examples as a litany of cells and other biological material can be listed.

The identification or classification of biological material can in some instances lead to the diagnosis of disease. Thus, the present invention also provides improved systems and methods of diagnosis. For example, the present invention also provides methods for detection and characterization of medical pathologies such as cancer, pathologies of musculoskeletal systems, digestive systems, reproductive systems, and the alimentary canal, in addition to atherosclerosis, angiogenesis, arteriosclerosis, inflamation, atherosclerotic heart disease, myocardial infarction, trauma to arterial or veinal walls, neurodegenerative disorders, and cardiopulmonary disorders. The present invention also provides methods for detection and characterization of viral and bacterial infections. The present invention also enables assessing the effects of various agents or physiological activities on biological materials, in both in vitro and in vivo systems. For example, the present invention enables assessment of the effect of a physiological agent, such as a drug, on a population of cells or tissue grown in culture.

The biological material imaging system of the present invention enables computer driven control or automated process control to obtain data from biological material samples. In this connection, a computer or processor, coupled with the biological material imaging system, contains or is coupled to a memory or data base containing images of biological material, such as diseased cells of various types. In this context, automatic designation of normal and abnormal biological material may be made. The biological material imaging system secures images from a given biological material sample, and the images are compared with images in the memory, such as images of diseased cells in the memory. In one sense, the computer/processor performs a comparison analysis of collected image data and stored image data, and based on the results of the analysis, formulates a determination of the identity of a given biological material; of the classification of a given biological material (normal/abnormal, cancerous/non-cancerous, benign/malignant, infected/not infected, and the like); and/or of a condition (diagnosis).

If the computer/processor determines that a sufficient degree of similarity is present between particular images from a biological material sample and saved images (such as of diseased cells or of the same biological material), then the image is saved and data associated with the image may be generated. If the computer/processor determines that a sufficient degree of similarity is not present between particular image of a biological material sample and saved images of diseased cells/particular biological material, then the biological material sample is repositioned and additional images are compared with images in the memory. It is to be appreciated that statistical methods can be applied by the computer/processor to assist in the determination that a sufficient degree of similarity is present between particular images from a biological material sample and saved images of biological material. Any suitable correlation means, memory, operating system, analytical component, and software/hardware may be employed by the computer/processor.

Figure 17:
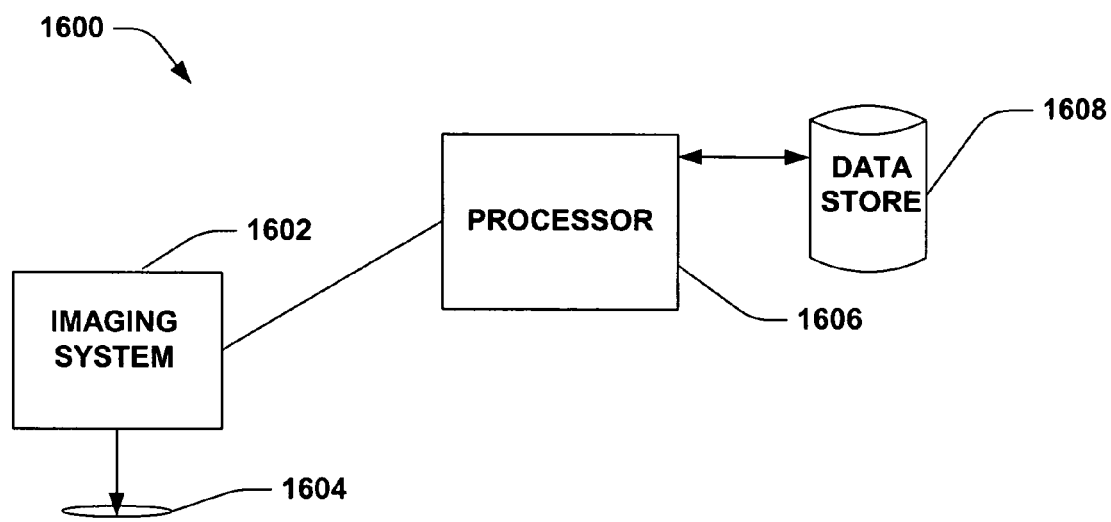

Referring to FIG. 17, an exemplary aspect of an automated biological material imaging system 1600 in accordance with one aspect of the present invention enabling computer driven control or automated process control to obtain data from biological material samples is shown. An imaging system 1602 described/configured in connection with FIGS. 1–16 above may be employed to capture an image of a biological material 1604. The imaging system 1602 is coupled to a processor 1606 and/or computer that reads the image generated by the imaging system 1602 and compares the image to a variety of images in the data store 1608.

The processor 1606 contains an analysis component to make the comparison. Some of the many algorithms used in image processing include convolution (on which many others are based), FFT, DCT, thinning (or skeletonisation), edge detection, pattern recognition, and contrast enhancement. These are usually implemented in software but may also use special purpose hardware for speed. FFT (fast Fourier transform) is an algorithm for computing the Fourier transform of a set of discrete data values. Given a finite set of data points, for example, a periodic sampling taken from a real-world signal, the FFT expresses the data in terms of its component frequencies. It also addresses the essentially identical inverse concerns of reconstructing a signal from the frequency data. DCT (discrete cosine transform) is technique for expressing a waveform as a weighted sum of cosines. There are several applications designed for image processing, e.g., CELIP (cellular language for image processing) and VPL (visual programming language).

The data store 1608 contains one or more sets of predetermined images. The images may include normal images of various biological materials and/or abnormal images of various biological materials (diseased, mutated, physically disrupted, and the like). The images stored in the data store 1608 provide a basis to determine whether or not a given captured image is similar or not similar (or the degree of similarity) to the stored images. In one aspect, the automated biological material imaging system 1600 can be employed to determine if a biological material sample is normal or abnormal. For example, the automated biological material imaging system 1600 can identify the presence of diseased cells, such as cancerous cells, in a biological material sample, thereby facilitating diagnosis of a given disease or condition. In another aspect, the automated biological material imaging system 1600 can diagnose the illnesses/diseases listed above by identifying the presence of an illness causing biological material (such as an illness causing bacteria described above) and/or determining that a given biological material is infected with an illness causing entity such as a bacteria or determining that a given biological material is abnormal (cancerous).

In yet another aspect, the automated biological material imaging system 1600 can be employed to determine the identity of a biological material of unknown origin. For example, the automated biological material imaging system 1600 can identify a white powder as containing anthrax. The automated biological material imaging system 1600 can also facilitate processing biological material, such as performing white blood cell or red blood cell counts on samples of blood, for example.

The computer/processor 1606 may be coupled to a controller which controls a servo motor or other means of moving the biological material sample within an object plane so that remote/hands free imaging is facilitated. That is, motors, adjusters, and/or other mechanical means can be employed to move the biological material sample slide within the object field of view.

Moreover, since the images of the biological material examination process are optimized for viewing from a computer screen, television, and/or closed circuit monitor or other such as described previously, remote and web based viewing and control may be implemented. Real time imaging facilitates at least one of rapid diagnosis, data collection/generation, and the like.

In another aspect, the biological material imaging system is directed to a portion of a human (such as lesion on an arm, haze on the cornea, and the like) and images formed. The images can be sent to a computer/processor (or across network such as Internet), which is instructed to identify the possible presence of a particular type of diseased cell (an image of which is stored in memory). When a diseased cell is identified, the computer/processor instructs the system to remove/destroy the diseased cell, for example, employing a laser, liquid nitrogen, cutting instrument, and/or the like.

Figure 18:
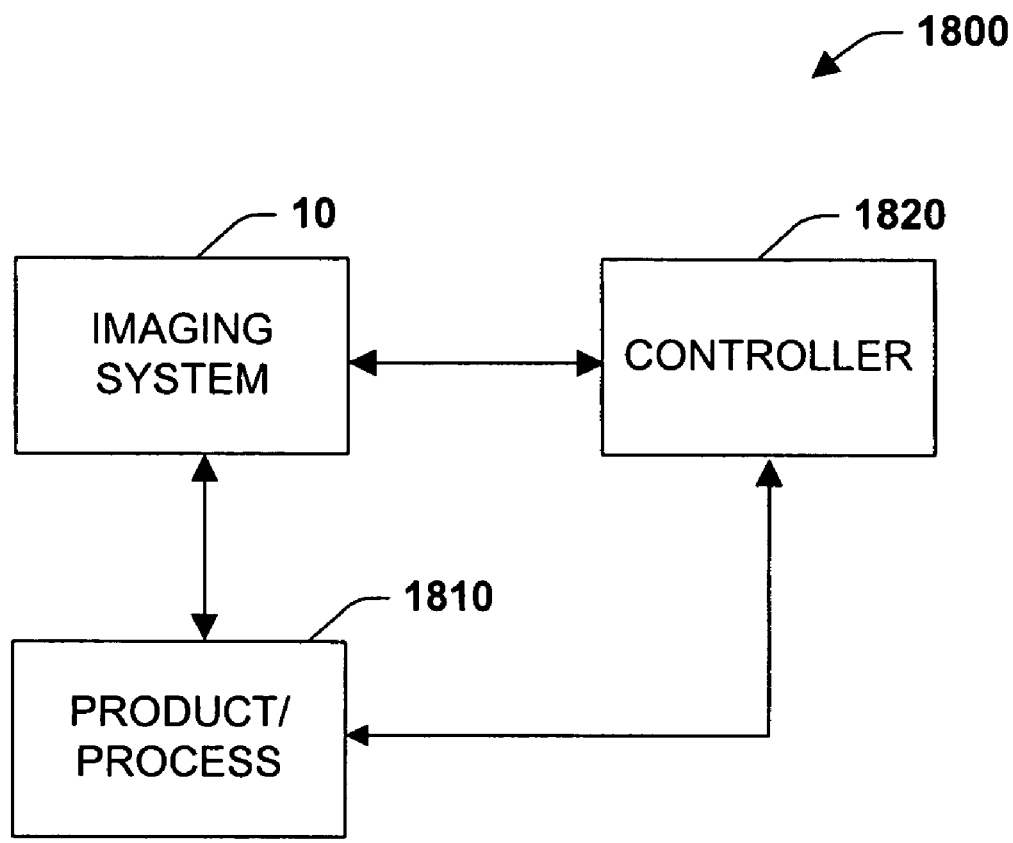

FIG. 18 depicts a high-level machine vision/analysis system 1800 in accordance with the subject invention. The system 1800 includes an imaging system 10 (FIG. 1) in accordance with the subject invention. The imaging system 10 is discussed in substantial detail supra and thus further discussion regarding details related thereto is omitted for sake of brevity.

The imaging system 10 can be employed to collect data relating to a product or process 1810, and provide the image information to a controller 1820 that can regulate the product or process 1810, for example, with respect to production, process control, quality control, testing, inspection, etc. The imaging system 10 as noted above provides for collecting image data at a granularity not achievable by many conventional systems. Moreover, the robust image data provided by the subject imaging system 10 can afford for highly effective machine vision inspection of the product or process 1810. For example, minute product defects typically not detectable by many conventional machine vision systems can be detected by the subject system 1800 as a result of the image data collected by the imaging system 10. The controller 1810 can be any suitable controller or control system employed in connection with a fabrication scheme, for example. The controller 1810 can employ the collected image data to reject a defective product or process, revise a product or process, accept a product or process, etc. as is common to machine-vision based control systems. It is to be appreciated that the system 1800 can be employed in any suitable machine-vision based environment, and all such applications of the subject invention are intended to fall within the scope of the hereto appended claims.

For example, the subject system 1800 could be employed in connection with semiconductor fabrication where device and/or process tolerances are critical to manufacturing consistent reliable semiconductor-based products. Thus, the product 1810 could represent a semiconductor wafer, for example, and the imaging system 1800 could be employed to collect data (e.g., critical dimensions, thicknesses, potential defects, other physical aspects . . . ) relating to devices being formed on the wafer. The controller 1820 can employ the collected data to reject the wafer because of various defects, modify a process in connection with fabricating devices on the wafer, accept the wafer, etc.

There are many instances where the imaging systems and processes of the present invention can facilitate semiconductor processing and/or fabrication. The imaging system of the present invention can one or more of inspect, monitor, and facilitate, in real time or post-processing, the formation of trenches, the formation of vias, the formation of dual damascene openings, the development of a photoresist, the formation of metal lines, the formation of spacers, the formation of metal interconnects, the deposition and/or etching of a dielectric material, the formation of gates including MOSFETs and non-volatile memory cells, the formation of bitlines and/or wordlines, chemical mechanic processing, the formation of an implant region, the patterning of a metal layer, the patterning of a dielectric layer, the patterning of a polysilicon layer, and the like.

The imaging system of the present invention can inspect for defects in a given structure once formed (defects as contaminants or as physical deformities). Consequently, the imaging system of the present invention can facilitate and/or improve fabrication of central processing units (CPUs), read only memory chips (ROMs), random access memory chips (RAMs), dynamic random access memory devices (DRAMs), static random access memory devices (SRAMs), input-output chips (IOs), non-volatile memory devices such as programmable read only memory devices (PROMs), erasable programmable read only memory devices (EPROMs), and electrical erasable programmable read only memory devices (EEPROMs), video game chips, and the like.

The imaging system of the present invention can facilitate optical networking component processing and/or fabrication. Optical networking components include optical integrated circuits, planar lightwave circuits, optical fiber connection devices, and the like. The imaging system of the present invention can facilitate liquid crystal device processing and/or fabrication and plasma display device processing and/or fabrication.

The imaging system of the present invention can facilitate recording media processing and/or fabrication. Recording media include data recording media, optical disks, compact disks (CDs), laser disks (LDs), digital video disks (DVDs), hard disk drives (HDDs), magnetic disks, memory sticks, video cards, and the like. For example, a CD contains a long string of pits and/or grooves written helically on the disk. An exemplary process begins by making a glass master (many other processes exist) by lapping flat and polishing a glass plate. The plate is coated with photoresist. A mastering tape is made containing the information to be written on the disk. A laser then writes the pattern from the master tape into the photoresist. The photoresist is developed. The imaging system of the present invention can inspect/monitor in real time and/or after development. A layer of metal is evaporated over the photoresist. Again, the imaging system of the present invention can inspect/monitor in real time or after metal deposition. The master is then checked for accuracy by playing the disk. The master is then subject to an electroforming process. In this electrochemical process, additional metal is deposited. When the metal is thick enough, the metal layer is separated from the glass master. This results in a metal negative impression of the disk called a father. The electroplating process is then repeated on the father. This typically generates several positive metal impressions from the father before the quality of the father degrades unacceptably. These impressions are called mothers. The electroplating process is repeated again on the mothers. Fabrication of the father and mothers can be checked or monitored by the imaging system of the present invention. Each mother typically makes several negative metal impressions called sons or stampers. The sons are suitable as molds for injection molding. Polycarbonate is often used to injection mold the CDs. Once the disks are molded, a metal layer is used to coat the disks. Following metal deposition, a thin plastic layer is spin coated on over the metal. The imaging system of the present invention can inspect/monitor in real time, before, during, and/or after one or more of the molding process, the metal coating process, and plastic spin-coating process.

Figure 19:
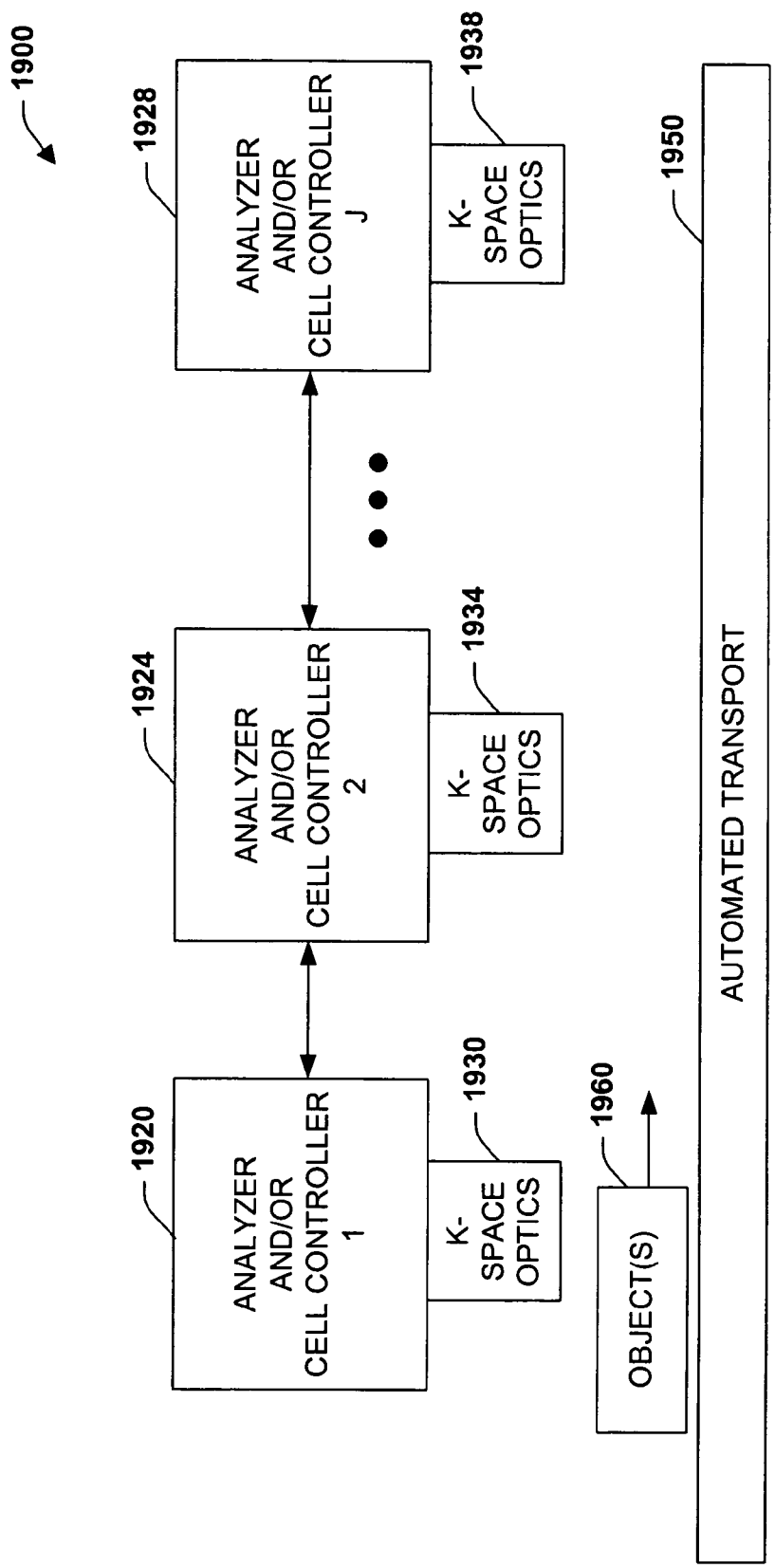
FIG. 19 illustrates an automated inspection and/or manufacturing system and process in accordance with an aspect of the present invention.

FIG. 19 illustrates an exemplary automated inspection and/or manufacturing system 1900 and process in accordance with an aspect of the present invention. The system 1900 includes 1 through J analyzers, J being an integer, depicted at reference numerals 1920 through 1928 having associated k-space optics 1930 though 1938 which are adapted in accordance with the sensor and optical parameters described above (e.g., correlating optical diffraction limited point with sensor pitch). An automated transport 1950 receives/moves/manipulates one or more objects 1960 as part of an automatic, semi-automatic and/or manual manufacturing and/or inspection operation (e.g., conveyors, belts, drives, directional conveyor sections, automated assembly/inspection lines/cells, and so forth). It is noted that transport of object 1960 (or positioning thereof) is not limited to straight-line transport (e.g., translational movements of objects and/or analyzers/optics in multiple dimensions such as from robotic movements and so forth).

The objects 1960 flow within range of the optics 1930–1938 (analyzers and associated optics can also move toward object at various angles), whereby the speed of the automated transport 1950 (or movement of analyzer/optics) may decrease or stop to enable an inspection and/or manufacturing operation. For example, the object 1960 may flow underneath the optics at 1930, wherein an image of the object (or portions therein) is captured by the analyzer 1920 via the optics. As the object 1960 flows down the transport 1950, subsequent image capture, analysis, and/or assembly can occur at analyzers 1924 and 1928, respectively. It is to be appreciated that object flow or movement for image capture can be from above or from the side or at other angles as well, —depending on positioning of object with respect to the optics 1930–1938. Automated imaging can include moving analyzers and/or optics with respect to objects, moving objects with respect to analyzers/optics, and/or combinations of movements between analyzers/optics, objects and transport mechanisms. Furthermore, respective analyzer stations 1920–1928 may be equipped with a plurality of respective optics and associated sensors for inspecting/manufacturing multiple objects and/or multiple portions associated with a respective object or objects.

The analyzers 1920–1928 include one or more sensors, memories, and computer components and can include processor and/or multi-processor/controller/I/O components to acquire/store/analyze a respective image, wherein the image is generally composed of digital bits of all or portions of the object 1960 as received/viewed from the optics 1930–1938. Respective images may also include data in proximity to the object 1960 such as between objects and/or at object peripheries. When the image has been captured in analyzer memory, a plurality of various measurements, calculations, computations, and/or algorithms can be performed on the image to determine if the object 1960 and/or portions associated with the object 1960 fall within or exceed desired or predetermined performance criteria (e.g., optical measurement within/outside predetermined parameter threshold, object 1960 or portions thereof compared to calibrated images in a database or memory). These determinations are described in more detail with respect to FIG. 20.

It is noted that analyzers 1920–1928 can include industrial control aspects and operate as isolated and/or coordinated manufacturing cells having communications there between (e.g., wireless and/or networked communications between cells and can include transporting image data to remote locations across networks such as the Internet for storage/analysis and/or control purposes). The industrial control aspects can be utilized to control the automated transport 1950, the analyzers and/or associated optics, and/or to control other portions of the system 1900. For example, feedback from the analyzers utilizing respective image data can be employed to control other machinery (not shown) (e.g., PLC's and associated I/O) in a closed loop or open loop manner when operating upon, or manufacturing, all or portions of the object 1960 as the object travels on the automated transport 1950 (e.g., controlling/inspecting semiconductor processes, welders, robots, machines, drills, cutters, water jets, valves, solenoids, films, other processes described previously and so forth). This can include robotic and/or other automated movements of the analyzers 1920–1928 and/or associated optics 1930–1938 when performing manufacturing/inspection operations. As can be appreciated, similar movements and/or measurements previously described can be employed in a machine vision and/or automated inspection context. Such inspection can include quality control and/or other metrics, wherein the object 1960 (or portions thereof) is categorized, approved, rejected, flagged, removed, discarded, passed to another cell and so forth.

It is to be appreciated that the automated manufacturing/inspection system 1900 depicted in FIG. 19 is intended to illustrate exemplary aspects of an automated system or process. As such, a plurality of other manufacturing cells, transports, robots, communications, computers, controllers, other equipment, and so forth which are not shown may also be included in an automated environment. For example, after an object has been processed on the automated transport 1950, a robotic, automated, and/or manual operation may place the respective object on another line or cell (not shown) for further inspection, manufacturing and/or process such as for further processing or packaging the object 1960 for shipping, as an example. As can be appreciated, the analyzers 1920–1928 and associated optics 1930–1938 can be adapted to inspect/manufacture similar parameters/portions of a respective object or objects such as a parallel inspection/assembly operation, wherein a plurality of objects are inspected/manufactured in a concurrent manner and in accordance with a similar process.

In another aspect, the analyzers and associated optics can be adapted according to different aspects, wherein a respective cell is configured to inspect/manufacture one portion of a respective object and another cell is configured to inspect/manufacture a different or subsequent portion of a respective object in a serial manner. In addition, the present invention can operate in accordance with a combination of serial and/or parallel inspection/assembly operations, wherein a plurality of cells are adapted to cooperate in some instances in a concurrent manner, in some instances in a serial manner, and in other instances in a combination of serial, parallel and/or concurrent operations. As can further be appreciated, adaptations of one or more cells can be achieved via software/programmatic configurations, hardware configurations, and/or combinations thereof.

Figure 20:
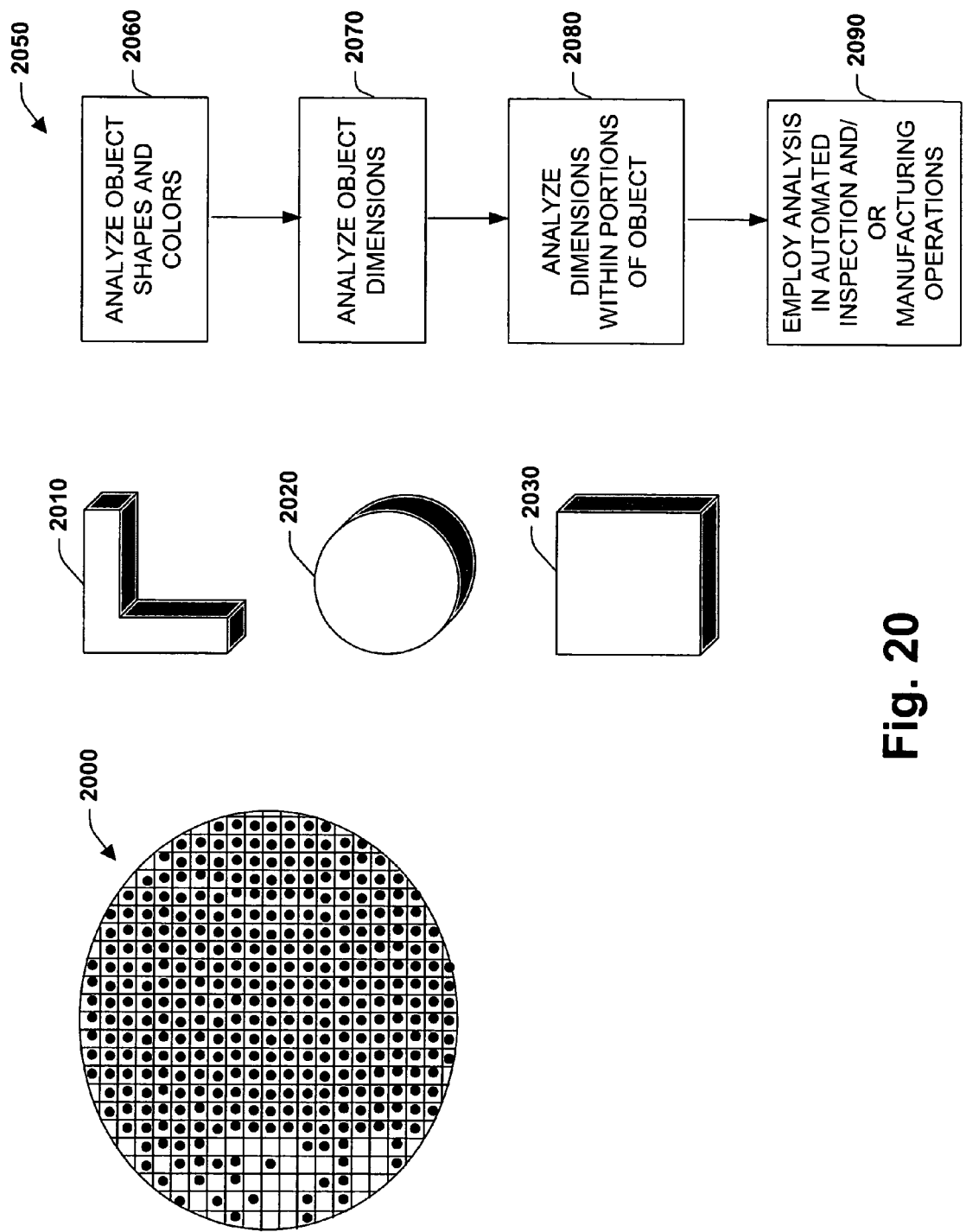
FIG. 20 illustrates exemplary objects for inspection and/or manufacturing in accordance with an aspect of the present invention.

FIG. 20 illustrates exemplary objects for inspection and/or manufacturing in accordance with an aspect of the present invention. As one example of an object, a semiconductor wafer is illustrated at 2000. The wafer 2000 is depicted as having at least one segment wherein respective segments are associated with a darkened point for illustrative purposes. These points—which do not necessarily have to be associated with a wafer 2000, can represent substantially any type of semiconductor portion, circuit, and/or feature (mechanical, material, and/or electrical). Such portions or features include for example, but are not limited to: any type of circuits, gates, memories, transistors, FET's, logic devices, diodes, films, LED's, organic devices, displays, LCD's, resistors, capacitors, inductors, fuses, amplifiers, oscillators, timers, counters, micro-code sections, gate arrays, programmable gate arrays, PLD'S, PAL's, microprocessors, microcontrollers, computers, micro-machines, micro-portions or elements, MEM's devices, bonding elements, connecting wires, vias, openings, traces, lines, patterns—any type (e.g., point, 2D, 3D), trenches, grooves, separations, spaces, distance between elements, layers, stacks of layers, portions or elements having different depths, electrical/mechanical shorts/opens, and so forth.

In a more generalized discussion of objects that may be manufactured and/or inspected in accordance with the present invention, three exemplary items are illustrated at 2010 through 2030. At 2010, an angular structure is depicted, whereas a cylindrical and a cubic structure are illustrated at 2020 and 2030 (other shapes/dimensions may be employed). These exemplary objects 2010–2030 can be analyzed/manufactured for substantially any type of dimensional aspect (objects do not have to be three dimensional). For example, the object at 2010 can represent a trace and can be analyzed for width, length, depth, and proximity to other objects, if desired, including such aspects as critical dimensions, line widths, line spacing, line quality, opens, shorts, pattern match or pattern quality and so forth. Objects 2020 and 2030 can represent such features as for example: vias, openings, raised features, indented features, recessed features, grooves, trenches, connectors, and so forth.

As can be appreciated other type features and other type objects can be analyzed, inspected, and/or manufactured in accordance with the present invention. Proceeding to diagram 2050 of FIG. 20, and at reference 2060, substantially any type of object can be processed having substantially any type shape, color, transparency, opaqueness, size, composition and/or material. Such objects can include for example: points, lines, planes, circles, squares, rectangles, ellipsoids, triangular structures, polygonal structures, spherical structures, cubic structures, cylindrical structures, trapezoidal structures, columns, and various combinations thereof. At 2070, substantially any dimensional aspect of an object can be measured in accordance with the present invention. Such dimensions include for example, length, width, depth, angles, separations between objects, pattern matching, color matching, and so forth. As noted above, predetermined thresholds can be established. For example, if a line object is measured for a width or length, predetermined thresholds can be set or configured, wherein if the line measures within a range (e.g., not too long/not too short, not to wide, not too narrow) then the line can be categorized as being within specifications, otherwise, the measured line can be rejected and/or logged as not meeting specifications. Alternatively, objects can be compared with existing images of object portions within a database for example, wherein analysis can be based on a plurality of criteria such as the number of matching pixels between a measured object and a stored object or object portion. As can be appreciated, such analysis can include substantially any custom or commercially available software to facilitate such analysis.

At 2080, not only can respective objects or features be analyzed as previously discussed, but features and dimensions within portions of respective objects or associated with respective objects can be similarly analyzed. Thus, any given object to be analyzed can include various combinations of materials, properties, parameters, and/or features previously described within all or portions of the object. Likewise, a given object to analyze may include a combination of smaller objects that are similarly or differently configured that cooperate to form the object under inspection or manufacture. At 2090, all or portions of the above processes, analysis, determinations, and/or measurements can be employed in an automated inspection and/or manufacturing operation. Such aspects can include utilizing the above determinations and measurements in a control loop, control feedback, and/or control algorithm to facilitate such operations.

Figure 21:
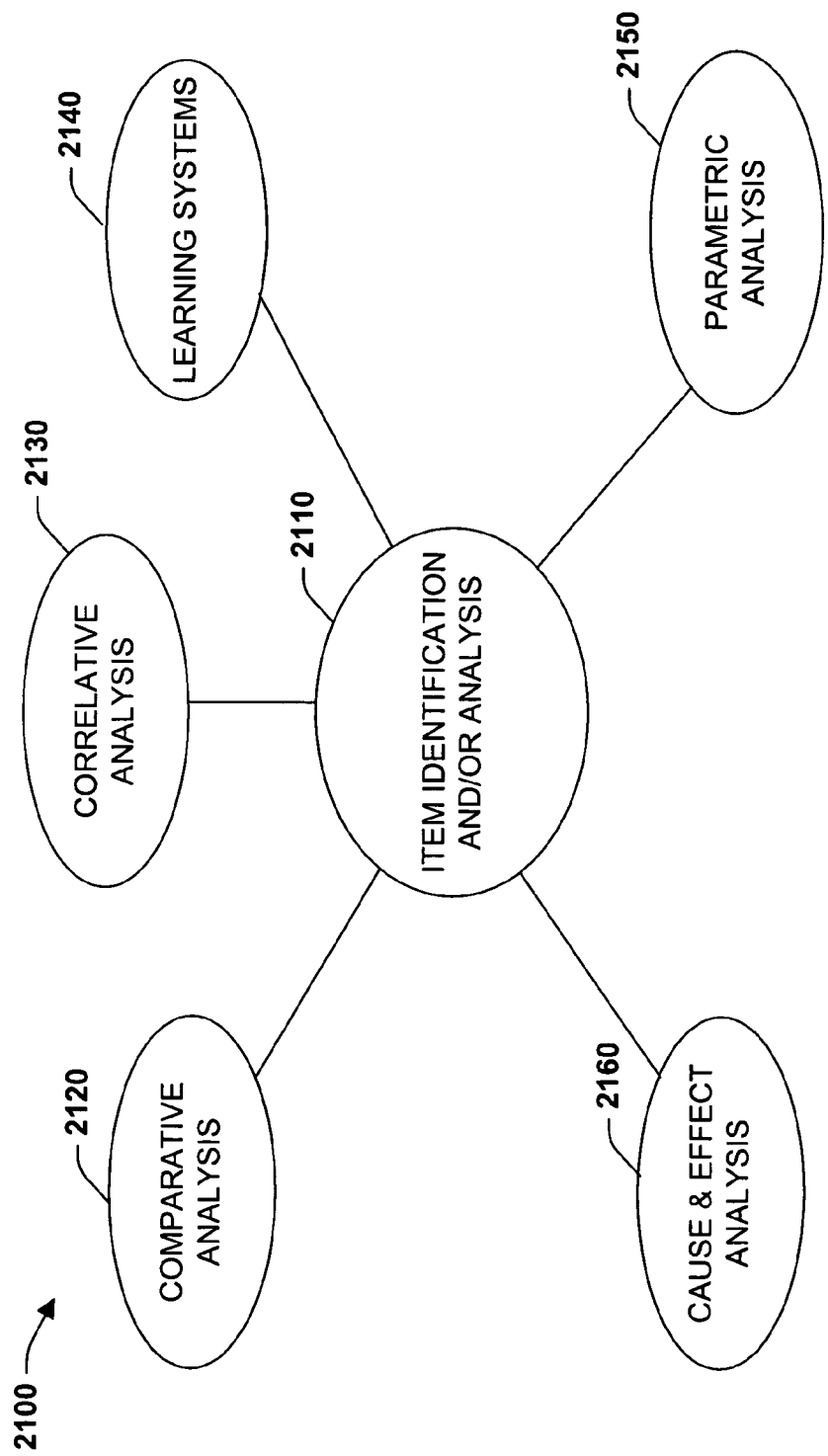
FIG. 21 illustrates exemplary particle, material, and/or component analysis in accordance with an aspect of the present invention.

FIG. 21 illustrates various exemplary analytical techniques 2100 that may be employed for component, particle, and/or material identification and/or analysis in accordance with an aspect of the present invention. It is to be appreciated that the analytical techniques 2100 can be applied with any of the systems, processes, and/or particles/materials/objects/shapes . . . and so forth described herein. An analyzer 2110 is provided to identify, analyze and/or determine one or more items such as an object, component, particle and/or material, for example. The analyzer 2110 can include automated techniques such as software operating on a computer, wherein respective items to be analyzed are first imaged and analyzed in accordance with a plurality of previously stored components, images, and/or parameters in a database or file to facilitate identification/analysis of the respective item. It is to be appreciated that item identification can also include manual analysis such as viewing an image from a display or invoking software that inputs an image to be analyzed, for example, and/or include combinations of manual and/or automated techniques. Software can include commercially available software (e.g., Matlab) and/or include developer software to facilitate the analysis (e.g., write Visual C++ routine employing equations, artificial intelligence or statistical models).

The analyzer 2110 includes one or more of the following exemplary techniques/components to identify/analyze an item in accordance with the present invention, although it is to be appreciated that other techniques may be employed. At 2120, comparative techniques can be employed. This includes comparing captured images to previously stored images on a database to determine a match (or close to a match defined by predetermined matching criteria), performing database lookups, and/or performing digital subtraction between images to determine differences (e.g., after performing subtraction, making a particle identification based on fewest non-subtracted bits appearing in a resultant bit map). At 2130, correlative analysis can be applied. Correlative analyses can include comparisons to a database of (but not limited too) either complete/partial visual image data, and/or component image data (e.g., FFT, or other frequency, and/or spatial or other intrinsic parametric image data derived from the image via image processing and/or direct optical correlation of the existing k-space frequency field created in accordance with the present invention from the imaged object, component, particle, and or materials, for example). Such techniques are described in more detail below with reference to FIGS. 22 and 23.

At 2140, intelligent and/or learning systems can be applied for item identification. Such aspects include neural networks, classifiers, inference models, artificial intelligence and/or other learning models (e.g., Support Vector Machines (SVM), Bayes, Naive Bayes, Bayes Net, decision tree, similarity-based, vector-based, Hidden Markov Models and/or other learning models or combinations thereof) (can include hand-crafted models). The learning systems 2140 are trained to identify (or infer) an item based upon past training (or inferences) of similar items, wherein an imaged item is input to a trained model for identification purposes. It is noted that combinations of learning models or systems can be employed including hierarchical arrangements of such models, wherein output from one or more models is provided to a subsequent model or set of models for further analysis or inference. This also includes substantially any statistical and/or probabilistic technique, process, equation and/or algorithm for analyzing an item and making an identification based upon statistical, analytical and/or probabilistic similarities or differences with previously stored images or parameters (e.g., making an identification by determining if item measurements or samples fall within statistical and/or probabilistic thresholds).

Proceeding to 2150, parametric analysis can be provided for determining an item. In this aspect, a captured image is automatically parameterized for such characteristics as size, shape, morphology, thickness, other objects or vacancies appearing therein, diameter, length, circumference, three-dimensional qualities, and so forth. When the parameters have been determined, previously stored parameters for known particles are then compared to the determined parameters. If an item compares favorably (within predetermined threshold) of a stored parameter or parameter set associated with a known particle, then an identification can be made based upon the parametric comparison or similarity.

At 2160, a cause and effect analysis can be provided in accordance with the present invention. In this aspect, items are observed for known reactions to specified events and/or applications thereof (measurements or images can also be captured over time or at predetermined times after event). For example, this can include item reactions to illumination, radiation, and temperature variations based upon an application of such events.

Thus, if temperature were increased or decreased for a respective item as the event or cause, for example, and the imaged item contracted or expanded over time in accordance with a known contraction or expansion as the reaction or effect to the respective event, then an item identification can be made based upon a comparison to other known reactions (contraction/expansion of particle size/shape) that have been previously stored or cataloged.

Other reactive causes or stimulating events can include observations or determinations of chemical reactions, mechanical reactions (e.g., reaction to shock, vibration oscillation, motion and so forth), mixing reactions such as mixing an item with another item and observing interactions and/or distributions of the respective items, and/or electrical reactions (e.g., applying voltages, currents, magnetic fields, electrical fields, frequencies, waves, and so forth to a respective item, observing the effect of such electrical stimuli, and comparing the effects with known samples that have been similarly stimulated and/or comparisons with data derived/modeled therefrom).

Figure 22:
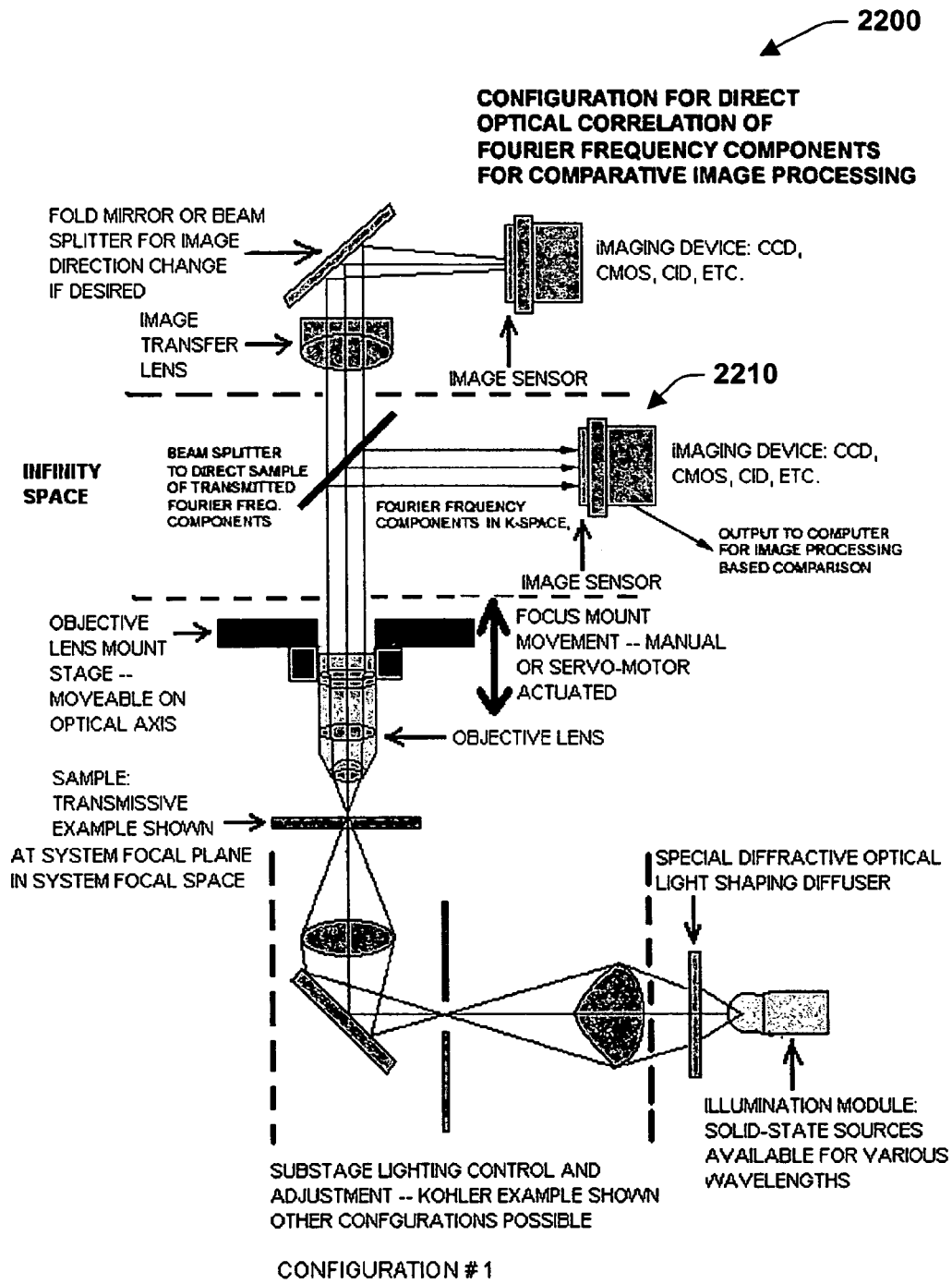
FIGS. 22 and 23 illustrate correlative imaging techniques in accordance with an aspect of the present invention.
Figure 23:
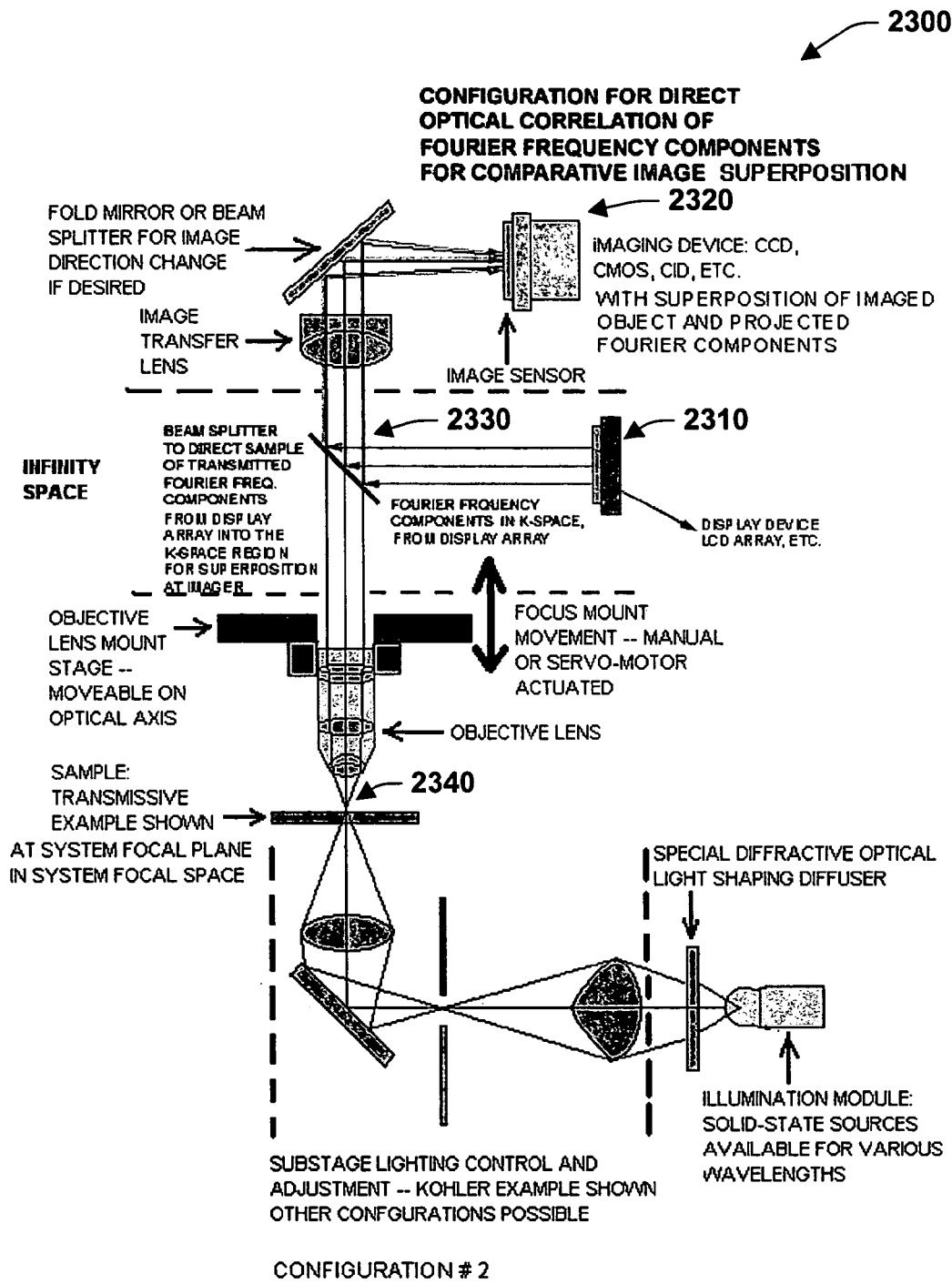

FIGS. 22 and 23 relate to correlative imaging techniques in accordance with an aspect of the present invention. Correlative and/or comparative analyses can include (but not limited too) comparisons to a database of visual image data, and/or component image data (e.g., FFT, or other frequency, and/or spatial or other intrinsic parametric image data derived from the image via image processing or direct optical correlation of existing k-space frequency field created in accordance with present invention from the imaged object.) The existing frequency field created in the infinity-space volume of the present invention can be exploited and directed employing optical components. For example, the Fourier Transform or uncorrelated FFT, which exists in the k-space volume, can be employed as previously mentioned for optical correlation with an existing database of directly and/or empirically derived cataloged Fourier Transform or FFT data or Image-Processing transformation-based cataloged FFT data.

Referring now to FIG. 22, a configuration 2200 defines that an existing, unmodified k-space Fourier Transform or FFT itself be imaged by an image array (CCD, CMOS, CID, and so forth) at 2210 and then that image (which is the extant actual FFT which can be appreciated as an "instant FFT or "unprocessed FFT") can be compared via any commercial or specially designed Image Processing algorithm to FFT images stored in an associated database (not shown). FIG. 22 illustrates such a configuration 2200. Though this configuration 2200 depicts only one exemplary optical configuration (e.g., employing a microscope objective) it will be appreciated that such is applicable to previously discussed configuration variants herein.

The configuration 2200 defines a direct imaging optical correlator as opposed to conventional FT-pair lens configuration used for crude-resolution optical correlation and processing. This configuration 2200 also obviates problems limiting image frequencies since the intrinsic filtration of the k-space image field defines the pass band. This implies that correlated information fills the necessary/sufficient conditions for about 100% correlation. This is unlike conventional image processing of spatial/frequency transforms which are decoded (actually reverse transformed) for comparison, correlation and imaging for inspection of the created image.

FIG. 23 illustrates an alternative configuration 2300 that defines that a cataloged image of an existing FFT be projected to a display 2310, and superimposed with an image at sensor 2320 to achieve a comparative correlation. The configuration 2300 illustrates that the display device 2310 (e.g., LCD, etc.) displays (is "programmed" with) an image of the FFT of a given object. The displayed FFT image is back projected into a k-space volume of the device at 2330 and is subsequently imaged in a superposition with an object from a focal plane at 2340. The superposition of actual FFT (frequency fields) achieves various aspects of the present invention. In one aspect, it is a projection of two fields (or more) that are directly correlated at the imager 2320 and defines a 100 percent correlation (or thereabout) in Fourier-space which obviates or mitigates requirements for inverse transform matching for correlation. It also obviates or mitigates associated frequency errors and uncertainty (i.e., "noise") since the transmitted (or rather projected) FFT fields derive from an intrinsic k-space pass-band filtration in accordance with the present invention.

Such correlations can be employed to directly identify or verify that a database object exists in the field of view, or prove that no such object appeared in the field of view. This is achieved when the FFT-display is "programmed" with the image of the FFT of a particular database cataloged object and that FFT projection is superposed with that of the object in the focal plane at 2340. The superposition is additive if the same FFT frequency components exist in each of the superposed components resulting in a unique correlation-feature seen by the imager at 2320. This correlation-feature defines a "match" or "correlation" of the superposed fields and is characterized by a recognizable digital "glow" or "brightness enhancement" called "sparkle." Sparkle being characterized as a defined "spike" or maximum in the superposed frequency components at a given center frequency within the k-space pass band. Such spikes define a correlation at that frequency. If they do not correlate then there is typically no "sparkle." The correlation and identification of objects with cataloged database objects is generally immediate and independent of an object's spatial position or size since these parameters do not affect the object's transmitted frequency components. Images of the object or objects in the field of view can (but are not limited to) be captured for storage, processing, and/or visually inspected in real time by direct observation.

Figure 24:
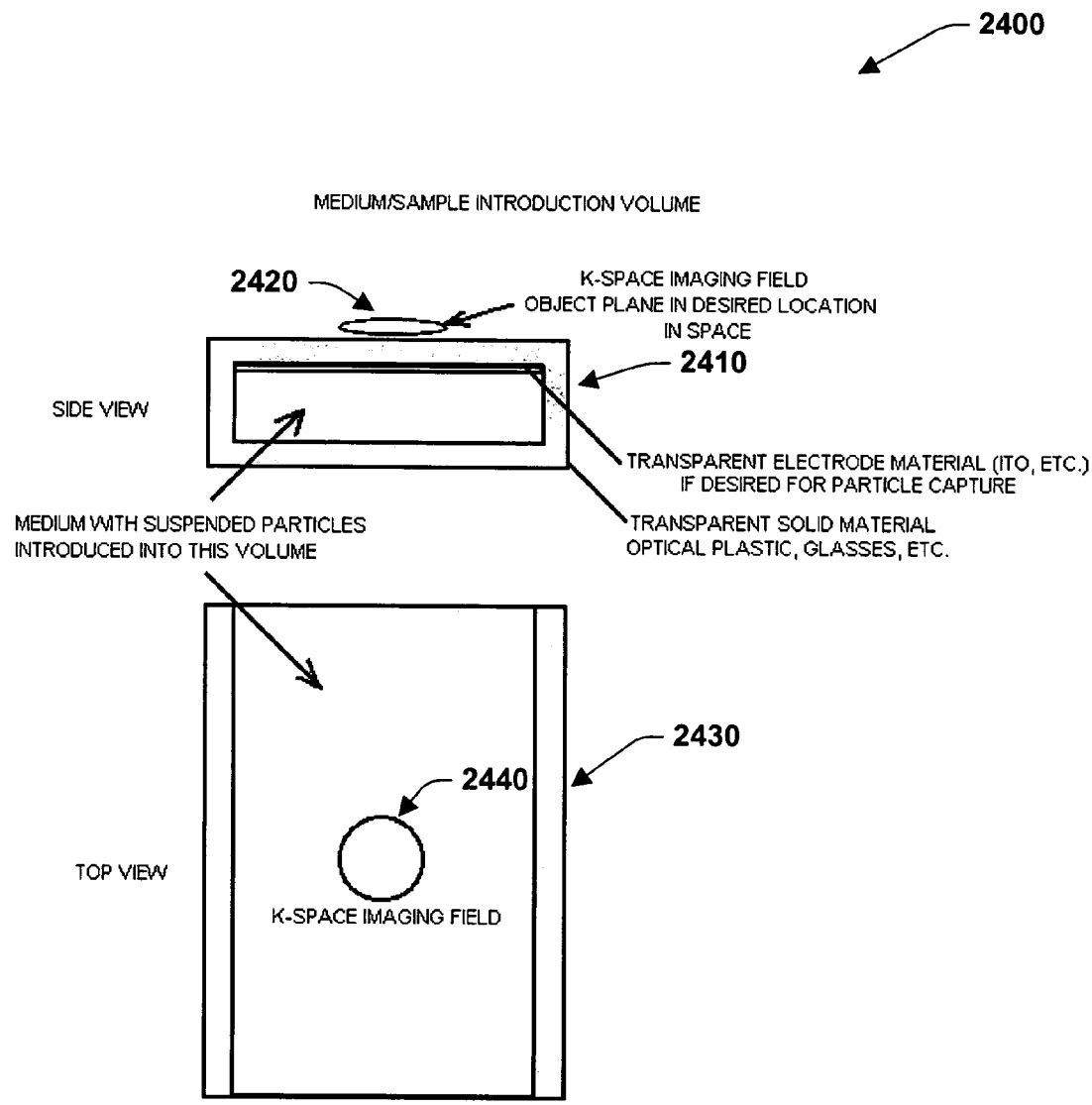
FIG. 24 illustrates a system for suspended particulate detection/imaging in gaseous, liquid, transmissive and/or solid mediums in accordance with an aspect of the present invention.

In the foregoing discussion relating to FIG. 24, "objects" refer to anything suitably placed in a focal plane to be imaged. This includes (but is not limited to) objects that are either externally illuminated via transmissive or reflective illumination or self-illuminated (e.g., fluorescent or phosphorescent through appropriate excitation). This includes (but is not limited to) any objects, subjects, segments or parts of objects, or features of objects (either single or multiple such features). Examples include (but are not limited to) particles, cells, parts of particles or cells, and features of particles or cells. This also includes (but is not limited to) opaque objects (e.g., particles, semiconductors, features of pariticles, semi-conductors, and so forth).

FIG. 24 illustrates a system 2400 for suspended particulate detection/imaging in gaseous, liquid, transmissive and/or solid mediums in accordance with an aspect of the present invention. As discussed previously, various techniques can be employed to image moving particles such as via timing, shutter and strobing processes, for example. These techniques have the effect of capturing an image of "apparently" motionless or "freeze-frame" particles—even though the particles themselves may not in fact be motionless. According to this aspect of the present invention, various techniques are described for imaging particles, whereby particle motion is stopped and/or altered in order to facilitate image capture in accordance with the present invention.

The system 2400 includes a side view of a chamber 2410 for receiving particles that can be imaged in accordance with a viewing portal, observation field, transparent opening, or through an appropriate transparent "window" surface 2420 (entire chamber 2410 can be transparent for viewing). 2420 represents the imaging Field Of View of the k-space imaging field at the object plane in the desired location. A top view of the chamber 2410 is illustrated at 2430 illustrating a viewing area 2440 for imaging systems adapted in accordance with the present invention. It is noted that the chamber 2410, 2430 can be substantially any volumetric container (e.g., tubular, triangular, cubic, rectangular and so forth), whereas the image field (viewing area) 2420, 2440 can be "vignetted" by various shapes (e.g., circular, square, rectangular, elliptical, triangle, and so forth). The chamber 2410 is employed to alter particle motion to facilitate imaging in accordance with the present invention. As will be described in more detail below, the chamber 2410, 2430 can employ various techniques to slow or advance particles such as electrostatic techniques, magnetic techniques, mechanical techniques, and/or pressure techniques. In addition, the chamber 2410, 2430 can be employed with one or more of the illumination techniques previously described such as via strobe-illumination, for example.

In one aspect, the chamber 2410 can be employed when a gaseous medium in which "particles" as previously described are suspended, carried, flowed, or otherwise contained, etc., is introduced into the observation-field 2420 of the instrument. This can be achieved by flowing gaseous medium (e.g., by pump pressure or vacuum pressure difference) through a transparent tube of appropriate size to match/correlate the depth of field (DOF) and field of view (FOV) (round or rectangular (also square) cross section for observation (imaging) of a specific volume in real time. This will facilitate the characterization of the particulates as described above.

In another aspect, flowing gaseous medium in which "particles" as previously described are suspended, carried, flowed, or otherwise contained, etc., can be (e.g., if inert and non-explosive) imaged in a "chamber or space or volume" 2410 having flat transparent walls. This may also be a transparent tube. The walls of the space are electrically sensitized via some suitably conductive medium such as a coated transparent electrode deposited on the wall of the chamber 2410. An electric field can be introduced into this coating or electrode material. Such an electric field can be energized at desired intervals in time and, through the action of static charge, will then "capture the suspended particulates in the volume of the space and cause them to collect against the transparent wall (electrode) of the space where they can be imaged by the imaging system and facilitate characterization of the particulates as described above. Conversely, it will be appreciated that an opaque electrode may be employed in the same manner such that suspended particles are captured on that surface and illuminated non-transmissively for imaging.

In yet another aspect, a variation in gas pressure can be introduced into the chamber 2410 at desired intervals in time and, through the action of evacuation or partial evacuation will then "capture" the suspended particulates in the volume of the "space, etc." and cause them to collect against the transparent wall of the "space, etc." where they can be imaged by the imaging systems previously described and allow the characterization of the particulates as described above.

In still yet another aspect, a gaseous medium is introduced into the observation field or viewing area 2420 of the chamber 2410, wherein particles suspended within the gaseous medium may be influenced by magnetic fields. The "chamber or space or volume" of the chamber 2410 can be mounted in such a way as to be within or surrounded by a magnetic field through the space. This may include permanent and/or electromagnetic devices. This can include coils of conductive material (windings) separate from and/or integral with the "chamber or space or volume". A magnetic field can be introduced and can be energized at desired intervals in time and, through the action of the induced magnetic field and will then "capture the suspended particulates in the volume of the space within the chamber 2410 and cause them to collect against the transparent wall of the space where they can be imaged and characterized as described above. Conversely, it will be appreciated that an opaque electrode may be employed in the same manner such that suspended particles are captured on that surface and illuminated non-transmissively for imaging.

As can be appreciated, multiple variations can be employed for imaging particles in accordance with electrostatic, magnetic, mechanical, electronic, and/or pressurized motion techniques. These variations include applying electrical, magnetic, and/or pressurized (e.g., liquid pressure, mechanical pressure) forces to optically transmissive liquid mediums having particulates contained therein and subsequently imaging particles as described above. In another aspect, solid materials having particles trapped therein (can be optically transmissive solid material or opaque material for surface analysis) may be manipulated and/or imaged in accordance with the present invention. For example, solid material may be mechanically stopped and/or positioned (via control system) within the chamber 2410 while particle imaging occurs.

In another aspect of the present invention, an imaging system adapted as described above provides high Effective Resolved Magnification and high Absolute Spatial Resolution among other features of, but not limited to, Fiber-Optic (and other wave-guide) structures, materials, fibers, cables, connectors, welds, attachments, fusion, splices, process monitoring, fabrication, and methods that can be combined to provide improved Fiber optic imaging systems and methods.

The present invention may be configured and disposed in such a way as to allow imaging of any of the forgoing Fiber-Optic materials either or, but not limited to, the ends of fibers or multiple fibers, or bundles of fibers, etc. in such a way as to be essentially but not limited to directions perpendicular to the direction of propagation of radiation in the wave-guide. Likewise, the present invention can be configured and disposed in such a way as to allow imaging of any of the forgoing Fiber-Optic materials either or, but not limited to, fibers or multiple fibers, or bundles of fibers, etc. in such a way as to be essentially but not limited to directions parallel to the direction of propagation of radiation in the wave-guide.

The Fiber-Optic imaging systems and methods of the present invention enable the production of improved images (higher Effective Resolved Magnification (ERM), improved Absolute Spatial Resolution (ASR), improved depth of field, and the like) leading to the inspection and identification of Fiber-Optic materials as well as the manipulation, repair, inspection, and classification of Fiber-Optic materials (for example as normal or abnormal).

Fiber-Optics as defined in this application include but are not limited to all optical transmission media of macroscopic, microscopic, and even nanoscopic scale. This is also understood to include singe fibers, bundles, cables, single core, multi-core, polarization preserving, circular and non-circular core fibers, glass, plastic, quartz, and any other optical material for transmission of radiation in a wave-guide configuration. Since the Fiber-Optic imaging system of the present invention can employ a relatively large working distance with the advantage of higher ERM and ASR than conventional instrumentation has traditionally allowed, it will enable, easier manipulation, higher efficacy, greater accuracy, and better repair, for example when used as the imaging component in a splicing or fusion apparatus which requires precision and the highest accuracy in positioning of fiber optic components to be "spliced" by fusion welding, bonding, or any other method for aligning and joining fiber "ends" into a continuous fiber length. The present invention is applicable to other Fiber-Optic related imaging applications which require accuracy, precision, and high Absolute Spatial Resolution imaging at a given magnification. The foregoing can also be applied, but not limited to, automated imaging applications for inspection, quality control, fabrication, process control, and the like.

It will therefore also be appreciated that design and definition applications of the present invention will also apply to radiation that includes, but is not limited to, X-Radiation (also called x-rays, roentgen-radiation, x-brehmstrahlung, synchrotron, etc.) with wavelengths generally within, but not explicitly limited to, the spectral bandwidth approximately between 0.1 Å (Å meaning Angstrom Units of wavelength), or 0.00001 micron, and 100 Å, or 0.01 micron. Radiation of this kind is of such short wavelength and high frequency that it is generally discussed in terms of Energy expressed in Electron-Volts (eV). Thus the previously defined bandwidth is also defined as being from 100 keV for 0.1 Å to 100 eV for 100 Å x-rays.

It will be further appreciated therefore that radiation of these particular wavelengths whose optical path, direction, and/or path length can thus be altered by means of an "optical medium", surface, material, component, or components, or other such means suitable to radiation of that wavelength in the configuration or configurations pertaining to the direction of such radiation to achieve the desired characteristics in the present invention) received from the items under examination in the object field of view.

X-radiation is generally not directable using conventional refractive physical optics of any material at present, (but the foregoing descriptions of an "optical medium" would also apply to such should it exist), but optical path length and focusing of x-rays is currently possible employing optical systems based on reflective "Grazing Incidence" techniques, and most currently, advanced diffractive "Zone-plate", and "layered refractive" optics technology.

With reference to reflective X-ray optics for direction of X-rays: The main difference between normal incidence optics for visible and near-, or quasi-visible light wavelengths and X-ray optics consists of the strong dependence of X-ray reflection on the angle of incidence of the photons with respect to the surface. Small incident angles make reflection possible in the X-ray band. Such optics are thus called "Grazing Incidence" (GI) optics. The reflecting surface has a low micro-roughness (generally less than or equal to 0.5 nm rms). Also, a material with high reflectivity for X-ray wavelengths is most useful, such as Gold which has the highest reflectivity between 0.1 keV and 10 keV. GI optics make use of the low angles of incidence to effectively "skip" X-ray photons of the surfaces like a stone skipped off a pond surface. Special optical designs for GI optics have been devised for various energy X-rays and can direct and focus this radiation in a way analogous to visible light.

It will be appreciated that an appropriate set of GI optics to act as a primary "condenser" of incident X-rays to an object and also as both "Objective" and "relay" mirrors analogous to the visible-light refractive optical components could be devised to define a given Field of View and effective Numerical Aperture in such a way as to direct X-rays through an "object" in an object-plane and subsequently through an intrinsic k-space filter analogous to that previously described. The exiting X-ray flux, being filtered by the "optical media" through the intrinsic k-space filter as previously described in much the same way as for visible light would then be directed toward a detector (sensor) designed to be sensitive to X-rays of any desired energy. It is understood that resolution, path length, aberration, and other optical parameters of the incident and focused X-ray "illumination" are dependent strongly on intrinsic parameters such as monochromaticity, collimation, coherence, etc. and that these parameters are controllable by the inclusion of components such as pinholes, physical spatial filters, and other "optical components" to modify the incident radiation prior to its direction through the "object" and the optical system of the invention.

With reference to Diffractive "zone-plate" optics for X-ray direction and focusing: Since resolution determination in X-ray microscopy is generally dependent on criteria such as partial coherence, illumination spectrum, etc. current advances in nano-fabrication techniques has resulted in the development of deposited diffractive "zone-plate" optics ("lenses") with general Fresnel zone-plate geometry designed to diffract and direct incident X-rays much like well known Fresnel lenses do with visible light. The resulting optics cause X-rays to behave essentially with all the general physical parameters understood and observed by radiation in the visible spectrum. As such, Zone-plate lenses have been used to create "standard" so-called "high-resolution" X-ray microscopes. These optics have supplanted the use of reflective optics for this purpose, being generally easier to fabricate and more robust, as well as physically smaller. These current state-of-the-art X-ray microscopes have generally employed zone plate-optics to condense, focus, and direct incident X-rays through objects and onto a CCD camera with sensitivity parameters specific to the incident X-ray energies (wavelengths). These devices are subject to the same limitations in their wavelength regime as visible light optical microscopes, and thus the present invention can be extended to X-ray microscopes.

With reference to "Layered Refractive" optics for X-ray direction and focusing: New and current advances in x-ray optical theory and fabrication technique has resulted in the development of "Layered Refractive" x-ray optics ("lenses") with general geometry designed to direct incident X-rays through multiple layers of materials with appropriately designed optically curved surfaces much like well known lenses for refraction of visible light radiation. The known various extant designs of "Layered Refractive" x-ray optics cause X-rays to behave essentially with the general physical parameters understood and observed by radiation in the visible spectrum incident through refractive optical media. This being the case, "Layered Refractive" x-ray lenses can be used to create "high-resolution" X-ray microscopes. These optics can supplant the use of reflective and diffractive optics for this purpose. The current state-of-the-art X-ray microscopes have generally employed zone plate-optics to condense, focus, and direct incident X-rays through objects and onto a CCD camera with sensitivity parameters specific to the incident X-ray energies (wavelengths). Likewise they can employ "Layered Refractive" x-ray optics to do the same. These devices are subject to the same limitations in their wavelength regime as visible light optical microscopes, and thus the present invention can be extended to X-ray microscopes.

It will therefore be appreciated in this aspect that an appropriate set of "Layered Refractive" x-ray optics can be devised to act as a primary "condenser" of incident X-rays to an object and also as "Objective" and "relay" optics analogous to the visible-light refractive optical components to define a given Field of View and effective Numerical Aperture in such a way as to direct X-rays through an "object" in an object-plane and subsequently through an intrinsic k-space filter between "objective" and "relay" analogous to that previously described. The exiting X-ray flux, being filtered by the "optical media" through the intrinsic k-space filter in much the same way as for visible light would then be directed toward a detector (sensor) designed to be sensitive to X-rays of any desired energy. It is understood that resolution, path length, aberration, and other optical parameters of the incident and focused X-ray "illumination" are dependent strongly on intrinsic parameters such as monochromaticity, collimation, coherence, etc. and that these parameters are controllable by the inclusion of components such as pinholes, physical spatial filters, and other "optical components" to modify the incident radiation prior to its direction through the "object" and the optical system of the invention.

It is noted that X-rays being focused and otherwise directed by "optical media" it is to be understood that the same criteria for blur-circle, resolution, circle-of-least confusion, "chromatic" aberration, and other optical parameters of the radiation are describable by such relationships as Fresnel diffraction rules, and the Rayleigh criterion for diffraction spot of the focused radiation.

It will thus be appreciated that the object field of view thus established by the image transfer medium, e.g.: an suitable Layered Refractive lens, Fresnel Zone-plate lens, or appropriate GI optic, is related to the position of an object plane that includes one or more items under examination (not shown). Such a sensor can be any set of currently extant detectors for resolving count rate, flux, energy, position, incidence time, etc. of X-rays. Common X-ray detectors include Gas ionization, proportional, multiwire and strip, scintillation, energy resolving semiconductor, surface barrier, avalanche or other photodiode, CCD, CMOS, super conducting, microchannel or capillary plate, or others as may become available. The currently most advanced and useful of such detectors for X-ray imaging are CCD and or CMOS sensor arrays specifically designed to detect and digitize incident X-rays in much the same ways that visible light sensitive CCD's and CMOS sensors provide.

Such X-ray detectors could be arranged in such a way as to be therefore analogous to and be disposed in the same manner as optical sensors. It can be substantially any size, shape and/or technology in any suitable geometry (e.g.: an array sensor, a linear sensor, etc.) including one or more receptors of various sizes and shapes, the one or more receptors being similarly sized or proportioned to devise a respective sensor to be responsive to incident X-rays directed through or even reflected or diffracted from the object.

An aspect of the invention for use with X-rays is thus essentially analogous to that described in the invention for visible light. As X-ray flux is thus received from the object field of view, the X-ray sensor provides an output inherent to the detector (e.g., electrical current, voltage, etc.) that can be displayed directly or processed by a computer and can be directed to a local or remote storage such as a memory and displayed from the memory via the computer and associated display. It is noted that local or remote signal processing of the image data received from the sensor can also occur. For example, the output can be converted to electronic data packets and transmitted to a remote system over a network and/or via wireless transmissions systems and protocols for further analysis and/or display. Similarly, the output can be stored in a local computer memory before being transmitted to the subsequent computing system for further analysis and/or display.

What has been described above are preferred aspects of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. An imaging system, comprising:
    a sensor comprising pixels, the pixels having a pixel area of about 0.01 microns$^2$ or more and about 600 microns$^2$ or less; and
    an image transfer medium having a diffraction limited spot size area in an object plane of about 0.0003 microns$^2$ or more and about 600 microns$^2$ or less, the image transfer medium comprising a first lens positioned toward the object plane and a second lens positioned toward the sensor, the first lens sized to have a focal length smaller than the second lens to provide an apparent reduction of the pixels within the object plane,
    wherein pixels projected through the image transfer medium have a projected pixel area in the object plane of about 0.0003 microns$^2$ or more and about 600 microns$^2$ or less, the ratio of the projected pixel area in the object plane to the diffraction limited spot size area in the object plane is from about 5:1 to about 1:12.

2. The imaging system of claim 1, wherein the projected pixel area is about 0.001 microns$^2$ or more and about 200 microns$^2$ or less, the diffraction limited spot size area is about 0.001 microns$^2$ or more and about 200 microns$^2$ or less, and the ratio of the projected pixel area to the diffraction limited spot size area is from about 3.5:1 to about 1:8.

3. The imaging system of claim 1, wherein the projected pixel area is about 0.01 microns$^2$ or more and about 100 microns$^2$ or less, the diffraction limited spot size area is about 0.01 microns$^2$ or more and about 100 microns$^2$ or less, and the ratio of the projected pixel area to the diffraction limited spot size area is from about 3:1 to about 1:6.

4. The imaging system of claim 1, wherein the sensor comprises pixels having substantially the same pixel area and substantially the same shape.

5. The imaging system of claim 1, wherein the sensor comprises a first subset of pixels having a first pixel area and a second a subset of pixels having a second pixel area, the first pixel area different from the second pixel area.

6. The imaging system of claim 1, further comprising an LED illumination source.

7. The imaging system of claim 1, wherein the sensor comprises a plurality of stacked pixels, where each pixel in a stack has substantially the same size.

8. The imaging system of claim 7, wherein each stack of pixels comprises two, three or four pixels.

9. An imaging system, comprising:
    a sensor comprising pixels, the pixels having a pixel pitch of about 0.1 microns or more and about 20 microns or less; and
    an image transfer medium having a diffraction limited spot in an object plane having a diameter of about 0.01 microns or more and about 20 microns or less, the image transfer medium comprising a first lens positioned toward the object plane and a second lens positioned toward the sensor, the first lens sized to have a focal length smaller than the second lens to provide an apparent reduction of the pixels within the object plane,
    wherein pixels projected through the image transfer medium have a projected pixel pitch in the object plane of about 0.01 microns or more and about 20 microns or less, the ratio of the projected pixel pitch in the object plane to the diffraction limited spot diameter in the object plane is from about 1:1.9 to about 1.9:1.

10. The imaging system of claim 9, wherein the projected pixel pitch is about 0.05 microns or more and about 15 microns or less, the diffraction limited spot diameter is about 0.05 microns or more and about 15 microns or less, the ratio of the projected pixel pitch to the diffraction limited spot diameter is from about 1:1.5 to about 1.5:1.

11. The imaging system of claim 9, wherein the projected pixel pitch is about 0.1 microns or more and about 10 microns or less, the diffraction limited spot diameter is about 0.1 microns or more and about 10 microns or less, the ratio of the projected pixel pitch to the diffraction limited spot diameter is from about 1:1.3 to about 1.3:1.

12. The imaging system of claim 9, wherein the image transfer medium comprises an objective lens system and a transfer lens system.

13. The imaging system of claim 12, wherein the objective lens system comprises a single objective lens or a plurality of lenses.

14. The imaging system of claim 9, wherein the sensor comprises a plurality of stacked pixels, each pixel in a stack has substantially the same size, and each pixel in a stack captures a different range of wavelengths of light.

15. The imaging system of claim 9, wherein the image transfer medium having a diffraction limited spot in an image plane having a diameter of about 0.1 microns or more and about 20 microns or less, wherein the ratio of the pixel pitch to the diffraction limited spot in the image plane is from about 1:1.25 to about 1.25:1.

16. An imaging system, comprising:
    a sensor comprising pixels, the pixels having a pixel width of about 0.1 microns or more and about 20 microns or less; and
    an image transfer medium having a diffraction limited spot in an object plane having a diameter of about 0.01 microns or more and about 20 microns or less, the image transfer medium comprising a first lens positioned toward the object plane and a second lens positioned toward the sensor, the first lens sized to have a focal length smaller than the second lens to provide an apparent reduction of the pixels within the object plane,
    wherein pixels projected through the image transfer medium have a projected pixel width in the object plane of about 0.01 microns or more and about 20 microns or less, the ratio of the projected pixel width in the object plane to the diffraction limited spot diameter in the object plane is from about 1:1.9 to about 1.9:1.

17. The imaging system of claim 16, wherein the pixels have at least one of a rectangular shape and a square shape.

18. The imaging system of claim 16, wherein the projected pixel width is about 0.05 microns or more and about 15 microns or less, the diffraction limited spot diameter is about 0.05 microns or more and about 15 microns or less, the ratio of the projected pixel width to the diffraction limited spot diameter is from about 1:1.7 to about 1.7:1.

19. The imaging system of claim 16, wherein the projected pixel width is about 0.1 microns or more and about 10 microns or less, the diffraction limited spot diameter is about 0.1 microns or more and about 10 microns or less, the ratio of the projected pixel width to the diffraction limited spot diameter is from about 1:1.2 to about 1.2:1.

20. The imaging system of claim 16 further comprising an illumination source providing at least about 75% of illumination energy having a wavelength range from about 100 nm to about 2,000 nm.

21. The imaging system of claim 1, further comprising an LED illumination source and at least about 75% of light energy produced by the LED illumination source has a wavelength range from about 100 to about 10,000 nm.

22. The imaging system of claim 9, further comprising an LED illumination source and at least about 75% of light energy produced by the LED illumination source has a wavelength range from about 400 to about 700 nm.

23. The imaging system of claim 16, further comprising an LED illumination source and at least about 75% of light energy produced by the LED illumination source has a wavelength range from about 350 to about 1,000 nm.

* * * * *